US006365348B1

(12) United States Patent
Reed et al.

(10) Patent No.: US 6,365,348 B1
(45) Date of Patent: Apr. 2, 2002

(54) COMPOUNDS FOR DIAGNOSIS OF BREAST CANCER AND METHODS FOR THEIR USE

(75) Inventors: Steven G. Reed; Jiangchun Xu, both of Bellevue, WA (US)

(73) Assignee: Corixa Corporation, Seattle, WA (US)

( * ) Notice: Subject to any disclaimer, the term of this patent is extended or adjusted under 35 U.S.C. 154(b) by 0 days.

(21) Appl. No.: 09/118,554

(22) Filed: Jul. 17, 1998

Related U.S. Application Data

(63) Continuation-in-part of application No. 08/998,255, filed on Dec. 24, 1997, now abandoned.

(51) Int. Cl.[7] ........................... C12Q 1/68; G01N 33/48
(52) U.S. Cl. ............................................. 435/6; 436/64
(58) Field of Search ................................ 435/6; 436/64

(56) References Cited

U.S. PATENT DOCUMENTS

| | | | |
|---|---|---|---|
| 5,643,761 A | 7/1997 | Fisher et al. | |
| 5,688,641 A | 11/1997 | Sager et al. | |
| 5,962,262 A | 10/1999 | Hillman et al. | |

FOREIGN PATENT DOCUMENTS

| | | |
|---|---|---|
| WO | WO 98/18945 | 5/1998 |
| WO | WO 98/42738 | 10/1998 |
| WO | WO 99/23230 | 5/1999 |
| WO | WO 99/40189 | 8/1999 |

OTHER PUBLICATIONS

Brewer et al., 1998, GENESEQ, Accession #X00704.*
Dillon et al., 1998, GENESEQ, Accession No. V58695.*
Ryan et al., 1999, GENESEQ, Accession No. X23517.*
Harris et al., 1995, J. of The Am Society of Nephrology 6:1125–33.*
Ahn et al., 1993, Nature Genetics 3(4):283–91.*
Cawthon et al., 1991, Genomics 9(3):446–60.*
Lehninger et al. Principles of Biochemistry, 2nd edition, 1993, p. 998.*
Hara et al., "Characterization of Cell Phenotype by a Novel cDNA Library Substraction System: Expression of CD8α in a Mast Cell–Derived Interleukin–4–Dependent Cell Line," *Blood* 84(1):189–199, 1994.

Lee et al., "Postive Selection of Candidate Tumor–Suppressor Genes by Subtractive Hybridization," *Proc. Natl. Acad. Sci. USA* 88:2825–2829, 1991.
Matsubara and Okubo, Genbank Sequence Database, Accession No. T21968, Oct. 25, 1999.
National Cancer Institute, Cancer Genome Anatomy Project, Genbank Sequence Database, Accession No. AA552419, Sep. 5, 1997.
National Cancer Institute, Cancer Genome Anatomy Project, Genbank Sequence Database, Accession No. AA610465, Oct. 30, 1997.
National Cancer Institute, Cancer Genome Anatomy Project, Genbank Sequence Database, Accession No. AA971201, May 20, 1998.
Neame and Boynton, Genbank Seqeunce Database, Accession No. AAC18614, Jun. 3, 1998.
Neame, Genbank Sequence Database, Accession No. U22298, Jun. 3, 1998.
Paul, *Fundamental Immunology*, $3^{rd}$ ed., Raven Press, New York, NY, 1993, pp. 243–247.
Porter–Jordan and Lippman, "Overview of the Biological Marker of Breast Cancer," *Hematology/Oncology Clinics of North America* 8(1):73–100, 1994.
Rieger et al, *Glossary of Genetics and Cytogenetics: Classical and Molecular*, $4^{th}$ ed., Springer–Verlag, New York, NY, 1976, pp. 17–18.
Ruddon, *Cancer Biology*, $3^{rd}$ ed., Oxford Unversity Press, New York, NY, 1995, p. 86.
Sager, "Tumor Suppressor Genes: The Puzzle and the Promise," *Science* 246:1406–1412, 1989.
Schweinfest and Papas, "Subtraction Hybridization: An Approach to the Isolation of Genes Differentially Expressed in Cancer and Other Biological Systems (Review)," *International Journal of Oncology* 1:499–506, 1992.

* cited by examiner

Primary Examiner—Anthony C. Caputa
Assistant Examiner—Gary B. Nickol
(74) Attorney, Agent, or Firm—Seed Intellectual Property Law Group PLLC

(57) ABSTRACT

Compounds and methods for the diagnosis of breast cancer are provided. The inventive compounds include polypeptides containing at least a portion of a breast tumor protein. The inventive polypeptides may be used to generate antibodies useful for the diagnosis and monitoring of breast cancer. Nucleic acid sequences for preparing probes, primers, and polypeptides are also provided.

8 Claims, No Drawings

SEQUENCE LISTING

```
<160> NUMBER OF SEQ ID NOS: 67

<210> SEQ ID NO 1
<211> LENGTH: 402
<212> TYPE: DNA
<213> ORGANISM: Homo sapiens
<220> FEATURE:
<221> NAME/KEY: modified_base
<222> LOCATION: (70)
<223> OTHER INFORMATION: Wherein n is a, c, g or t
<220> FEATURE:
<221> NAME/KEY: modified_base
<222> LOCATION: (80)
<223> OTHER INFORMATION: Wherein n is a, c, g or t
<220> FEATURE:
<221> NAME/KEY: modified_base
<222> LOCATION: (81)
<223> OTHER INFORMATION: Wherein n is a, c, g or t
<220> FEATURE:
<221> NAME/KEY: modified_base
<222> LOCATION: (166)
<223> OTHER INFORMATION: Wherein n is a, c, g or t
<220> FEATURE:
<221> NAME/KEY: modified_base
<222> LOCATION: (197)
<223> OTHER INFORMATION: Wherein n is a, c, g or t
<220> FEATURE:
<221> NAME/KEY: modified_base
<222> LOCATION: (213)
<223> OTHER INFORMATION: Wherein n is a, c, g or t
<220> FEATURE:
<221> NAME/KEY: modified_base
<222> LOCATION: (245)
<223> OTHER INFORMATION: Wherein n is a, c, g or t
<220> FEATURE:
<221> NAME/KEY: modified_base
<222> LOCATION: (265)
<223> OTHER INFORMATION: Wherein n is a, c, g or t
<220> FEATURE:
<221> NAME/KEY: modified_base
<222> LOCATION: (268)
<223> OTHER INFORMATION: Wherein n is a, c, g or t
<220> FEATURE:
<221> NAME/KEY: modified_base
<222> LOCATION: (277)
<223> OTHER INFORMATION: Wherein n is a, c, g or t
<220> FEATURE:
<221> NAME/KEY: modified_base
<222> LOCATION: (303)
<223> OTHER INFORMATION: Wherein n is a, c, g or t
<220> FEATURE:
```

<221> NAME/KEY: modified_base
<222> LOCATION: (309)
<223> OTHER INFORMATION: Wherein n is a, c, g or t
<220> FEATURE:
<221> NAME/KEY: modified_base
<222> LOCATION: (318)
<223> OTHER INFORMATION: Wherein n is a, c, g or t
<220> FEATURE:
<221> NAME/KEY: modified_base
<222> LOCATION: (342)
<223> OTHER INFORMATION: Wherein n is a, c, g or t
<220> FEATURE:
<221> NAME/KEY: modified_base
<222> LOCATION: (345)
<223> OTHER INFORMATION: Wherein n is a, c, g or t
<220> FEATURE:
<221> NAME/KEY: modified_base
<222> LOCATION: (361)
<223> OTHER INFORMATION: Wherein n is a, c, g or t
<220> FEATURE:
<221> NAME/KEY: modified_base
<222> LOCATION: (366)
<223> OTHER INFORMATION: Wherein n is a, c, g or t
<220> FEATURE:
<221> NAME/KEY: modified_base
<222> LOCATION: (369)
<223> OTHER INFORMATION: Wherein n is a, c, g or t

<400> SEQUENCE: 1

```
tttttttttt ttttaggag aactgaatca aacagatttt attcaacttt ttagatgagg      60
aaaacaaatn atacgaaatn ngtcataaga aatgctttct tataccacta tctcaaacca    120
ctttcaatat tttacaaaat gctcacgcag caaatatgaa aagctncaac acttcccttt    180
gttaacttgc tgcaatnaat gcaacttttaa canacataca aatttcttct gtatcttaaa   240
agttnaatta ctaattttaa tgatnttnct caagatnttt attcatatac ttttaatgac   300
tcnttgccna tacatacnta ttttctttac tttttttta cnatnggcca acagctttca   360
ngcagnccnc aaaaatctta ccggttaatt acacggggtt gt                       402
```

<210> SEQ ID NO 2
<211> LENGTH: 424
<212> TYPE: DNA
<213> ORGANISM: Homo sapiens
<220> FEATURE:
<221> NAME/KEY: modified_base
<222> LOCATION: (47)
<223> OTHER INFORMATION: Wherein n is a, c, g or t
<220> FEATURE:
<221> NAME/KEY: modified_base
<222> LOCATION: (103)
<223> OTHER INFORMATION: Wherein n is a, c, g or t
<220> FEATURE:
<221> NAME/KEY: modified_base
<222> LOCATION: (121)
<223> OTHER INFORMATION: Wherein n is a, c, g or t
<220> FEATURE:
<221> NAME/KEY: modified_base
<222> LOCATION: (133)
<223> OTHER INFORMATION: Wherein n is a, c, g or t
<220> FEATURE:
<221> NAME/KEY: modified_base
<222> LOCATION: (151)
<223> OTHER INFORMATION: Wherein n is a, c, g or t
<220> FEATURE:
<221> NAME/KEY: modified_base
<222> LOCATION: (152)
<223> OTHER INFORMATION: Wherein n is a, c, g or t
<220> FEATURE:
<221> NAME/KEY: modified_base
<222> LOCATION: (156)
<223> OTHER INFORMATION: Wherein n is a, c, g or t
<220> FEATURE:
<221> NAME/KEY: modified_base
<222> LOCATION: (174)
<223> OTHER INFORMATION: Wherein n is a, c, g or t
<220> FEATURE:
<221> NAME/KEY: modified_base
<222> LOCATION: (195)
<223> OTHER INFORMATION: Wherein n is a, c, g or t
<220> FEATURE:
<221> NAME/KEY: modified_base
<222> LOCATION: (222)
<223> OTHER INFORMATION: Wherein n is a, c, g or t
<220> FEATURE:
<221> NAME/KEY: modified_base
<222> LOCATION: (247)
<223> OTHER INFORMATION: Wherein n is a, c, g or t
<220> FEATURE:
<221> NAME/KEY: modified_base
<222> LOCATION: (262)
<223> OTHER INFORMATION: Wherein n is a, c, g or t
<220> FEATURE:
<221> NAME/KEY: modified_base
<222> LOCATION: (268)
<223> OTHER INFORMATION: Wherein n is a, c, g or t
<220> FEATURE:
<221> NAME/KEY: modified_base
<222> LOCATION: (273)
<223> OTHER INFORMATION: Wherein n is a, c, g or t
<220> FEATURE:
<221> NAME/KEY: modified_base
<222> LOCATION: (291)
<223> OTHER INFORMATION: Wherein n is a, c, g or t
<220> FEATURE:
<221> NAME/KEY: modified_base
<222> LOCATION: (293)
<223> OTHER INFORMATION: Wherein n is a, c, g or t
<220> FEATURE:
<221> NAME/KEY: modified_base
<222> LOCATION: (304)
<223> OTHER INFORMATION: Wherein n is a, c, g or t
<220> FEATURE:
<221> NAME/KEY: modified_base
<222> LOCATION: (315)
<223> OTHER INFORMATION: Wherein n is a, c, g or t
<220> FEATURE:
<221> NAME/KEY: modified_base
<222> LOCATION: (342)
<223> OTHER INFORMATION: Wherein n is a, c, g or t
<220> FEATURE:
<221> NAME/KEY: modified_base
<222> LOCATION: (352)
<223> OTHER INFORMATION: Wherein n is a, c, g or t
<220> FEATURE:
<221> NAME/KEY: modified_base
<222> LOCATION: (391)
<223> OTHER INFORMATION: Wherein n is a, c, g or t
<220> FEATURE:
<221> NAME/KEY: modified_base
<222> LOCATION: (393)
<223> OTHER INFORMATION: Wherein n is a, c, g or t

<400> SEQUENCE: 2

```
tttttttttt tttttttaaag gtacacattt cttttttcatt ctgtttnatg cagcaaataa     60
ttcgttggca tcttctctgt gatgggcagc ttgctaaaat tanactcagg cccccttagct    120
ncatttccaa ctnagcccac gctttcaacc nngccnaaca agaaaatca gttngggtta     180
aattctttgc tgganacaaa gaactacatt cctttgtaaa tnatgctttg tttgctctgt    240
gcaaacncag attgaaggga anaagganac ttntggggac ggaaacaact ngnagaagca    300
gganccgccc agggncattt cctcaccatg cttaatcttg cnctcacttg cnggcacca     360
ttaaacttgg tgcaaaaggc gcaattggtg nanggaaccc cacaccttcc ttaaaaagca    420
gggc                                                                  424
```

<210> SEQ ID NO 3

```
<211> LENGTH: 421
<212> TYPE: DNA
<213> ORGANISM: Homo sapiens
<220> FEATURE:
<221> NAME/KEY: modified_base
<222> LOCATION: (56)
<223> OTHER INFORMATION: Wherein n is a, c, g or t
<220> FEATURE:
<221> NAME/KEY: modified_base
<222> LOCATION: (64)
<223> OTHER INFORMATION: Wherein n is a, c, g or t
<220> FEATURE:
<221> NAME/KEY: modified_base
<222> LOCATION: (81)
<223> OTHER INFORMATION: Wherein n is a, c, g or t
<220> FEATURE:
<221> NAME/KEY: modified_base
<222> LOCATION: (95)
<223> OTHER INFORMATION: Wherein n is a, c, g or t
<220> FEATURE:
<221> NAME/KEY: modified_base
<222> LOCATION: (119)
<223> OTHER INFORMATION: Wherein n is a, c, g or t
<220> FEATURE:
<221> NAME/KEY: modified_base
<222> LOCATION: (124)
<223> OTHER INFORMATION: Wherein n is a, c, g or t
<220> FEATURE:
<221> NAME/KEY: modified_base
<222> LOCATION: (145)
<223> OTHER INFORMATION: Wherein n is a, c, g or t
<220> FEATURE:
<221> NAME/KEY: modified_base
<222> LOCATION: (168)
<223> OTHER INFORMATION: Wherein n is a, c, g or t
<220> FEATURE:
<221> NAME/KEY: modified_base
<222> LOCATION: (178)
<223> OTHER INFORMATION: Wherein n is a, c, g or t
<220> FEATURE:
<221> NAME/KEY: modified_base
<222> LOCATION: (183)
<223> OTHER INFORMATION: Wherein n is a, c, g or t
<220> FEATURE:
<221> NAME/KEY: modified_base
<222> LOCATION: (194)
<223> OTHER INFORMATION: Wherein n is a, c, g or t
<220> FEATURE:
<221> NAME/KEY: modified_base
<222> LOCATION: (210)
<223> OTHER INFORMATION: Wherein n is a, c, g or t
<220> FEATURE:
<221> NAME/KEY: modified_base
<222> LOCATION: (228)
<223> OTHER INFORMATION: Wherein n is a, c, g or t
<220> FEATURE:
<221> NAME/KEY: modified_base
<222> LOCATION: (237)
<223> OTHER INFORMATION: Wherein n is a, c, g or t
<220> FEATURE:
<221> NAME/KEY: modified_base
<222> LOCATION: (240)
<223> OTHER INFORMATION: Wherein n is a, c, g or t
<220> FEATURE:
<221> NAME/KEY: modified_base
<222> LOCATION: (257)
<223> OTHER INFORMATION: Wherein n is a, c, g or t
<220> FEATURE:
<221> NAME/KEY: modified_base
<222> LOCATION: (274)
<223> OTHER INFORMATION: Wherein n is a, c, g or t
<220> FEATURE:
<221> NAME/KEY: modified_base
<222> LOCATION: (279)
<223> OTHER INFORMATION: Wherein n is a, c, g or t
<220> FEATURE:
<221> NAME/KEY: modified_base
<222> LOCATION: (291)
<223> OTHER INFORMATION: Wherein n is a, c, g or t
```

<220> FEATURE:
<221> NAME/KEY: modified_base
<222> LOCATION: (300)
<223> OTHER INFORMATION: Wherein n is a, c, g or t
<220> FEATURE:
<221> NAME/KEY: modified_base
<222> LOCATION: (313)
<223> OTHER INFORMATION: Wherein n is a, c, g or t
<220> FEATURE:
<221> NAME/KEY: modified_base
<222> LOCATION: (323)
<223> OTHER INFORMATION: Wherein n is a, c, g or t
<220> FEATURE:
<221> NAME/KEY: modified_base
<222> LOCATION: (345)
<223> OTHER INFORMATION: Wherein n is a, c, g or t
<220> FEATURE:
<221> NAME/KEY: modified_base
<222> LOCATION: (353)
<223> OTHER INFORMATION: Wherein n is a, c, g or t
<220> FEATURE:
<221> NAME/KEY: modified_base
<222> LOCATION: (355)
<223> OTHER INFORMATION: Wherein n is a, c, g or t
<220> FEATURE:
<221> NAME/KEY: modified_base
<222> LOCATION: (377)
<223> OTHER INFORMATION: Wherein n is a, c, g or t
<220> FEATURE:
<221> NAME/KEY: modified_base
<222> LOCATION: (379)
<223> OTHER INFORMATION: Wherein n is a, c, g or t
<220> FEATURE:
<221> NAME/KEY: modified_base
<222> LOCATION: (385)
<223> OTHER INFORMATION: Wherein n is a, c, g or t
<220> FEATURE:
<221> NAME/KEY: modified_base
<222> LOCATION: (392)
<223> OTHER INFORMATION: Wherein n is a, c, g or t
<220> FEATURE:
<221> NAME/KEY: modified_base
<222> LOCATION: (405)
<223> OTHER INFORMATION: Wherein n is a, c, g or t
<220> FEATURE:
<221> NAME/KEY: modified_base
<222> LOCATION: (407)
<223> OTHER INFORMATION: Wherein n is a, c, g or t
<220> FEATURE:
<221> NAME/KEY: modified_base
<222> LOCATION: (411)
<223> OTHER INFORMATION: Wherein n is a, c, g or t

<400> SEQUENCE: 3
tttttttttt ttttcccaa tttaaaaaag ccttttcat acttcaatta caccanactt    60
aatnatttca tgagtaaatc ngacattatt atttnaaaat ttgcatattt aaaatttgna   120
tcanttactt ccagactgtt tgcanaatga agggaggatc actcaagngc tgatctcnca   180
ctntctgcag tctnctgtcc tgtgcccggn ctaatggatc gacactanat ggacagntcn   240
cagatcttcc gttcttntcc cttccccaat ttcncaccnc tccccttctt nccggatcn   300 tttggggaca tgntaatttt gcnatcctta aaccctgccc gccanggtc ccnanctcag   360 gggtggttaa tgttcgncng gcttnttgac cnctgcgcc ctttnantcc naacccaag   420 c                                                                  421

<210> SEQ ID NO 4
<211> LENGTH: 423
<212> TYPE: DNA
<213> ORGANISM: Homo sapiens
<220> FEATURE:
<221> NAME/KEY: modified_base
<222> LOCATION: (24)

-continued

```
<223> OTHER INFORMATION: Wherein n is a, c, g or t
<220> FEATURE:
<221> NAME/KEY: modified_base
<222> LOCATION: (26)
<223> OTHER INFORMATION: Wherein n is a, c, g or t
<220> FEATURE:
<221> NAME/KEY: modified_base
<222> LOCATION: (27)
<223> OTHER INFORMATION: Wherein n is a, c, g or t
<220> FEATURE:
<221> NAME/KEY: modified_base
<222> LOCATION: (33)
<223> OTHER INFORMATION: Wherein n is a, c, g or t
<220> FEATURE:
<221> NAME/KEY: modified_base
<222> LOCATION: (34)
<223> OTHER INFORMATION: Wherein n is a, c, g or t
<220> FEATURE:
<221> NAME/KEY: modified_base
<222> LOCATION: (37)
<223> OTHER INFORMATION: Wherein n is a, c, g or t
<220> FEATURE:
<221> NAME/KEY: modified_base
<222> LOCATION: (57)
<223> OTHER INFORMATION: Wherein n is a, c, g or t
<220> FEATURE:
<221> NAME/KEY: modified_base
<222> LOCATION: (59)
<223> OTHER INFORMATION: Wherein n is a, c, g or t
<220> FEATURE:
<221> NAME/KEY: modified_base
<222> LOCATION: (73)
<223> OTHER INFORMATION: Wherein n is a, c, g or t
<220> FEATURE:
<221> NAME/KEY: modified_base
<222> LOCATION: (78)
<223> OTHER INFORMATION: Wherein n is a, c, g or t
<220> FEATURE:
<221> NAME/KEY: modified_base
<222> LOCATION: (84)
<223> OTHER INFORMATION: Wherein n is a, c, g or t
<220> FEATURE:
<221> NAME/KEY: modified_base
<222> LOCATION: (102)
<223> OTHER INFORMATION: Wherein n is a, c, g or t
<220> FEATURE:
<221> NAME/KEY: modified_base
<222> LOCATION: (131)
<223> OTHER INFORMATION: Wherein n is a, c, g or t
<220> FEATURE:
<221> NAME/KEY: modified_base
<222> LOCATION: (134)
<223> OTHER INFORMATION: Wherein n is a, c, g or t
<220> FEATURE:
<221> NAME/KEY: modified_base
<222> LOCATION: (138)
<223> OTHER INFORMATION: Wherein n is a, c, g or t
<220> FEATURE:
<221> NAME/KEY: modified_base
<222> LOCATION: (145)
<223> OTHER INFORMATION: Wherein n is a, c, g or t
<220> FEATURE:
<221> NAME/KEY: modified_base
<222> LOCATION: (157)
<223> OTHER INFORMATION: Wherein n is a, c, g or t
<220> FEATURE:
<221> NAME/KEY: modified_base
<222> LOCATION: (167)
<223> OTHER INFORMATION: Wherein n is a, c, g or t
<220> FEATURE:
<221> NAME/KEY: modified_base
<222> LOCATION: (171)
<223> OTHER INFORMATION: Wherein n is a, c, g or t
<220> FEATURE:
<221> NAME/KEY: modified_base
<222> LOCATION: (189)
<223> OTHER INFORMATION: Wherein n is a, c, g or t
<220> FEATURE:
<221> NAME/KEY: modified_base
```

-continued

```
<222> LOCATION: (206)
<223> OTHER INFORMATION: Wherein n is a, c, g or t
<220> FEATURE:
<221> NAME/KEY: modified_base
<222> LOCATION: (221)
<223> OTHER INFORMATION: Wherein n is a, c, g or t
<220> FEATURE:
<221> NAME/KEY: modified_base
<222> LOCATION: (239)
<223> OTHER INFORMATION: Wherein n is a, c, g or t
<220> FEATURE:
<221> NAME/KEY: modified_base
<222> LOCATION: (246)
<223> OTHER INFORMATION: Wherein n is a, c, g or t
<220> FEATURE:
<221> NAME/KEY: modified_base
<222> LOCATION: (256)
<223> OTHER INFORMATION: Wherein n is a, c, g or t
<220> FEATURE:
<221> NAME/KEY: modified_base
<222> LOCATION: (259)
<223> OTHER INFORMATION: Wherein n is a, c, g or t
<220> FEATURE:
<221> NAME/KEY: modified_base
<222> LOCATION: (288)
<223> OTHER INFORMATION: Wherein n is a, c, g or t
<220> FEATURE:
<221> NAME/KEY: modified_base
<222> LOCATION: (308)
<223> OTHER INFORMATION: Wherein n is a, c, g or t
<220> FEATURE:
<221> NAME/KEY: modified_base
<222> LOCATION: (311)
<223> OTHER INFORMATION: Wherein n is a, c, g or t
<220> FEATURE:
<221> NAME/KEY: modified_base
<222> LOCATION: (325)
<223> OTHER INFORMATION: Wherein n is a, c, g or t
<220> FEATURE:
<221> NAME/KEY: modified_base
<222> LOCATION: (334)
<223> OTHER INFORMATION: Wherein n is a, c, g or t
<220> FEATURE:
<221> NAME/KEY: modified_base
<222> LOCATION: (342)
<223> OTHER INFORMATION: Wherein n is a, c, g or t
<220> FEATURE:
<221> NAME/KEY: modified_base
<222> LOCATION: (344)
<223> OTHER INFORMATION: Wherein n is a, c, g or t
<220> FEATURE:
<221> NAME/KEY: modified_base
<222> LOCATION: (345)
<223> OTHER INFORMATION: Wherein n is a, c, g or t
<220> FEATURE:
<221> NAME/KEY: modified_base
<222> LOCATION: (351)
<223> OTHER INFORMATION: Wherein n is a, c, g or t
<220> FEATURE:
<221> NAME/KEY: modified_base
<222> LOCATION: (353)
<223> OTHER INFORMATION: Wherein n is a, c, g or t
<220> FEATURE:
<221> NAME/KEY: modified_base
<222> LOCATION: (359)
<223> OTHER INFORMATION: Wherein n is a, c, g or t
<220> FEATURE:
<221> NAME/KEY: modified_base
<222> LOCATION: (360)
<223> OTHER INFORMATION: Wherein n is a, c, g or t
<220> FEATURE:
<221> NAME/KEY: modified_base
<222> LOCATION: (364)
<223> OTHER INFORMATION: Wherein n is a, c, g or t
<220> FEATURE:
<221> NAME/KEY: modified_base
<222> LOCATION: (370)
<223> OTHER INFORMATION: Wherein n is a, c, g or t
<220> FEATURE:
```

<220> FEATURE:
<221> NAME/KEY: modified_base
<222> LOCATION: (376)
<223> OTHER INFORMATION: Wherein n is a, c, g or t
<220> FEATURE:
<221> NAME/KEY: modified_base
<222> LOCATION: (379)
<223> OTHER INFORMATION: Wherein n is a, c, g or t
<220> FEATURE:
<221> NAME/KEY: modified_base
<222> LOCATION: (400)
<223> OTHER INFORMATION: Wherein n is a, c, g or t
<220> FEATURE:
<221> NAME/KEY: modified_base
<222> LOCATION: (403)
<223> OTHER INFORMATION: Wherein n is a, c, g or t
<220> FEATURE:
<221> NAME/KEY: modified_base
<222> LOCATION: (411)
<223> OTHER INFORMATION: Wherein n is a, c, g or t

<400> SEQUENCE: 4

```
tttttttatt ttttttcta tttntnnntat ttnntgnggt tcctgtgtgt aattagnang      60
tgtgtatgcg tangtacnta tgtntgcata tttaacctgt tnccttcca tttttaaaat     120
aaaatctcaa natngtantt ggttnatggg agtaaanaga gactatngat naattttaac    180
atggacacng tgaaatgtag ccgctnatca ntttaaaact tcatttgaa ggcctttnc      240
cctccnaata aaaatnccng gccctactgg gttaagcaac attgcatntc taaagaaacc    300
acatgcanac nagttaaacc tgtgnactgg tcangcaaac cnanntggaa nanaagggnn    360
ttcncccan ggacantcng aattttttta acaaattacn atncccccc nggggagcc       420
tgt                                                                  423
```

<210> SEQ ID NO 5
<211> LENGTH: 355
<212> TYPE: DNA
<213> ORGANISM: Homo sapiens
<220> FEATURE:
<221> NAME/KEY: modified_base
<222> LOCATION: (11)
<223> OTHER INFORMATION: Wherein n is a, c, g or t
<220> FEATURE:
<221> NAME/KEY: modified_base
<222> LOCATION: (152)
<223> OTHER INFORMATION: Wherein n is a, c, g or t
<220> FEATURE:
<221> NAME/KEY: modified_base
<222> LOCATION: (218)
<223> OTHER INFORMATION: Wherein n is a, c, g or t
<220> FEATURE:
<221> NAME/KEY: modified_base
<222> LOCATION: (220)
<223> OTHER INFORMATION: Wherein n is a, c, g or t
<220> FEATURE:
<221> NAME/KEY: modified_base
<222> LOCATION: (238)
<223> OTHER INFORMATION: Wherein n is a, c, g or t
<220> FEATURE:
<221> NAME/KEY: modified_base
<222> LOCATION: (250)
<223> OTHER INFORMATION: Wherein n is a, c, g or t
<220> FEATURE:
<221> NAME/KEY: modified_base
<222> LOCATION: (253)
<223> OTHER INFORMATION: Wherein n is a, c, g or t
<220> FEATURE:
<221> NAME/KEY: modified_base
<222> LOCATION: (260)
<223> OTHER INFORMATION: Wherein n is a, c, g or t
<220> FEATURE:
<221> NAME/KEY: modified_base
<222> LOCATION: (299)
<223> OTHER INFORMATION: Wherein n is a, c, g or t
<220> FEATURE:
<221> NAME/KEY: modified_base
<222> LOCATION: (339)
<223> OTHER INFORMATION: Wherein n is a, c, g or t

<400> SEQUENCE: 5

| | | | | | |
|---|---|---|---|---|---|
| acgaccacct | natttcgtat | ctttcaactc | ttttcgaccg | gacctcttat | tcggaagcgt         60 |
| tccaggaaga | caggtctcaa | cttagggatc | agatcacgtt | atcaacgctc | tgggatcgct        120 |
| gcaacctggc | acttcaagga | agtgcaccga | tnacgtctag | accggccaac | acagatctag        180 |
| aggtggccaa | ctgatcactg | taggagctga | ctggcaanan | tcaaccgggc | cccaaccnag        240 |
| agtgaccaan | acnaccattn | aggatcaccc | acaggcactc | ctcgtcctag | ggccaaccna        300 |
| ccaaacggct | ggccaatggg | ggggtttaat | atttggttna | aaaattgatt | ttaaa             355 |

<210> SEQ ID NO 6
<211> LENGTH: 423
<212> TYPE: DNA
<213> ORGANISM: Homo sapiens
<220> FEATURE:
<221> NAME/KEY: modified_base
<222> LOCATION: (40)
<223> OTHER INFORMATION: Wherein n is a, c, g or t
<220> FEATURE:
<221> NAME/KEY: modified_base
<222> LOCATION: (42)
<223> OTHER INFORMATION: Wherein n is a, c, g or t
<220> FEATURE:
<221> NAME/KEY: modified_base
<222> LOCATION: (49)
<223> OTHER INFORMATION: Wherein n is a, c, g or t
<220> FEATURE:
<221> NAME/KEY: modified_base
<222> LOCATION: (80)
<223> OTHER INFORMATION: Wherein n is a, c, g or t
<220> FEATURE:
<221> NAME/KEY: modified_base
<222> LOCATION: (112)
<223> OTHER INFORMATION: Wherein n is a, c, g or t
<220> FEATURE:
<221> NAME/KEY: modified_base
<222> LOCATION: (140)
<223> OTHER INFORMATION: Wherein n is a, c, g or t
<220> FEATURE:
<221> NAME/KEY: modified_base
<222> LOCATION: (149)
<223> OTHER INFORMATION: Wherein n is a, c, g or t
<220> FEATURE:
<221> NAME/KEY: modified_base
<222> LOCATION: (170)
<223> OTHER INFORMATION: Wherein n is a, c, g or t
<220> FEATURE:
<221> NAME/KEY: modified_base
<222> LOCATION: (203)
<223> OTHER INFORMATION: Wherein n is a, c, g or t
<220> FEATURE:
<221> NAME/KEY: modified_base
<222> LOCATION: (221)
<223> OTHER INFORMATION: Wherein n is a, c, g or t
<220> FEATURE:
<221> NAME/KEY: modified_base
<222> LOCATION: (224)
<223> OTHER INFORMATION: Wherein n is a, c, g or t
<220> FEATURE:
<221> NAME/KEY: modified_base
<222> LOCATION: (241)
<223> OTHER INFORMATION: Wherein n is a, c, g or t
<220> FEATURE:
<221> NAME/KEY: modified_base
<222> LOCATION: (305)
<223> OTHER INFORMATION: Wherein n is a, c, g or t
<220> FEATURE:
<221> NAME/KEY: modified_base
<222> LOCATION: (312)

<223> OTHER INFORMATION: Wherein n is a, c, g or t
<220> FEATURE:
<221> NAME/KEY: modified_base
<222> LOCATION: (317)
<223> OTHER INFORMATION: Wherein n is a, c, g or t
<220> FEATURE:
<221> NAME/KEY: modified_base
<222> LOCATION: (326)
<223> OTHER INFORMATION: Wherein n is a, c, g or t
<220> FEATURE:
<221> NAME/KEY: modified_base
<222> LOCATION: (345)
<223> OTHER INFORMATION: Wherein n is a, c, g or t
<220> FEATURE:
<221> NAME/KEY: modified_base
<222> LOCATION: (381)
<223> OTHER INFORMATION: Wherein n is a, c, g or t
<220> FEATURE:
<221> NAME/KEY: modified_base
<222> LOCATION: (388)
<223> OTHER INFORMATION: Wherein n is a, c, g or t
<220> FEATURE:
<221> NAME/KEY: modified_base
<222> LOCATION: (393)
<223> OTHER INFORMATION: Wherein n is a, c, g or t
<220> FEATURE:
<221> NAME/KEY: modified_base
<222> LOCATION: (401)
<223> OTHER INFORMATION: Wherein n is a, c, g or t

<400> SEQUENCE: 6

```
ttttttttttt tttttggaca ggaagtaaaa tttattggtn antattaana gggggggcagc    60 acattggaag ccctcatgan tgcagggccc gccacttgtc cagagggcca cnattgggga     120
tgtacttaac cccacagccn tctgggatna gccgcttttc agccaccatn tcttcaaatt    180
catcagcatt aaacttggta aanccccact tctttaagat ntgnatcttc tggcggccag    240
naaacttgaa cttggccctg cgcagggcct caatcacatg ctccttgttc tgcagcttgg    300
tgcgnaagga cntaatnact tggccnatgt gaaccctggc cacantgccc tggggctttc    360
caaaggcacc tcgcaagcct ntttggance tgnccgcccc ngcacaggga caacatcttg    420
ttt                                                                   423
```

<210> SEQ ID NO 7
<211> LENGTH: 410
<212> TYPE: DNA
<213> ORGANISM: Homo sapien
<220> FEATURE:
<221> NAME/KEY: modified_base
<222> LOCATION: (36)
<223> OTHER INFORMATION: Wherein n is a, c, g or t
<220> FEATURE:
<221> NAME/KEY: modified_base
<222> LOCATION: (74)
<223> OTHER INFORMATION: Wherein n is a, c, g or t
<220> FEATURE:
<221> NAME/KEY: modified_base
<222> LOCATION: (92)
<223> OTHER INFORMATION: Wherein n is a, c, g or t
<220> FEATURE:
<221> NAME/KEY: modified_base
<222> LOCATION: (97)
<223> OTHER INFORMATION: Wherein n is a, c, g or t
<220> FEATURE:
<221> NAME/KEY: modified_base
<222> LOCATION: (112)
<223> OTHER INFORMATION: Wherein n is a, c, g or t
<220> FEATURE:
<221> NAME/KEY: modified_base
<222> LOCATION: (121)
<223> OTHER INFORMATION: Wherein n is a, c, g or t
<220> FEATURE:
<221> NAME/KEY: modified_base
<222> LOCATION: (123)
<223> OTHER INFORMATION: Wherein n is a, c, g or t
<220> FEATURE:
<221> NAME/KEY: modified_base
<222> LOCATION: (149)
<223> OTHER INFORMATION: Wherein n is a, c, g or t
<220> FEATURE:
<221> NAME/KEY: modified_base
<222> LOCATION: (154)
<223> OTHER INFORMATION: Wherein n is a, c, g or t
<220> FEATURE:
<221> NAME/KEY: modified_base
<222> LOCATION: (256)
<223> OTHER INFORMATION: Wherein n is a, c, g or t
<220> FEATURE:
<221> NAME/KEY: modified_base
<222> LOCATION: (262)
<223> OTHER INFORMATION: Wherein n is a, c, g or t
<220> FEATURE:
<221> NAME/KEY: modified_base
<222> LOCATION: (271)
<223> OTHER INFORMATION: Wherein n is a, c, g or t
<220> FEATURE:
<221> NAME/KEY: modified_base
<222> LOCATION: (287)
<223> OTHER INFORMATION: Wherein n is a, c, g or t
<220> FEATURE:
<221> NAME/KEY: modified_base
<222> LOCATION: (326)
<223> OTHER INFORMATION: Wherein n is a, c, g or t
<220> FEATURE:
<221> NAME/KEY: modified_base
<222> LOCATION: (327)
<223> OTHER INFORMATION: Wherein n is a, c, g or t
<220> FEATURE:
<221> NAME/KEY: modified_base
<222> LOCATION: (366)
<223> OTHER INFORMATION: Wherein n is a, c, g or t
<220> FEATURE:
<221> NAME/KEY: modified_base
<222> LOCATION: (367)
<223> OTHER INFORMATION: Wherein n is a, c, g or t
<220> FEATURE:
<221> NAME/KEY: modified_base
<222> LOCATION: (375)
<223> OTHER INFORMATION: Wherein n is a, c, g or t
<220> FEATURE:
<221> NAME/KEY: modified_base
<222> LOCATION: (399)
<223> OTHER INFORMATION: Wherein n is a, c, g or t

<400> SEQUENCE: 7

```
ttcgcactgg ctaaaacaaa ccgccttgca aagttngaaa aatttatcaa tggaccaaat      60
aatgctcata tccnacaagt tggtgaccgt tnttatnata aaaaaatgta tnatgctcct     120
nanttgttgt acaataatgt tccaatttng gacnttcggc atctaccctg gttcacctgg    180
gtaaatatca ggcagctttt gatggggcta ggaaagctaa cagtactcga acatgggaaa    240
gaggtctgct tcgccngtgt anatgggaaa naattccgtc ttgctcngat ttgtggactt    300
catattgttg tacatgcaga tgaatnngaa gaacttgtca actactatca ggatcgtggc    360
tttttnnaaa agctnatcac catgttggaa gcggcactng gacttgagcg               410
```

<210> SEQ ID NO 8
<211> LENGTH: 274
<212> TYPE: DNA
<213> ORGANISM: Homo sapiens
<220> FEATURE:
<221> NAME/KEY: modified_base
<222> LOCATION: (43)
<223> OTHER INFORMATION: Wherein n is a, c, g or t
<220> FEATURE:
<221> NAME/KEY: modified_base
<222> LOCATION: (48)

<223> OTHER INFORMATION: Wherein n is a, c, g or t
<220> FEATURE:
<221> NAME/KEY: modified_base
<222> LOCATION: (110)
<223> OTHER INFORMATION: Wherein n is a, c, g or t
<220> FEATURE:
<221> NAME/KEY: modified_base
<222> LOCATION: (113)
<223> OTHER INFORMATION: Wherein n is a, c, g or t
<220> FEATURE:
<221> NAME/KEY: modified_base
<222> LOCATION: (131)
<223> OTHER INFORMATION: Wherein n is a, c, g or t
<220> FEATURE:
<221> NAME/KEY: modified_base
<222> LOCATION: (133)
<223> OTHER INFORMATION: Wherein n is a, c, g or t
<220> FEATURE:
<221> NAME/KEY: modified_base
<222> LOCATION: (172)
<223> OTHER INFORMATION: Wherein n is a, c, g or t
<220> FEATURE:
<221> NAME/KEY: modified_base
<222> LOCATION: (200)
<223> OTHER INFORMATION: Wherein n is a, c, g or t
<220> FEATURE:
<221> NAME/KEY: modified_base
<222> LOCATION: (202)
<223> OTHER INFORMATION: Wherein n is a, c, g or t
<220> FEATURE:
<221> NAME/KEY: modified_base
<222> LOCATION: (208)
<223> OTHER INFORMATION: Wherein n is a, c, g or t
<220> FEATURE:
<221> NAME/KEY: modified_base
<222> LOCATION: (217)
<223> OTHER INFORMATION: Wherein n is a, c, g or t
<220> FEATURE:
<221> NAME/KEY: modified_base
<222> LOCATION: (230)
<223> OTHER INFORMATION: Wherein n is a, c, g or t
<220> FEATURE:
<221> NAME/KEY: modified_base
<222> LOCATION: (235)
<223> OTHER INFORMATION: Wherein n is a, c, g or t
<220> FEATURE:
<221> NAME/KEY: modified_base
<222> LOCATION: (236)
<223> OTHER INFORMATION: Wherein n is a, c, g or t
<220> FEATURE:
<221> NAME/KEY: modified_base
<222> LOCATION: (245)
<223> OTHER INFORMATION: Wherein n is a, c, g or t
<220> FEATURE:
<221> NAME/KEY: modified_base
<222> LOCATION: (258)
<223> OTHER INFORMATION: Wherein n is a, c, g or t
<220> FEATURE:
<221> NAME/KEY: modified_base
<222> LOCATION: (262)
<223> OTHER INFORMATION: Wherein n is a, c, g or t
<220> FEATURE:
<221> NAME/KEY: modified_base
<222> LOCATION: (265)
<223> OTHER INFORMATION: Wherein n is a, c, g or t

<400> SEQUENCE: 8

```
tttttttttt ttttaggtc atacatattt tttattataa canatatntg tatatacata    60
taatatatgt gtatatatcc acgtgtgtgt gtgtgtatca aaaacaacan aantttagtg   120
atctatatct ntngctcaca tatgcatggg agataccagt aaaaaataag tnaatctcca  180
taatatgttt taaaactcan anaaatcnga gagactnaaa gaaaacgttn atcannatga  240
ttgtngataa tcttgaanaa tnacnaaaac atat                              274
```

```
<210> SEQ ID NO 9
<211> LENGTH: 322
<212> TYPE: DNA
<213> ORGANISM: Homo sapiens
<220> FEATURE:
<221> NAME/KEY: modified_base
<222> LOCATION: (33)
<223> OTHER INFORMATION: Wherein n is a, c, g or t
<220> FEATURE:
<221> NAME/KEY: modified_base
<222> LOCATION: (35)
<223> OTHER INFORMATION: Wherein n is a, c, g or t
<220> FEATURE:
<221> NAME/KEY: modified_base
<222> LOCATION: (109)
<223> OTHER INFORMATION: Wherein n is a, c, g or t
<220> FEATURE:
<221> NAME/KEY: modified_base
<222> LOCATION: (111)
<223> OTHER INFORMATION: Wherein n is a, c, g or t
<220> FEATURE:
<221> NAME/KEY: modified_base
<222> LOCATION: (136)
<223> OTHER INFORMATION: Wherein n is a, c, g or t
<220> FEATURE:
<221> NAME/KEY: modified_base
<222> LOCATION: (150)
<223> OTHER INFORMATION: Wherein n is a, c, g or t
<220> FEATURE:
<221> NAME/KEY: modified_base
<222> LOCATION: (164)
<223> OTHER INFORMATION: Wherein n is a, c, g or t
<220> FEATURE:
<221> NAME/KEY: modified_base
<222> LOCATION: (165)
<223> OTHER INFORMATION: Wherein n is a, c, g or t
<220> FEATURE:
<221> NAME/KEY: modified_base
<222> LOCATION: (174)
<223> OTHER INFORMATION: Wherein n is a, c, g or t
<220> FEATURE:
<221> NAME/KEY: modified_base
<222> LOCATION: (199)
<223> OTHER INFORMATION: Wherein n is a, c, g or t
<220> FEATURE:
<221> NAME/KEY: modified_base
<222> LOCATION: (205)
<223> OTHER INFORMATION: Wherein n is a, c, g or t
<220> FEATURE:
<221> NAME/KEY: modified_base
<222> LOCATION: (215)
<223> OTHER INFORMATION: Wherein n is a, c, g or t
<220> FEATURE:
<221> NAME/KEY: modified_base
<222> LOCATION: (222)
<223> OTHER INFORMATION: Wherein n is a, c, g or t
<220> FEATURE:
<221> NAME/KEY: modified_base
<222> LOCATION: (245)
<223> OTHER INFORMATION: Wherein n is a, c, g or t
<220> FEATURE:
<221> NAME/KEY: modified_base
<222> LOCATION: (259)
<223> OTHER INFORMATION: Wherein n is a, c, g or t
<220> FEATURE:
<221> NAME/KEY: modified_base
<222> LOCATION: (280)
<223> OTHER INFORMATION: Wherein n is a, c, g or t
<220> FEATURE:
<221> NAME/KEY: modified_base
<222> LOCATION: (299)
<223> OTHER INFORMATION: Wherein n is a, c, g or t
<220> FEATURE:
<221> NAME/KEY: modified_base
<222> LOCATION: (304)
<223> OTHER INFORMATION: Wherein n is a, c, g or t
<220> FEATURE:
<221> NAME/KEY: modified_base
<222> LOCATION: (305)
```

<223> OTHER INFORMATION: Wherein n is a, c, g or t
<220> FEATURE:
<221> NAME/KEY: modified_base
<222> LOCATION: (307)
<223> OTHER INFORMATION: Wherein n is a, c, g or t
<220> FEATURE:
<221> NAME/KEY: modified_base
<222> LOCATION: (319)
<223> OTHER INFORMATION: Wherein n is a, c, g or t

<400> SEQUENCE: 9
tttttttttt ttttgtgcct tattgcaccg gcnanaactt ctagcactat attaaactca      60
ataagagtga taagtgtgaa aatccttgcc ttctctttaa tcttaatgna naggcatctg     120
gtttttcacc attaantgta ataatggctn tatgtatttt tatnnatggt cttnatggag     180 ttaaaaagt tttcctctnt ccctngttat ctaanagttt tnatcaaaaa tgggtataat      240
atttngttca gtacttttnc ctgcacctat agatatgatn ctgttatttt ttcttcttng     300
cctnnanata tgatggatna ca                                              322

<210> SEQ ID NO 10
<211> LENGTH: 425
<212> TYPE: DNA
<213> ORGANISM: Homo sapiens
<220> FEATURE:
<221> NAME/KEY: modified_base
<222> LOCATION: (48)
<223> OTHER INFORMATION: Wherein n is a, c, g or t
<220> FEATURE:
<221> NAME/KEY: modified_base
<222> LOCATION: (85)
<223> OTHER INFORMATION: Wherein n is a, c, g or t
<220> FEATURE:
<221> NAME/KEY: modified_base
<222> LOCATION: (223)
<223> OTHER INFORMATION: Wherein n is a, c, g or t
<220> FEATURE:
<221> NAME/KEY: modified_base
<222> LOCATION: (226)
<223> OTHER INFORMATION: Wherein n is a, c, g or t
<220> FEATURE:
<221> NAME/KEY: modified_base
<222> LOCATION: (263)
<223> OTHER INFORMATION: Wherein n is a, c, g or t
<220> FEATURE:
<221> NAME/KEY: modified_base
<222> LOCATION: (272)
<223> OTHER INFORMATION: Wherein n is a, c, g or t
<220> FEATURE:
<221> NAME/KEY: modified_base
<222> LOCATION: (280)
<223> OTHER INFORMATION: Wherein n is a, c, g or t
<220> FEATURE:
<221> NAME/KEY: modified_base
<222> LOCATION: (285)
<223> OTHER INFORMATION: Wherein n is a, c, g or t
<220> FEATURE:
<221> NAME/KEY: modified_base
<222> LOCATION: (293)
<223> OTHER INFORMATION: Wherein n is a, c, g or t
<220> FEATURE:
<221> NAME/KEY: modified_base
<222> LOCATION: (296)
<223> OTHER INFORMATION: Wherein n is a, c, g or t
<220> FEATURE:
<221> NAME/KEY: modified_base
<222> LOCATION: (298)
<223> OTHER INFORMATION: Wherein n is a, c, g or t
<220> FEATURE:
<221> NAME/KEY: modified_base
<222> LOCATION: (308)
<223> OTHER INFORMATION: Wherein n is a, c, g or t
<220> FEATURE:
<221> NAME/KEY: modified_base
<222> LOCATION: (341)
<223> OTHER INFORMATION: Wherein n is a, c, g or t
<220> FEATURE:
<221> NAME/KEY: modified_base
<222> LOCATION: (354)
<223> OTHER INFORMATION: Wherein n is a, c, g or t
<220> FEATURE:
<221> NAME/KEY: modified_base
<222> LOCATION: (419)
<223> OTHER INFORMATION: Wherein n is a, c, g or t
<220> FEATURE:
<221> NAME/KEY: modified_base
<222> LOCATION: (425)
<223> OTHER INFORMATION: Wherein n is a, c, g or t

<400> SEQUENCE: 10 ttttttttt ttttattct gcagccatta aatgctgaac actagatnct tatttgtgga       60
ggtcacaaaa taagtacaga atatnacaca cgccctgccc ataaaagca cagctcccag     120 ttctatattt acaatatctc tggaattcca ccttcccttc taatttgact aatatttctg     180
cttctcaggc agcagcgcct tctggcaacc ataagaacca acntgnggac taggtcggtg     240
ggccaaggat caggaaacag aanaatggaa gnagcccccn tgacnctatt aanctntnaa     300
actatctnaa ctgctagttt tcaggcttta aatcatgtaa natacgtgtc cttnttgctg     360
caaccggaag catcctagat ggtacactct ctccaggtgc aggaaaaga tcccaaatng     420 caggn                                                                425

<210> SEQ ID NO 11
<211> LENGTH: 424
<212> TYPE: DNA
<213> ORGANISM: Homo sapiens
<220> FEATURE:
<221> NAME/KEY: modified_base
<222> LOCATION: (5)
<223> OTHER INFORMATION: Wherein n is a, c, g or t
<220> FEATURE:
<221> NAME/KEY: modified_base
<222> LOCATION: (9)
<223> OTHER INFORMATION: Wherein n is a, c, g or t
<220> FEATURE:
<221> NAME/KEY: modified_base
<222> LOCATION: (18)
<223> OTHER INFORMATION: Wherein n is a, c, g or t
<220> FEATURE:
<221> NAME/KEY: modified_base
<222> LOCATION: (21)
<223> OTHER INFORMATION: Wherein n is a, c, g or t
<220> FEATURE:
<221> NAME/KEY: modified_base
<222> LOCATION: (24)
<223> OTHER INFORMATION: Wherein n is a, c, g or t
<220> FEATURE:
<221> NAME/KEY: modified_base
<222> LOCATION: (25)
<223> OTHER INFORMATION: Wherein n is a, c, g or t
<220> FEATURE:
<221> NAME/KEY: modified_base
<222> LOCATION: (29)
<223> OTHER INFORMATION: Wherein n is a, c, g or t
<220> FEATURE:
<221> NAME/KEY: modified_base
<222> LOCATION: (30)
<223> OTHER INFORMATION: Wherein n is a, c, g or t
<220> FEATURE:
<221> NAME/KEY: modified_base
<222> LOCATION: (32)
<223> OTHER INFORMATION: Wherein n is a, c, g or t
<220> FEATURE:
<221> NAME/KEY: modified_base
<222> LOCATION: (38)
<223> OTHER INFORMATION: Wherein n is a, c, g or t
<220> FEATURE:

```
<221> NAME/KEY: modified_base
<222> LOCATION: (102)
<223> OTHER INFORMATION: Wherein n is a, c, g or t
<220> FEATURE:
<221> NAME/KEY: modified_base
<222> LOCATION: (166)
<223> OTHER INFORMATION: Wherein n is a, c, g or t
<220> FEATURE:
<221> NAME/KEY: modified_base
<222> LOCATION: (175)
<223> OTHER INFORMATION: Wherein n is a, c, g or t
<220> FEATURE:
<221> NAME/KEY: modified_base
<222> LOCATION: (181)
<223> OTHER INFORMATION: Wherein n is a, c, g or t
<220> FEATURE:
<221> NAME/KEY: modified_base
<222> LOCATION: (199)
<223> OTHER INFORMATION: Wherein n is a, c, g or t
<220> FEATURE:
<221> NAME/KEY: modified_base
<222> LOCATION: (203)
<223> OTHER INFORMATION: Wherein n is a, c, g or t
<220> FEATURE:
<221> NAME/KEY: modified_base
<222> LOCATION: (220)
<223> OTHER INFORMATION: Wherein n is a, c, g or t
<220> FEATURE:
<221> NAME/KEY: modified_base
<222> LOCATION: (232)
<223> OTHER INFORMATION: Wherein n is a, c, g or t
<220> FEATURE:
<221> NAME/KEY: modified_base
<222> LOCATION: (251)
<223> OTHER INFORMATION: Wherein n is a, c, g or t
<220> FEATURE:
<221> NAME/KEY: modified_base
<222> LOCATION: (257)
<223> OTHER INFORMATION: Wherein n is a, c, g or t
<220> FEATURE:
<221> NAME/KEY: modified_base
<222> LOCATION: (262)
<223> OTHER INFORMATION: Wherein n is a, c, g or t
<220> FEATURE:
<221> NAME/KEY: modified_base
<222> LOCATION: (272)
<223> OTHER INFORMATION: Wherein n is a, c, g or t
<220> FEATURE:
<221> NAME/KEY: modified_base
<222> LOCATION: (289)
<223> OTHER INFORMATION: Wherein n is a, c, g or t
<220> FEATURE:
<221> NAME/KEY: modified_base
<222> LOCATION: (308)
<223> OTHER INFORMATION: Wherein n is a, c, g or t
<220> FEATURE:
<221> NAME/KEY: modified_base
<222> LOCATION: (318)
<223> OTHER INFORMATION: Wherein n is a, c, g or t
<220> FEATURE:
<221> NAME/KEY: modified_base
<222> LOCATION: (324)
<223> OTHER INFORMATION: Wherein n is a, c, g or t
<220> FEATURE:
<221> NAME/KEY: modified_base
<222> LOCATION: (330)
<223> OTHER INFORMATION: Wherein n is a, c, g or t
<220> FEATURE:
<221> NAME/KEY: modified_base
<222> LOCATION: (342)
<223> OTHER INFORMATION: Wherein n is a, c, g or t
<220> FEATURE:
<221> NAME/KEY: modified_base
<222> LOCATION: (365)
<223> OTHER INFORMATION: Wherein n is a, c, g or t
<220> FEATURE:
<221> NAME/KEY: modified_base
<222> LOCATION: (382)
<223> OTHER INFORMATION: Wherein n is a, c, g or t
```

```
<220> FEATURE:
<221> NAME/KEY: modified_base
<222> LOCATION: (385)
<223> OTHER INFORMATION: Wherein n is a, c, g or t
<220> FEATURE:
<221> NAME/KEY: modified_base
<222> LOCATION: (386)
<223> OTHER INFORMATION: Wherein n is a, c, g or t
<220> FEATURE:
<221> NAME/KEY: modified_base
<222> LOCATION: (401)
<223> OTHER INFORMATION: Wherein n is a, c, g or t
<220> FEATURE:
<221> NAME/KEY: modified_base
<222> LOCATION: (416)
<223> OTHER INFORMATION: Wherein n is a, c, g or t
<220> FEATURE:
<221> NAME/KEY: modified_base
<222> LOCATION: (424)
<223> OTHER INFORMATION: Wherein n is a, c, g or t

<400> SEQUENCE: 11
ttttnttant tttttttancc nctnntccnn tntgttgnag ggggtaccaa atttctttat      60
ttaaaggaat ggtacaaatc aaaaaactta atttaatttt tnggtacaac ttatagaaaa     120
ggttaaggaa accccaacat gcatgcactg ccttggtaac cagggnattc ccccncggct     180
ntggggaaat tagcccaang ctnagctttc attatcactn tcccccaggg tntgcttttc     240
aaaaaaattt nccgccnagc cnaatccggg cnctcccatc tggcgcaant tggtcacttg     300
gtcccccnat tctttaaggg cttncacctn ctcattcggg tnatgtgtct caattaaatc     360
ccacngatgg gggtcatttt tntcnnttag ccagtttgtg nagttccgtt attganaaaa     420 ccan                                                                 424

<210> SEQ ID NO 12
<211> LENGTH: 426
<212> TYPE: DNA
<213> ORGANISM: Homo sapiens
<220> FEATURE:
<221> NAME/KEY: modified_base
<222> LOCATION: (15)
<223> OTHER INFORMATION: Wherein n is a, c, g or t
<220> FEATURE:
<221> NAME/KEY: modified_base
<222> LOCATION: (132)
<223> OTHER INFORMATION: Wherein n is a, c, g or t
<220> FEATURE:
<221> NAME/KEY: modified_base
<222> LOCATION: (162)
<223> OTHER INFORMATION: Wherein n is a, c, g or t
<220> FEATURE:
<221> NAME/KEY: modified_base
<222> LOCATION: (193)
<223> OTHER INFORMATION: Wherein n is a, c, g or t
<220> FEATURE:
<221> NAME/KEY: modified_base
<222> LOCATION: (204)
<223> OTHER INFORMATION: Wherein n is a, c, g or t
<220> FEATURE:
<221> NAME/KEY: modified_base
<222> LOCATION: (241)
<223> OTHER INFORMATION: Wherein n is a, c, g or t
<220> FEATURE:
<221> NAME/KEY: modified_base
<222> LOCATION: (254)
<223> OTHER INFORMATION: Wherein n is a, c, g or t
<220> FEATURE:
<221> NAME/KEY: modified_base
<222> LOCATION: (260)
<223> OTHER INFORMATION: Wherein n is a, c, g or t
<220> FEATURE:
<221> NAME/KEY: modified_base
<222> LOCATION: (268)
```

```
<223> OTHER INFORMATION: Wherein n is a, c, g or t
<220> FEATURE:
<221> NAME/KEY: modified_base
<222> LOCATION: (297)
<223> OTHER INFORMATION: Wherein n is a, c, g or t
<220> FEATURE:
<221> NAME/KEY: modified_base
<222> LOCATION: (314)
<223> OTHER INFORMATION: Wherein n is a, c, g or t
<220> FEATURE:
<221> NAME/KEY: modified_base
<222> LOCATION: (318)
<223> OTHER INFORMATION: Wherein n is a, c, g or t
<220> FEATURE:
<221> NAME/KEY: modified_base
<222> LOCATION: (324)
<223> OTHER INFORMATION: Wherein n is a, c, g or t
<220> FEATURE:
<221> NAME/KEY: modified_base
<222> LOCATION: (326)
<223> OTHER INFORMATION: Wherein n is a, c, g or t
<220> FEATURE:
<221> NAME/KEY: modified_base
<222> LOCATION: (329)
<223> OTHER INFORMATION: Wherein n is a, c, g or t
<220> FEATURE:
<221> NAME/KEY: modified_base
<222> LOCATION: (338)
<223> OTHER INFORMATION: Wherein n is a, c, g or t
<220> FEATURE:
<221> NAME/KEY: modified_base
<222> LOCATION: (341)
<223> OTHER INFORMATION: Wherein n is a, c, g or t
<220> FEATURE:
<221> NAME/KEY: modified_base
<222> LOCATION: (351)
<223> OTHER INFORMATION: Wherein n is a, c, g or t
<220> FEATURE:
<221> NAME/KEY: modified_base
<222> LOCATION: (359)
<223> OTHER INFORMATION: Wherein n is a, c, g or t
<220> FEATURE:
<221> NAME/KEY: modified_base
<222> LOCATION: (366)
<223> OTHER INFORMATION: Wherein n is a, c, g or t
<220> FEATURE:
<221> NAME/KEY: modified_base
<222> LOCATION: (369)
<223> OTHER INFORMATION: Wherein n is a, c, g or t
<220> FEATURE:
<221> NAME/KEY: modified_base
<222> LOCATION: (382)
<223> OTHER INFORMATION: Wherein n is a, c, g or t
<220> FEATURE:
<221> NAME/KEY: modified_base
<222> LOCATION: (394)
<223> OTHER INFORMATION: Wherein n is a, c, g or t
<220> FEATURE:
<221> NAME/KEY: modified_base
<222> LOCATION: (411)
<223> OTHER INFORMATION: Wherein n is a, c, g or t
<220> FEATURE:
<221> NAME/KEY: modified_base
<222> LOCATION: (423)
<223> OTHER INFORMATION: Wherein n is a, c, g or t

<400> SEQUENCE: 12
tttttttttt tttncttaa aagcttttat ctcctgctta cattacccat ctgttcttgc      60
atgttgtctg cttttccac tagagcccct aacaacttaa tcatggttat tttaagggct     120
ctaataattc cnaaactggt atcataaata agtctcgttc tnatgcttgt tttctctcta    180
tcacactgtg ttngttgctt tttnacatgc tttgtaattt ttggctgaaa gctgaaaaat    240
nacatacctg gttntacaac ctgaggtaan cagccttnta gtgtgaggtt ttatatntta    300
ctggctaaga gctnggcnct gttnantant tgttgtanct ntatatgcca naggctttna    360
```

```
tttccnctng tgtccttgct tnagtacccc attnttttag gggttcccta naaactctat    420 ctnaat                                                              426
```

```
<210> SEQ ID NO 13
<211> LENGTH: 419
<212> TYPE: DNA
<213> ORGANISM: Homo sapiens
<220> FEATURE:
<221> NAME/KEY: modified_base
<222> LOCATION: (16)
<223> OTHER INFORMATION: Wherein n is a, c, g or t
<220> FEATURE:
<221> NAME/KEY: modified_base
<222> LOCATION: (100)
<223> OTHER INFORMATION: Wherein n is a, c, g or t
<220> FEATURE:
<221> NAME/KEY: modified_base
<222> LOCATION: (135)
<223> OTHER INFORMATION: Wherein n is a, c, g or t
<220> FEATURE:
<221> NAME/KEY: modified_base
<222> LOCATION: (177)
<223> OTHER INFORMATION: Wherein n is a, c, g or t
<220> FEATURE:
<221> NAME/KEY: modified_base
<222> LOCATION: (179)
<223> OTHER INFORMATION: Wherein n is a, c, g or t
<220> FEATURE:
<221> NAME/KEY: modified_base
<222> LOCATION: (194)
<223> OTHER INFORMATION: Wherein n is a, c, g or t
<220> FEATURE:
<221> NAME/KEY: modified_base
<222> LOCATION: (231)
<223> OTHER INFORMATION: Wherein n is a, c, g or t
<220> FEATURE:
<221> NAME/KEY: modified_base
<222> LOCATION: (242)
<223> OTHER INFORMATION: Wherein n is a, c, g or t
<220> FEATURE:
<221> NAME/KEY: modified_base
<222> LOCATION: (245)
<223> OTHER INFORMATION: Wherein n is a, c, g or t
<220> FEATURE:
<221> NAME/KEY: modified_base
<222> LOCATION: (288)
<223> OTHER INFORMATION: Wherein n is a, c, g or t
<220> FEATURE:
<221> NAME/KEY: modified_base
<222> LOCATION: (333)
<223> OTHER INFORMATION: Wherein n is a, c, g or t
<220> FEATURE:
<221> NAME/KEY: modified_base
<222> LOCATION: (366)
<223> OTHER INFORMATION: Wherein n is a, c, g or t
<220> FEATURE:
<221> NAME/KEY: modified_base
<222> LOCATION: (374)
<223> OTHER INFORMATION: Wherein n is a, c, g or t
<220> FEATURE:
<221> NAME/KEY: modified_base
<222> LOCATION: (395)
<223> OTHER INFORMATION: Wherein n is a, c, g or t
<220> FEATURE:
<221> NAME/KEY: modified_base
<222> LOCATION: (405)
<223> OTHER INFORMATION: Wherein n is a, c, g or t
<220> FEATURE:
<221> NAME/KEY: modified_base
<222> LOCATION: (408)
<223> OTHER INFORMATION: Wherein n is a, c, g or t

<400> SEQUENCE: 13
tttttttttt ttttnagat agactctcac tctttcgccc aggctggagt gcagtggcgc    60
```

-continued

```
aatcaaggct cactgcaacc tctgccttat aaagcatttn ctaaaggtac aagctaaatt    120
ttaaaaatat ctctncacaa ctaatgtata acaaaaatta gttctacctc ataaacncnt    180
ggctcagccc tcgnaacaca tttccctgtt ctcaactgat gaacactcca naaacagaac    240
anatntaagc ttttccaggc ccagaaaagc tcgcgagggg atttgctntg tgtgtgacac    300
acttgccacc ctgtggcagc acagctccac acntgctttg ggccgcattt gcaagttctc    360 tgtaanccccc ctgnaagacc cggatcagct gggtngaaat tgcangcnct cttttggca    419
```

```
<210> SEQ ID NO 14
<211> LENGTH: 400
<212> TYPE: DNA
<213> ORGANISM: Homo sapiens
<220> FEATURE:
<221> NAME/KEY: modified_base
<222> LOCATION: (3)
<223> OTHER INFORMATION: Wherein n is a, c, g or t
<220> FEATURE:
<221> NAME/KEY: modified_base
<222> LOCATION: (45)
<223> OTHER INFORMATION: Wherein n is a, c, g or t
<220> FEATURE:
<221> NAME/KEY: modified_base
<222> LOCATION: (56)
<223> OTHER INFORMATION: Wherein n is a, c, g or t
<220> FEATURE:
<221> NAME/KEY: modified_base
<222> LOCATION: (110)
<223> OTHER INFORMATION: Wherein n is a, c, g or t
<220> FEATURE:
<221> NAME/KEY: modified_base
<222> LOCATION: (124)
<223> OTHER INFORMATION: Wherein n is a, c, g or t
<220> FEATURE:
<221> NAME/KEY: modified_base
<222> LOCATION: (142)
<223> OTHER INFORMATION: Wherein n is a, c, g or t
<220> FEATURE:
<221> NAME/KEY: modified_base
<222> LOCATION: (147)
<223> OTHER INFORMATION: Wherein n is a, c, g or t
<220> FEATURE:
<221> NAME/KEY: modified_base
<222> LOCATION: (190)
<223> OTHER INFORMATION: Wherein n is a, c, g or t
<220> FEATURE:
<221> NAME/KEY: modified_base
<222> LOCATION: (198)
<223> OTHER INFORMATION: Wherein n is a, c, g or t
<220> FEATURE:
<221> NAME/KEY: modified_base
<222> LOCATION: (230)
<223> OTHER INFORMATION: Wherein n is a, c, g or t
<220> FEATURE:
<221> NAME/KEY: modified_base
<222> LOCATION: (239)
<223> OTHER INFORMATION: Wherein n is a, c, g or t
<220> FEATURE:
<221> NAME/KEY: modified_base
<222> LOCATION: (254)
<223> OTHER INFORMATION: Wherein n is a, c, g or t
<220> FEATURE:
<221> NAME/KEY: modified_base
<222> LOCATION: (271)
<223> OTHER INFORMATION: Wherein n is a, c, g or t
<220> FEATURE:
<221> NAME/KEY: modified_base
<222> LOCATION: (272)
<223> OTHER INFORMATION: Wherein n is a, c, g or t
<220> FEATURE:
<221> NAME/KEY: modified_base
<222> LOCATION: (281)
<223> OTHER INFORMATION: Wherein n is a, c, g or t
<220> FEATURE:
<221> NAME/KEY: modified_base
```

<222> LOCATION: (312)
<223> OTHER INFORMATION: Wherein n is a, c, g or t
<220> FEATURE:
<221> NAME/KEY: modified_base
<222> LOCATION: (331)
<223> OTHER INFORMATION: Wherein n is a, c, g or t
<220> FEATURE:
<221> NAME/KEY: modified_base
<222> LOCATION: (342)
<223> OTHER INFORMATION: Wherein n is a, c, g or t
<220> FEATURE:
<221> NAME/KEY: modified_base
<222> LOCATION: (353)
<223> OTHER INFORMATION: Wherein n is a, c, g or t
<220> FEATURE:
<221> NAME/KEY: modified_base
<222> LOCATION: (359)
<223> OTHER INFORMATION: Wherein n is a, c, g or t
<220> FEATURE:
<221> NAME/KEY: modified_base
<222> LOCATION: (389)
<223> OTHER INFORMATION: Wherein n is a, c, g or t
<220> FEATURE:
<221> NAME/KEY: modified_base
<222> LOCATION: (392)
<223> OTHER INFORMATION: Wherein n is a, c, g or t
<220> FEATURE:
<221> NAME/KEY: modified_base
<222> LOCATION: (400)
<223> OTHER INFORMATION: Wherein n is a, c, g or t

<400> SEQUENCE: 14

```
aanccattgc caagggtatc cggaggattg tggctgtcac aggtnccgag gcccanaagg      60
ccctcaggaa agcaaagagc ttgaaaaatg tctctctgtc atggaagccn aagtgaaggc     120
tcanactgct ccaacaagga tntgcanagg gagatcgcta accttggaga ggccctggcc     180
actgcagtcn tcccccantg gcagaaggat gaattgcggg agactctcan atcccttang     240
gaaggtcgtg gatnacttgg accgagcctc nnaagccaat ntccagaaca agtgttggag     300
aagacaaagc anttcatcga cgccaacccc naccggcctc tnttctcctg ganattgana     360
gcggcgcccc cgcccagggc cttaataanc cntgaagctn                           400
```

<210> SEQ ID NO 15
<211> LENGTH: 395
<212> TYPE: DNA
<213> ORGANISM: Homo sapiens
<220> FEATURE:
<221> NAME/KEY: modified_base
<222> LOCATION: (29)
<223> OTHER INFORMATION: Wherein n is a, c, g or t
<220> FEATURE:
<221> NAME/KEY: modified_base
<222> LOCATION: (33)
<223> OTHER INFORMATION: Wherein n is a, c, g or t
<220> FEATURE:
<221> NAME/KEY: modified_base
<222> LOCATION: (74)
<223> OTHER INFORMATION: Wherein n is a, c, g or t
<220> FEATURE:
<221> NAME/KEY: modified_base
<222> LOCATION: (82)
<223> OTHER INFORMATION: Wherein n is a, c, g or t
<220> FEATURE:
<221> NAME/KEY: modified_base
<222> LOCATION: (155)
<223> OTHER INFORMATION: Wherein n is a, c, g or t
<220> FEATURE:
<221> NAME/KEY: modified_base
<222> LOCATION: (250)
<223> OTHER INFORMATION: Wherein n is a, c, g or t
<220> FEATURE:
<221> NAME/KEY: modified_base
<222> LOCATION: (258)

<223> OTHER INFORMATION: Wherein n is a, c, g or t
<220> FEATURE:
<221> NAME/KEY: modified_base
<222> LOCATION: (266)
<223> OTHER INFORMATION: Wherein n is a, c, g or t
<220> FEATURE:
<221> NAME/KEY: modified_base
<222> LOCATION: (272)
<223> OTHER INFORMATION: Wherein n is a, c, g or t
<220> FEATURE:
<221> NAME/KEY: modified_base
<222> LOCATION: (295)
<223> OTHER INFORMATION: Wherein n is a, c, g or t
<220> FEATURE:
<221> NAME/KEY: modified_base
<222> LOCATION: (298)
<223> OTHER INFORMATION: Wherein n is a, c, g or t
<220> FEATURE:
<221> NAME/KEY: modified_base
<222> LOCATION: (303)
<223> OTHER INFORMATION: Wherein n is a, c, g or t
<220> FEATURE:
<221> NAME/KEY: modified_base
<222> LOCATION: (320)
<223> OTHER INFORMATION: Wherein n is a, c, g or t
<220> FEATURE:
<221> NAME/KEY: modified_base
<222> LOCATION: (350)
<223> OTHER INFORMATION: Wherein n is a, c, g or t
<220> FEATURE:
<221> NAME/KEY: modified_base
<222> LOCATION: (360)
<223> OTHER INFORMATION: Wherein n is a, c, g or t

<400> SEQUENCE: 15
tgctttgctg cgtccaggaa gattagatng aanaatacat attgatttgc caaatgaaca      60
agcgagatta gacntactga anatccatgc aggtcccatt acaaagcatg gtgaaataga     120
tgatgaagca attgtgaagc tatcggatgg ctttnatgga gcagatctga gaatgtttg     180 tactgaagca ggtatgttcg caattcgtgc tgatcatgat tttgtagtac aggaagactt     240
catgaaagcn gtcagaaaag tggctnattc tnaaagctgg agtctaaatt ggacnacnac     300
ctntgtattt actgttggan ttttgatgct gcatgacaga ttttgcttan tgtaaaaatn     360
aagttcaaga aaattatgtt agttttggcc attat                                395

<210> SEQ ID NO 16
<211> LENGTH: 404
<212> TYPE: DNA
<213> ORGANISM: Homo sapiens
<220> FEATURE:
<221> NAME/KEY: modified_base
<222> LOCATION: (30)
<223> OTHER INFORMATION: Wherein n is a, c, g or t
<220> FEATURE:
<221> NAME/KEY: modified_base
<222> LOCATION: (61)
<223> OTHER INFORMATION: Wherein n is a, c, g or t
<220> FEATURE:
<221> NAME/KEY: modified_base
<222> LOCATION: (80)
<223> OTHER INFORMATION: Wherein n is a, c, g or t
<220> FEATURE:
<221> NAME/KEY: modified_base
<222> LOCATION: (117)
<223> OTHER INFORMATION: Wherein n is a, c, g or t
<220> FEATURE:
<221> NAME/KEY: modified_base
<222> LOCATION: (167)
<223> OTHER INFORMATION: Wherein n is a, c, g or t
<220> FEATURE:
<221> NAME/KEY: modified_base
<222> LOCATION: (170)
<223> OTHER INFORMATION: Wherein n is a, c, g or t
<220> FEATURE:
<221> NAME/KEY: modified_base
<222> LOCATION: (183)
<223> OTHER INFORMATION: Wherein n is a, c, g or t
<220> FEATURE:
<221> NAME/KEY: modified_base
<222> LOCATION: (203)
<223> OTHER INFORMATION: Wherein n is a, c, g or t
<220> FEATURE:
<221> NAME/KEY: modified_base
<222> LOCATION: (224)
<223> OTHER INFORMATION: Wherein n is a, c, g or t
<220> FEATURE:
<221> NAME/KEY: modified_base
<222> LOCATION: (227)
<223> OTHER INFORMATION: Wherein n is a, c, g or t
<220> FEATURE:
<221> NAME/KEY: modified_base
<222> LOCATION: (256)
<223> OTHER INFORMATION: Wherein n is a, c, g or t
<220> FEATURE:
<221> NAME/KEY: modified_base
<222> LOCATION: (261)
<223> OTHER INFORMATION: Wherein n is a, c, g or t
<220> FEATURE:
<221> NAME/KEY: modified_base
<222> LOCATION: (297)
<223> OTHER INFORMATION: Wherein n is a, c, g or t
<220> FEATURE:
<221> NAME/KEY: modified_base
<222> LOCATION: (361)
<223> OTHER INFORMATION: Wherein n is a, c, g or t
<220> FEATURE:
<221> NAME/KEY: modified_base
<222> LOCATION: (367)
<223> OTHER INFORMATION: Wherein n is a, c, g or t
<220> FEATURE:
<221> NAME/KEY: modified_base
<222> LOCATION: (377)
<223> OTHER INFORMATION: Wherein n is a, c, g or t
<220> FEATURE:
<221> NAME/KEY: modified_base
<222> LOCATION: (384)
<223> OTHER INFORMATION: Wherein n is a, c, g or t
<220> FEATURE:
<221> NAME/KEY: modified_base
<222> LOCATION: (386)
<223> OTHER INFORMATION: Wherein n is a, c, g or t
<220> FEATURE:
<221> NAME/KEY: modified_base
<222> LOCATION: (391)
<223> OTHER INFORMATION: Wherein n is a, c, g or t

<400> SEQUENCE: 16
ccaccactaa aatcctggct gagccctacn agtacctgtg cccctccccc aggacgagat    60
nagggcacac cctttaagtn aggtgacagg tcacctttaa gtgaggacag tcagctnaat   120
ttcacctctt gggcttgagt acctggttct cgtgccctga ggcgacnctn agccctgcag   180
ctnccatgta cgtgctgcca atngtcttga tcttctccac gccnctnaac ttgggcttca   240
gtaggagctg caggcnagaa ngaagcggtt aacagcgcca ctccatagcc gcagccnggc   300
tgcccctgct tctcaaggag gggtgtgggg ttcctccacc atcgccgccc ttgcaaacac   360
ntctcanggc ttccctnccg gctnancgca ngacttaagc atgg                    404

<210> SEQ ID NO 17
<211> LENGTH: 360
<212> TYPE: DNA
<213> ORGANISM: Homo sapiens
<220> FEATURE:
<221> NAME/KEY: modified_base
<222> LOCATION: (56)
<223> OTHER INFORMATION: Wherein n is a, c, g or t
<220> FEATURE:

```
<221> NAME/KEY: modified_base
<222> LOCATION: (81)
<223> OTHER INFORMATION: Wherein n is a, c, g or t
<220> FEATURE:
<221> NAME/KEY: modified_base
<222> LOCATION: (85)
<223> OTHER INFORMATION: Wherein n is a, c, g or t
<220> FEATURE:
<221> NAME/KEY: modified_base
<222> LOCATION: (89)
<223> OTHER INFORMATION: Wherein n is a, c, g or t
<220> FEATURE:
<221> NAME/KEY: modified_base
<222> LOCATION: (132)
<223> OTHER INFORMATION: Wherein n is a, c, g or t
<220> FEATURE:
<221> NAME/KEY: modified_base
<222> LOCATION: (146)
<223> OTHER INFORMATION: Wherein n is a, c, g or t
<220> FEATURE:
<221> NAME/KEY: modified_base
<222> LOCATION: (206)
<223> OTHER INFORMATION: Wherein n is a, c, g or t
<220> FEATURE:
<221> NAME/KEY: modified_base
<222> LOCATION: (226)
<223> OTHER INFORMATION: Wherein n is a, c, g or t
<220> FEATURE:
<221> NAME/KEY: modified_base
<222> LOCATION: (245)
<223> OTHER INFORMATION: Wherein n is a, c, g or t
<220> FEATURE:
<221> NAME/KEY: modified_base
<222> LOCATION: (254)
<223> OTHER INFORMATION: Wherein n is a, c, g or t
<220> FEATURE:
<221> NAME/KEY: modified_base
<222> LOCATION: (260)
<223> OTHER INFORMATION: Wherein n is a, c, g or t
<220> FEATURE:
<221> NAME/KEY: modified_base
<222> LOCATION: (268)
<223> OTHER INFORMATION: Wherein n is a, c, g or t
<220> FEATURE:
<221> NAME/KEY: modified_base
<222> LOCATION: (273)
<223> OTHER INFORMATION: Wherein n is a, c, g or t
<220> FEATURE:
<221> NAME/KEY: modified_base
<222> LOCATION: (275)
<223> OTHER INFORMATION: Wherein n is a, c, g or t
<220> FEATURE:
<221> NAME/KEY: modified_base
<222> LOCATION: (286)
<223> OTHER INFORMATION: Wherein n is a, c, g or t
<220> FEATURE:
<221> NAME/KEY: modified_base
<222> LOCATION: (289)
<223> OTHER INFORMATION: Wherein n is a, c, g or t
<220> FEATURE:
<221> NAME/KEY: modified_base
<222> LOCATION: (292)
<223> OTHER INFORMATION: Wherein n is a, c, g or t
<220> FEATURE:
<221> NAME/KEY: modified_base
<222> LOCATION: (294)
<223> OTHER INFORMATION: Wherein n is a, c, g or t
<220> FEATURE:
<221> NAME/KEY: modified_base
<222> LOCATION: (299)
<223> OTHER INFORMATION: Wherein n is a, c, g or t
<220> FEATURE:
<221> NAME/KEY: modified_base
<222> LOCATION: (347)
<223> OTHER INFORMATION: Wherein n is a, c, g or t

<400> SEQUENCE: 17
ggccagaagc tttccacaaa ccagtgaagg tggcagcaaa gaaagcctct tagacnagga      60
```

```
gctggcagca gctgctatct ngatngacng cagaaaccaa ccactaattc agcaaacaca      120
acctcatacc tnaccgcttc cctttnaatg gccttcggtg tgtgcgcaca tgggcacgtg      180
cggggagaac catacttatt cccctnttcc cggcctacca cctctnctcc cccttctctt      240
ctctncaatt actntctccn ctgctttntt ctnancacta ctgctngtnt cnanagccng      300
cccgcaatta cctggcaaaa ctcgcgaccc ttcgggcagc gctaaanaat gcacatttac      360
```

<210> SEQ ID NO 18
<211> LENGTH: 316
<212> TYPE: DNA
<213> ORGANISM: Homo sapiens
<220> FEATURE:
<221> NAME/KEY: modified_base
<222> LOCATION: (43)
<223> OTHER INFORMATION: Wherein n is a, c, g or t
<220> FEATURE:
<221> NAME/KEY: modified_base
<222> LOCATION: (53)
<223> OTHER INFORMATION: Wherein n is a, c, g or t
<220> FEATURE:
<221> NAME/KEY: modified_base
<222> LOCATION: (118)
<223> OTHER INFORMATION: Wherein n is a, c, g or t
<220> FEATURE:
<221> NAME/KEY: modified_base
<222> LOCATION: (145)
<223> OTHER INFORMATION: Wherein n is a, c, g or t
<220> FEATURE:
<221> NAME/KEY: modified_base
<222> LOCATION: (170)
<223> OTHER INFORMATION: Wherein n is a, c, g or t
<220> FEATURE:
<221> NAME/KEY: modified_base
<222> LOCATION: (188)
<223> OTHER INFORMATION: Wherein n is a, c, g or t
<220> FEATURE:
<221> NAME/KEY: modified_base
<222> LOCATION: (276)
<223> OTHER INFORMATION: Wherein n is a, c, g or t
<220> FEATURE:
<221> NAME/KEY: modified_base
<222> LOCATION: (306)
<223> OTHER INFORMATION: Wherein n is a, c, g or t
<220> FEATURE:
<221> NAME/KEY: modified_base
<222> LOCATION: (314)
<223> OTHER INFORMATION: Wherein n is a, c, g or t

<400> SEQUENCE: 18

```
atacatatac acatatatga ttttagatag agccatatac ctngaagtag tanatttgtt       60
tgtgtgtata tgtatgtgtc tactcatttt aaataaactt gtgatagaga tgtaattntg      120
agccagtttt tcatttgctt aaatnactca ccaagtaact aattaagttn tctttactct      180
taatgttnag tagtgagatt ctgttgaagg tgatattaaa aaccattcta tattaattaa      240
cattcatgtt gttttttaaa agcttatttg aaatcnaatt atgattattt ttcataccag      300
tcgatnttat gtangt                                                     316
```

<210> SEQ ID NO 19
<211> LENGTH: 350
<212> TYPE: DNA
<213> ORGANISM: Homo sapiens
<220> FEATURE:
<221> NAME/KEY: modified_base
<222> LOCATION: (11)
<223> OTHER INFORMATION: Wherein n is a, c, g or t
<220> FEATURE:
<221> NAME/KEY: modified_base
<222> LOCATION: (77)

```
<223> OTHER INFORMATION: Wherein n is a, c, g or t
<220> FEATURE:
<221> NAME/KEY: modified_base
<222> LOCATION: (182)
<223> OTHER INFORMATION: Wherein n is a, c, g or t
<220> FEATURE:
<221> NAME/KEY: modified_base
<222> LOCATION: (236)
<223> OTHER INFORMATION: Wherein n is a, c, g or t
<220> FEATURE:
<221> NAME/KEY: modified_base
<222> LOCATION: (252)
<223> OTHER INFORMATION: Wherein n is a, c, g or t
<220> FEATURE:
<221> NAME/KEY: modified_base
<222> LOCATION: (289)
<223> OTHER INFORMATION: Wherein n is a, c, g or t
<220> FEATURE:
<221> NAME/KEY: modified_base
<222> LOCATION: (320)
<223> OTHER INFORMATION: Wherein n is a, c, g or t
<220> FEATURE:
<221> NAME/KEY: modified_base
<222> LOCATION: (332)
<223> OTHER INFORMATION: Wherein n is a, c, g or t

<400> SEQUENCE: 19
aagggatgca nataatgctg tgtatgagct tgatggaaaa gaactctgta gtgaaagggt      60
tactattgaa catgctnggg ctcggtcacg aggtggaaga ggtagaggac gatactctga    120
ccgttttagt agtcgcagac ctcgaaatga tagacgaaat gctccacctg taagaacaga    180
anatcgtctt atagttgaga atttatcctc aagagtcagc tggcaggttt gttganatac    240
agttttgagt tnttttgatg tggcttttta aaaaagttat gggttactna tgttatattg    300
ttttattaaa agtagttttn aattaatgga tntgatggaa ttgttgtttt              350

<210> SEQ ID NO 20
<211> LENGTH: 367
<212> TYPE: DNA
<213> ORGANISM: Homo sapiens
<220> FEATURE:
<221> NAME/KEY: modified_base
<222> LOCATION: (2)
<223> OTHER INFORMATION: Wherein n is a, c, g or t
<220> FEATURE:
<221> NAME/KEY: modified_base
<222> LOCATION: (4)
<223> OTHER INFORMATION: Wherein n is a, c, g or t
<220> FEATURE:
<221> NAME/KEY: modified_base
<222> LOCATION: (5)
<223> OTHER INFORMATION: Wherein n is a, c, g or t
<220> FEATURE:
<221> NAME/KEY: modified_base
<222> LOCATION: (6)
<223> OTHER INFORMATION: Wherein n is a, c, g or t
<220> FEATURE:
<221> NAME/KEY: modified_base
<222> LOCATION: (8)
<223> OTHER INFORMATION: Wherein n is a, c, g or t
<220> FEATURE:
<221> NAME/KEY: modified_base
<222> LOCATION: (18)
<223> OTHER INFORMATION: Wherein n is a, c, g or t
<220> FEATURE:
<221> NAME/KEY: modified_base
<222> LOCATION: (21)
<223> OTHER INFORMATION: Wherein n is a, c, g or t
<220> FEATURE:
<221> NAME/KEY: modified_base
<222> LOCATION: (28)
<223> OTHER INFORMATION: Wherein n is a, c, g or t
<220> FEATURE:
<221> NAME/KEY: modified_base
```

-continued

```
<222> LOCATION: (33)
<223> OTHER INFORMATION: Wherein n is a, c, g or t
<220> FEATURE:
<221> NAME/KEY: modified_base
<222> LOCATION: (39)
<223> OTHER INFORMATION: Wherein n is a, c, g or t
<220> FEATURE:
<221> NAME/KEY: modified_base
<222> LOCATION: (42)
<223> OTHER INFORMATION: Wherein n is a, c, g or t
<220> FEATURE:
<221> NAME/KEY: modified_base
<222> LOCATION: (45)
<223> OTHER INFORMATION: Wherein n is a, c, g or t
<220> FEATURE:
<221> NAME/KEY: modified_base
<222> LOCATION: (48)
<223> OTHER INFORMATION: Wherein n is a, c, g or t
<220> FEATURE:
<221> NAME/KEY: modified_base
<222> LOCATION: (51)
<223> OTHER INFORMATION: Wherein n is a, c, g or t
<220> FEATURE:
<221> NAME/KEY: modified_base
<222> LOCATION: (60)
<223> OTHER INFORMATION: Wherein n is a, c, g or t
<220> FEATURE:
<221> NAME/KEY: modified_base
<222> LOCATION: (61)
<223> OTHER INFORMATION: Wherein n is a, c, g or t
<220> FEATURE:
<221> NAME/KEY: modified_base
<222> LOCATION: (65)
<223> OTHER INFORMATION: Wherein n is a, c, g or t
<220> FEATURE:
<221> NAME/KEY: modified_base
<222> LOCATION: (69)
<223> OTHER INFORMATION: Wherein n is a, c, g or t
<220> FEATURE:
<221> NAME/KEY: modified_base
<222> LOCATION: (70)
<223> OTHER INFORMATION: Wherein n is a, c, g or t
<220> FEATURE:
<221> NAME/KEY: modified_base
<222> LOCATION: (76)
<223> OTHER INFORMATION: Wherein n is a, c, g or t
<220> FEATURE:
<221> NAME/KEY: modified_base
<222> LOCATION: (88)
<223> OTHER INFORMATION: Wherein n is a, c, g or t
<220> FEATURE:
<221> NAME/KEY: modified_base
<222> LOCATION: (91)
<223> OTHER INFORMATION: Wherein n is a, c, g or t
<220> FEATURE:
<221> NAME/KEY: modified_base
<222> LOCATION: (92)
<223> OTHER INFORMATION: Wherein n is a, c, g or t
<220> FEATURE:
<221> NAME/KEY: modified_base
<222> LOCATION: (103)
<223> OTHER INFORMATION: Wherein n is a, c, g or t
<220> FEATURE:
<221> NAME/KEY: modified_base
<222> LOCATION: (111)
<223> OTHER INFORMATION: Wherein n is a, c, g or t
<220> FEATURE:
<221> NAME/KEY: modified_base
<222> LOCATION: (113)
<223> OTHER INFORMATION: Wherein n is a, c, g or t
<220> FEATURE:
<221> NAME/KEY: modified_base
<222> LOCATION: (115)
<223> OTHER INFORMATION: Wherein n is a, c, g or t
<220> FEATURE:
<221> NAME/KEY: modified_base
<222> LOCATION: (116)
<223> OTHER INFORMATION: Wherein n is a, c, g or t
<220> FEATURE:
```

```
<221> NAME/KEY: modified_base
<222> LOCATION: (120)
<223> OTHER INFORMATION: Wherein n is a, c, g or t
<220> FEATURE:
<221> NAME/KEY: modified_base
<222> LOCATION: (121)
<223> OTHER INFORMATION: Wherein n is a, c, g or t
<220> FEATURE:
<221> NAME/KEY: modified_base
<222> LOCATION: (127)
<223> OTHER INFORMATION: Wherein n is a, c, g or t
<220> FEATURE:
<221> NAME/KEY: modified_base
<222> LOCATION: (134)
<223> OTHER INFORMATION: Wherein n is a, c, g or t
<220> FEATURE:
<221> NAME/KEY: modified_base
<222> LOCATION: (135)
<223> OTHER INFORMATION: Wherein n is a, c, g or t
<220> FEATURE:
<221> NAME/KEY: modified_base
<222> LOCATION: (142)
<223> OTHER INFORMATION: Wherein n is a, c, g or t
<220> FEATURE:
<221> NAME/KEY: modified_base
<222> LOCATION: (149)
<223> OTHER INFORMATION: Wherein n is a, c, g or t
<220> FEATURE:
<221> NAME/KEY: modified_base
<222> LOCATION: (151)
<223> OTHER INFORMATION: Wherein n is a, c, g or t
<220> FEATURE:
<221> NAME/KEY: modified_base
<222> LOCATION: (152)
<223> OTHER INFORMATION: Wherein n is a, c, g or t
<220> FEATURE:
<221> NAME/KEY: modified_base
<222> LOCATION: (163)
<223> OTHER INFORMATION: Wherein n is a, c, g or t
<220> FEATURE:
<221> NAME/KEY: modified_base
<222> LOCATION: (167)
<223> OTHER INFORMATION: Wherein n is a, c, g or t
<220> FEATURE:
<221> NAME/KEY: modified_base
<222> LOCATION: (173)
<223> OTHER INFORMATION: Wherein n is a, c, g or t
<220> FEATURE:
<221> NAME/KEY: modified_base
<222> LOCATION: (176)
<223> OTHER INFORMATION: Wherein n is a, c, g or t
<220> FEATURE:
<221> NAME/KEY: modified_base
<222> LOCATION: (184)
<223> OTHER INFORMATION: Wherein n is a, c, g or t
<220> FEATURE:
<221> NAME/KEY: modified_base
<222> LOCATION: (197)
<223> OTHER INFORMATION: Wherein n is a, c, g or t
<220> FEATURE:
<221> NAME/KEY: modified_base
<222> LOCATION: (203)
<223> OTHER INFORMATION: Wherein n is a, c, g or t
<220> FEATURE:
<221> NAME/KEY: modified_base
<222> LOCATION: (224)
<223> OTHER INFORMATION: Wherein n is a, c, g or t
<220> FEATURE:
<221> NAME/KEY: modified_base
<222> LOCATION: (225)
<223> OTHER INFORMATION: Wherein n is a, c, g or t
<220> FEATURE:
<221> NAME/KEY: modified_base
<222> LOCATION: (227)
<223> OTHER INFORMATION: Wherein n is a, c, g or t
<220> FEATURE:
<221> NAME/KEY: modified_base
<222> LOCATION: (255)
<223> OTHER INFORMATION: Wherein n is a, c, g or t
```

<220> FEATURE:
<221> NAME/KEY: modified_base
<222> LOCATION: (258)
<223> OTHER INFORMATION: Wherein n is a, c, g or t
<220> FEATURE:
<221> NAME/KEY: modified_base
<222> LOCATION: (262)
<223> OTHER INFORMATION: Wherein n is a, c, g or t
<220> FEATURE:
<221> NAME/KEY: modified_base
<222> LOCATION: (279)
<223> OTHER INFORMATION: Wherein n is a, c, g or t
<220> FEATURE:
<221> NAME/KEY: modified_base
<222> LOCATION: (293)
<223> OTHER INFORMATION: Wherein n is a, c, g or t
<220> FEATURE:
<221> NAME/KEY: modified_base
<222> LOCATION: (312)
<223> OTHER INFORMATION: Wherein n is a, c, g or t
<220> FEATURE:
<221> NAME/KEY: modified_base
<222> LOCATION: (314)
<223> OTHER INFORMATION: Wherein n is a, c, g or t
<220> FEATURE:
<221> NAME/KEY: modified_base
<222> LOCATION: (320)
<223> OTHER INFORMATION: Wherein n is a, c, g or t
<220> FEATURE:
<221> NAME/KEY: modified_base
<222> LOCATION: (343)
<223> OTHER INFORMATION: Wherein n is a, c, g or t
<220> FEATURE:
<221> NAME/KEY: modified_base
<222> LOCATION: (345)
<223> OTHER INFORMATION: Wherein n is a, c, g or t
<220> FEATURE:
<221> NAME/KEY: modified_base
<222> LOCATION: (348)
<223> OTHER INFORMATION: Wherein n is a, c, g or t
<220> FEATURE:
<221> NAME/KEY: modified_base
<222> LOCATION: (359)
<223> OTHER INFORMATION: Wherein n is a, c, g or t
<220> FEATURE:
<221> NAME/KEY: modified_base
<222> LOCATION: (365)
<223> OTHER INFORMATION: Wherein n is a, c, g or t

<400> SEQUENCE: 20

```
gntnnncnca agatcctnct ntccccengg gengecccnc cnccngtnat naccggttttn    60
ntaanatcnn gccgcnccecg aagtctcnct nntgccgaga tgnccettat ncncnnatgn   120
ncaattntga cctnnggcga anaatggcng nngtgtatca gtntccnctc tgnggnctct   180
tagnatctga ccactangac ccnctatcct ctcaaaccct gtanncngcc ctaatttgtg   240
ccaattagtg catgntanag cntcctggcc cagatggcnt ccatatcctg gtncggcttc   300
cgcccctacc angncatccn catctactag agcttatccg ctncntgngg cgcaccggnt   360
ccccnct                                                              367
```

<210> SEQ ID NO 21
<211> LENGTH: 366
<212> TYPE: DNA
<213> ORGANISM: Homo sapiens
<220> FEATURE:
<221> NAME/KEY: modified_base
<222> LOCATION: (22)
<223> OTHER INFORMATION: Wherein n is a, c, g or t
<220> FEATURE:
<221> NAME/KEY: modified_base
<222> LOCATION: (100)
<223> OTHER INFORMATION: Wherein n is a, c, g or t
<220> FEATURE:

<221> NAME/KEY: modified_base
<222> LOCATION: (155)
<223> OTHER INFORMATION: Wherein n is a, c, g or t
<220> FEATURE:
<221> NAME/KEY: modified_base
<222> LOCATION: (268)
<223> OTHER INFORMATION: Wherein n is a, c, g or t
<220> FEATURE:
<221> NAME/KEY: modified_base
<222> LOCATION: (269)
<223> OTHER INFORMATION: Wherein n is a, c, g or t
<220> FEATURE:
<221> NAME/KEY: modified_base
<222> LOCATION: (366)
<223> OTHER INFORMATION: Wherein n is a, c, g or t

<400> SEQUENCE: 21

```
cccaacacaa tggtctaagt anaactgtat tgctctgtag tatagttcca cattggcaac      60
ctacaatggg aaaatccata cataagtcag ttacttcctn atgagctttc tccttctgaa     120
tcctttatct tctgaagaaa gtacacacct tggtnatgat atctttgaat tgcccttctt     180
tccaggcatc agttggatga ttcatcatgg taattatggc attatcatat tcttcatact     240
tgtcatacga aaacaccagt tctgcccnna gatgagcttg ttctgcagct cttagcacct     300
tgggaatatt cactctagac cagaaacagc tcccggtgct ccctcatttt ctgaggctta     360
aattta                                                                366
```

<210> SEQ ID NO 22
<211> LENGTH: 315
<212> TYPE: DNA
<213> ORGANISM: Homo sapiens
<220> FEATURE:
<221> NAME/KEY: modified_base
<222> LOCATION: (47)
<223> OTHER INFORMATION: Wherein n is a, c, g or t
<220> FEATURE:
<221> NAME/KEY: modified_base
<222> LOCATION: (69)
<223> OTHER INFORMATION: Wherein n is a, c, g or t
<220> FEATURE:
<221> NAME/KEY: modified_base
<222> LOCATION: (77)
<223> OTHER INFORMATION: Wherein n is a, c, g or t
<220> FEATURE:
<221> NAME/KEY: modified_base
<222> LOCATION: (103)
<223> OTHER INFORMATION: Wherein n is a, c, g or t
<220> FEATURE:
<221> NAME/KEY: modified_base
<222> LOCATION: (133)
<223> OTHER INFORMATION: Wherein n is a, c, g or t
<220> FEATURE:
<221> NAME/KEY: modified_base
<222> LOCATION: (148)
<223> OTHER INFORMATION: Wherein n is a, c, g or t
<220> FEATURE:
<221> NAME/KEY: modified_base
<222> LOCATION: (182)
<223> OTHER INFORMATION: Wherein n is a, c, g or t
<220> FEATURE:
<221> NAME/KEY: modified_base
<222> LOCATION: (186)
<223> OTHER INFORMATION: Wherein n is a, c, g or t
<220> FEATURE:
<221> NAME/KEY: modified_base
<222> LOCATION: (187)
<223> OTHER INFORMATION: Wherein n is a, c, g or t
<220> FEATURE:
<221> NAME/KEY: modified_base
<222> LOCATION: (197)
<223> OTHER INFORMATION: Wherein n is a, c, g or t
<220> FEATURE:
<221> NAME/KEY: modified_base
<222> LOCATION: (247)
<223> OTHER INFORMATION: Wherein n is a, c, g or t
<220> FEATURE:
<221> NAME/KEY: modified_base
<222> LOCATION: (260)
<223> OTHER INFORMATION: Wherein n is a, c, g or t
<220> FEATURE:
<221> NAME/KEY: modified_base
<222> LOCATION: (262)
<223> OTHER INFORMATION: Wherein n is a, c, g or t
<220> FEATURE:
<221> NAME/KEY: modified_base
<222> LOCATION: (266)
<223> OTHER INFORMATION: Wherein n is a, c, g or t
<220> FEATURE:
<221> NAME/KEY: modified_base
<222> LOCATION: (267)
<223> OTHER INFORMATION: Wherein n is a, c, g or t
<220> FEATURE:
<221> NAME/KEY: modified_base
<222> LOCATION: (299)
<223> OTHER INFORMATION: Wherein n is a, c, g or t

<400> SEQUENCE: 22

| | | | | | |
|---|---|---|---|---|---|
| acttaatgca | atctctggag | gataatttgg | atcaagaaat | aaagaanaaa | tgaattagga | 60 |
| gaagaaatna | ctgggtnata | tttcaatatt | ttagaacttt | aanaatgttg | actatgattt | 120 |
| caatatattt | gtnaaaactg | agatacangt | ttgacctata | tctgcatttt | gataattaaa | 180 |
| cnaatnnatt | ctatttnaat | gttgtttcag | agtcacagca | cagactgaaa | ctttttttga | 240 |
| atacctnaat | atcacacttn | tncttnnaat | gatgttgaag | acaatgatga | catgccttna | 300 |
| gcatataatg | tcgac | | | | | 315 |

<210> SEQ ID NO 23
<211> LENGTH: 202
<212> TYPE: DNA
<213> ORGANISM: Homo sapiens
<220> FEATURE:
<221> NAME/KEY: modified_base
<222> LOCATION: (18)
<223> OTHER INFORMATION: Wherein n is a, c, g or t
<220> FEATURE:
<221> NAME/KEY: modified_base
<222> LOCATION: (58)
<223> OTHER INFORMATION: Wherein n is a, c, g or t
<220> FEATURE:
<221> NAME/KEY: modified_base
<222> LOCATION: (81)
<223> OTHER INFORMATION: Wherein n is a, c, g or t
<220> FEATURE:
<221> NAME/KEY: modified_base
<222> LOCATION: (128)
<223> OTHER INFORMATION: Wherein n is a, c, g or t
<220> FEATURE:
<221> NAME/KEY: modified_base
<222> LOCATION: (131)
<223> OTHER INFORMATION: Wherein n is a, c, g or t
<220> FEATURE:
<221> NAME/KEY: modified_base
<222> LOCATION: (132)
<223> OTHER INFORMATION: Wherein n is a, c, g or t
<220> FEATURE:
<221> NAME/KEY: modified_base
<222> LOCATION: (137)
<223> OTHER INFORMATION: Wherein n is a, c, g or t
<220> FEATURE:
<221> NAME/KEY: modified_base
<222> LOCATION: (154)
<223> OTHER INFORMATION: Wherein n is a, c, g or t
<220> FEATURE:
<221> NAME/KEY: modified_base
<222> LOCATION: (191)
<223> OTHER INFORMATION: Wherein n is a, c, g or t

<400> SEQUENCE: 23

```
actaatccag tgtggtgnaa ttccattgtg ttgggcaact caggatatta aatttatnat    60
ttaaaaattc ccaagagaaa naaactccag gccctgattg tttcactggg gaattttacc   120
aaatgttnca nnaaganatg acgctgattc tgtnaaatct ttttcagaag atagaggaga   180
acacccaccg nttcatttta tg                                            202
```

<210> SEQ ID NO 24
<211> LENGTH: 365
<212> TYPE: DNA
<213> ORGANISM: Homo sapiens
<220> FEATURE:
<221> NAME/KEY: modified_base
<222> LOCATION: (134)
<223> OTHER INFORMATION: Wherein n is a, c, g or t
<220> FEATURE:
<221> NAME/KEY: modified_base
<222> LOCATION: (141)
<223> OTHER INFORMATION: Wherein n is a, c, g or t
<220> FEATURE:
<221> NAME/KEY: modified_base
<222> LOCATION: (172)
<223> OTHER INFORMATION: Wherein n is a, c, g or t
<220> FEATURE:
<221> NAME/KEY: modified_base
<222> LOCATION: (180)
<223> OTHER INFORMATION: Wherein n is a, c, g or t
<220> FEATURE:
<221> NAME/KEY: modified_base
<222> LOCATION: (274)
<223> OTHER INFORMATION: Wherein n is a, c, g or t
<220> FEATURE:
<221> NAME/KEY: modified_base
<222> LOCATION: (279)
<223> OTHER INFORMATION: Wherein n is a, c, g or t
<220> FEATURE:
<221> NAME/KEY: modified_base
<222> LOCATION: (300)
<223> OTHER INFORMATION: Wherein n is a, c, g or t
<220> FEATURE:
<221> NAME/KEY: modified_base
<222> LOCATION: (315)
<223> OTHER INFORMATION: Wherein n is a, c, g or t
<220> FEATURE:
<221> NAME/KEY: modified_base
<222> LOCATION: (323)
<223> OTHER INFORMATION: Wherein n is a, c, g or t
<220> FEATURE:
<221> NAME/KEY: modified_base
<222> LOCATION: (349)
<223> OTHER INFORMATION: Wherein n is a, c, g or t

<400> SEQUENCE: 24

```
ggatttcttg ccctttctc ccttttaag tatcaatgta tgaaatccac ctgtaccacc    60
ctttctgcca tacaaccgct accacatctg gctcctagaa cctgttttgc tttcatagat   120
ggatctcgga accnagtgtt nacttcattt ttaaacccca ttttagcaga tngtttgctn   180
tggtctgtct gtattcacca tggggcctgt acacaccacg tgtggttata gtcaaacaca   240
gtgccctcca ttgtggccac atgggagacc catnacccna tactgcatcc tgggctgatn   300
acggcactgc atctnacccg acntgggatt gaacccgggg tgggcagcng aattgaacag   360
gatca                                                               365
```

<210> SEQ ID NO 25
<211> LENGTH: 359
<212> TYPE: DNA
<213> ORGANISM: Homo sapiens
<220> FEATURE:
<221> NAME/KEY: modified_base

```
<222> LOCATION: (126)
<223> OTHER INFORMATION: Wherein n is a, c, g or t
<220> FEATURE:
<221> NAME/KEY: modified_base
<222> LOCATION: (131)
<223> OTHER INFORMATION: Wherein n is a, c, g or t
<220> FEATURE:
<221> NAME/KEY: modified_base
<222> LOCATION: (137)
<223> OTHER INFORMATION: Wherein n is a, c, g or t
<220> FEATURE:
<221> NAME/KEY: modified_base
<222> LOCATION: (154)
<223> OTHER INFORMATION: Wherein n is a, c, g or t
<220> FEATURE:
<221> NAME/KEY: modified_base
<222> LOCATION: (157)
<223> OTHER INFORMATION: Wherein n is a, c, g or t
<220> FEATURE:
<221> NAME/KEY: modified_base
<222> LOCATION: (170)
<223> OTHER INFORMATION: Wherein n is a, c, g or t
<220> FEATURE:
<221> NAME/KEY: modified_base
<222> LOCATION: (179)
<223> OTHER INFORMATION: Wherein n is a, c, g or t
<220> FEATURE:
<221> NAME/KEY: modified_base
<222> LOCATION: (181)
<223> OTHER INFORMATION: Wherein n is a, c, g or t
<220> FEATURE:
<221> NAME/KEY: modified_base
<222> LOCATION: (201)
<223> OTHER INFORMATION: Wherein n is a, c, g or t
<220> FEATURE:
<221> NAME/KEY: modified_base
<222> LOCATION: (209)
<223> OTHER INFORMATION: Wherein n is a, c, g or t
<220> FEATURE:
<221> NAME/KEY: modified_base
<222> LOCATION: (221)
<223> OTHER INFORMATION: Wherein n is a, c, g or t
<220> FEATURE:
<221> NAME/KEY: modified_base
<222> LOCATION: (231)
<223> OTHER INFORMATION: Wherein n is a, c, g or t
<220> FEATURE:
<221> NAME/KEY: modified_base
<222> LOCATION: (266)
<223> OTHER INFORMATION: Wherein n is a, c, g or t
<220> FEATURE:
<221> NAME/KEY: modified_base
<222> LOCATION: (276)
<223> OTHER INFORMATION: Wherein n is a, c, g or t
<220> FEATURE:
<221> NAME/KEY: modified_base
<222> LOCATION: (288)
<223> OTHER INFORMATION: Wherein n is a, c, g or t
<220> FEATURE:
<221> NAME/KEY: modified_base
<222> LOCATION: (301)
<223> OTHER INFORMATION: Wherein n is a, c, g or t
<220> FEATURE:
<221> NAME/KEY: modified_base
<222> LOCATION: (312)
<223> OTHER INFORMATION: Wherein n is a, c, g or t
<220> FEATURE:
<221> NAME/KEY: modified_base
<222> LOCATION: (324)
<223> OTHER INFORMATION: Wherein n is a, c, g or t
<220> FEATURE:
<221> NAME/KEY: modified_base
<222> LOCATION: (357)
<223> OTHER INFORMATION: Wherein n is a, c, g or t
<220> FEATURE:
<221> NAME/KEY: modified_base
<222> LOCATION: (358)
<223> OTHER INFORMATION: Wherein n is a, c, g or t
```

<400> SEQUENCE: 25

```
gtttcctgct tcaacagtgc ttggacggaa cccggcgctc gttccccacc ccggccggcc    60
gcccatagcc agccctccgt cacctcttca ccgcaccctc ggactgcccc aaggcccccg   120
ccgccnctcc ngcgccncgc agccaccgcc gccnccncca cctctccttn gtcccgccnt   180
nacaacgcgt ccacctcgca ngttcgccng aactaccacc nggactcata ngccgccctc   240
aaccgcccga tcaacctgga gctctncccc ccgacnttaa cctttccntg tcttacttac   300
nttaaccgcc gnttattttg cttnaaaaga acttttcccc aatactttct ttcaccnnt    359
```

<210> SEQ ID NO 26
<211> LENGTH: 400
<212> TYPE: DNA
<213> ORGANISM: Homo sapiens
<220> FEATURE:
<221> NAME/KEY: modified_base
<222> LOCATION: (34)
<223> OTHER INFORMATION: Wherein n is a, c, g or t
<220> FEATURE:
<221> NAME/KEY: modified_base
<222> LOCATION: (35)
<223> OTHER INFORMATION: Wherein n is a, c, g or t
<220> FEATURE:
<221> NAME/KEY: modified_base
<222> LOCATION: (99)
<223> OTHER INFORMATION: Wherein n is a, c, g or t
<220> FEATURE:
<221> NAME/KEY: modified_base
<222> LOCATION: (183)
<223> OTHER INFORMATION: Wherein n is a, c, g or t
<220> FEATURE:
<221> NAME/KEY: modified_base
<222> LOCATION: (186)
<223> OTHER INFORMATION: Wherein n is a, c, g or t
<220> FEATURE:
<221> NAME/KEY: modified_base
<222> LOCATION: (189)
<223> OTHER INFORMATION: Wherein n is a, c, g or t
<220> FEATURE:
<221> NAME/KEY: modified_base
<222> LOCATION: (196)
<223> OTHER INFORMATION: Wherein n is a, c, g or t
<220> FEATURE:
<221> NAME/KEY: modified_base
<222> LOCATION: (200)
<223> OTHER INFORMATION: Wherein n is a, c, g or t
<220> FEATURE:
<221> NAME/KEY: modified_base
<222> LOCATION: (204)
<223> OTHER INFORMATION: Wherein n is a, c, g or t
<220> FEATURE:
<221> NAME/KEY: modified_base
<222> LOCATION: (208)
<223> OTHER INFORMATION: Wherein n is a, c, g or t
<220> FEATURE:
<221> NAME/KEY: modified_base
<222> LOCATION: (263)
<223> OTHER INFORMATION: Wherein n is a, c, g or t
<220> FEATURE:
<221> NAME/KEY: modified_base
<222> LOCATION: (268)
<223> OTHER INFORMATION: Wherein n is a, c, g or t
<220> FEATURE:
<221> NAME/KEY: modified_base
<222> LOCATION: (343)
<223> OTHER INFORMATION: Wherein n is a, c, g or t
<220> FEATURE:
<221> NAME/KEY: modified_base
<222> LOCATION: (349)
<223> OTHER INFORMATION: Wherein n is a, c, g or t
<220> FEATURE:
<221> NAME/KEY: modified_base
<222> LOCATION: (357)
<223> OTHER INFORMATION: Wherein n is a, c, g or t

```
<220> FEATURE:
<221> NAME/KEY: modified_base
<222> LOCATION: (384)
<223> OTHER INFORMATION: Wherein n is a, c, g or t
<220> FEATURE:
<221> NAME/KEY: modified_base
<222> LOCATION: (385)
<223> OTHER INFORMATION: Wherein n is a, c, g or t
<220> FEATURE:
<221> NAME/KEY: modified_base
<222> LOCATION: (388)
<223> OTHER INFORMATION: Wherein n is a, c, g or t
<220> FEATURE:
<221> NAME/KEY: modified_base
<222> LOCATION: (392)
<223> OTHER INFORMATION: Wherein n is a, c, g or t
<220> FEATURE:
<221> NAME/KEY: modified_base
<222> LOCATION: (395)
<223> OTHER INFORMATION: Wherein n is a, c, g or t
<220> FEATURE:
<221> NAME/KEY: modified_base
<222> LOCATION: (400)
<223> OTHER INFORMATION: Wherein n is a, c, g or t

<400> SEQUENCE: 26
agtgaaacag tatatgtgaa aaggagtttg tgannagcta cataaaaata ttagatatct        60
ttataatttc caataggata ctcatcagtt ttgaataana gacatattct agagaaacca       120
ggtttctggt ttcagatttg aactctcaag agcttggaag ttatcactcc catcctcacg       180
acnacnaana aatctnaacn aacngaaaac caatgacttt tcttagatct gtcaaagaac       240
ttcagccacg aggaaaacta tcnccctnaa tactgggggac tggaaagaga gggtacagag      300
aatcacagtg aatcatagcc caagatcagc ttgcccggag ctnaagctng tacgatnatt       360
acttacaggg accacttcac agtnngtnga tnaantgccn                             400

<210> SEQ ID NO 27
<211> LENGTH: 366
<212> TYPE: DNA
<213> ORGANISM: Homo sapiens
<220> FEATURE:
<221> NAME/KEY: modified_base
<222> LOCATION: (69)
<223> OTHER INFORMATION: Wherein n is a, c, g or t
<220> FEATURE:
<221> NAME/KEY: modified_base
<222> LOCATION: (115)
<223> OTHER INFORMATION: Wherein n is a, c, g or t
<220> FEATURE:
<221> NAME/KEY: modified_base
<222> LOCATION: (225)
<223> OTHER INFORMATION: Wherein n is a, c, g or t
<220> FEATURE:
<221> NAME/KEY: modified_base
<222> LOCATION: (230)
<223> OTHER INFORMATION: Wherein n is a, c, g or t
<220> FEATURE:
<221> NAME/KEY: modified_base
<222> LOCATION: (258)
<223> OTHER INFORMATION: Wherein n is a, c, g or t
<220> FEATURE:
<221> NAME/KEY: modified_base
<222> LOCATION: (276)
<223> OTHER INFORMATION: Wherein n is a, c, g or t
<220> FEATURE:
<221> NAME/KEY: modified_base
<222> LOCATION: (307)
<223> OTHER INFORMATION: Wherein n is a, c, g or t
<220> FEATURE:
<221> NAME/KEY: modified_base
<222> LOCATION: (334)
<223> OTHER INFORMATION: Wherein n is a, c, g or t
<220> FEATURE:
```

<221> NAME/KEY: modified_base
<222> LOCATION: (365)
<223> OTHER INFORMATION: Wherein n is a, c, g or t

<400> SEQUENCE: 27
gaatttctta gaaactgaag tttactctgt tccaagatat atcttcactg tcttaatcaa     60
agggcgctng aatcatagca aatattctca tctttcaact aactttaagt agttntcctg    120
gaattttaca ttttccagaa aacactcctt tctgtatctg tgaaagaaag tgtgcctcag    180
gctgtagact gggctgcact ggacacctgc gggggactct ggctnagtgn ggacatggtc    240
agtattgatt ttcctcanac tcagcctgtg tagctntgaa agcatggaac agattacact    300
gcagttnacg tcatcccaca catcttggac tccnagaccc ggggaggtca catagtccgt    360 tatgna                                                              366

<210> SEQ ID NO 28
<211> LENGTH: 402
<212> TYPE: DNA
<213> ORGANISM: Homo sapiens
<220> FEATURE:
<221> NAME/KEY: modified_base
<222> LOCATION: (58)
<223> OTHER INFORMATION: Wherein n is a, c, g or t
<220> FEATURE:
<221> NAME/KEY: modified_base
<222> LOCATION: (156)
<223> OTHER INFORMATION: Wherein n is a, c, g or t
<220> FEATURE:
<221> NAME/KEY: modified_base
<222> LOCATION: (184)
<223> OTHER INFORMATION: Wherein n is a, c, g or t
<220> FEATURE:
<221> NAME/KEY: modified_base
<222> LOCATION: (201)
<223> OTHER INFORMATION: Wherein n is a, c, g or t
<220> FEATURE:
<221> NAME/KEY: modified_base
<222> LOCATION: (231)
<223> OTHER INFORMATION: Wherein n is a, c, g or t
<220> FEATURE:
<221> NAME/KEY: modified_base
<222> LOCATION: (302)
<223> OTHER INFORMATION: Wherein n is a, c, g or t
<220> FEATURE:
<221> NAME/KEY: modified_base
<222> LOCATION: (329)
<223> OTHER INFORMATION: Wherein n is a, c, g or t
<220> FEATURE:
<221> NAME/KEY: modified_base
<222> LOCATION: (333)
<223> OTHER INFORMATION: Wherein n is a, c, g or t
<220> FEATURE:
<221> NAME/KEY: modified_base
<222> LOCATION: (341)
<223> OTHER INFORMATION: Wherein n is a, c, g or t
<220> FEATURE:
<221> NAME/KEY: modified_base
<222> LOCATION: (354)
<223> OTHER INFORMATION: Wherein n is a, c, g or t
<220> FEATURE:
<221> NAME/KEY: modified_base
<222> LOCATION: (363)
<223> OTHER INFORMATION: Wherein n is a, c, g or t
<220> FEATURE:
<221> NAME/KEY: modified_base
<222> LOCATION: (374)
<223> OTHER INFORMATION: Wherein n is a, c, g or t
<220> FEATURE:
<221> NAME/KEY: modified_base
<222> LOCATION: (375)
<223> OTHER INFORMATION: Wherein n is a, c, g or t
<220> FEATURE:
<221> NAME/KEY: modified_base

```
<222> LOCATION: (380)
<223> OTHER INFORMATION: Wherein n is a, c, g or t
<220> FEATURE:
<221> NAME/KEY: modified_base
<222> LOCATION: (384)
<223> OTHER INFORMATION: Wherein n is a, c, g or t

<400> SEQUENCE: 28
agtgggagcc tcctccttcc ccactcagtt ctttacatcc ccgaggcgca gctgggcnaa      60
ggaagtggcc agctgcagcg cctcctgcag gcagccaacg ttcttgcctg tggcctgtgc     120
agacacatcc ttgccaccac ctttaccgtc catcangcct gacacctgct gcacccactc     180
gctngctttt aagccccgat nggctgcatt ctggggact tgacacaggc ncgtgatctt      240
gccagcctca ttgtccaccg tgaagagcat ggcaaaaagt ctgaggggag tgcatcttga     300
anagcttcaa ggcttcattc agggccttng ctnaggcgcc nctctccatc tccnggaata     360
acnagaggct ggtnngggtn actntcaata aactgcttcg tc                       402

<210> SEQ ID NO 29
<211> LENGTH: 175
<212> TYPE: DNA
<213> ORGANISM: Homo sapiens

<400> SEQUENCE: 29
cggacgggca tgaccggtcc ggtcagctgg gtggccagtt tcagttcttc agcagaactg      60
tctcccttct tggggccga gggcttcctg gggaagagga tgagtttgga gcggtactcc     120
ttcagccgct gcacgttggt ctgcagggac tccgtggact tgttccgcct cctcg         175

<210> SEQ ID NO 30
<211> LENGTH: 360
<212> TYPE: DNA
<213> ORGANISM: Homo sapiens

<400> SEQUENCE: 30
ttgtatttct tatgatctct gatgggttct tctcgaaaat gccaagtgga agactttgtg      60
gcatgctcca gatttaaatc cagctgaggc tcccttgtt ttcagttcca tgtaacaatc     120
tggaaggaaa cttcacggac aggaagactg ctggagaaga gaagcgtgtt agcccatttg     180
aggtctgggg aatcatgtaa agggtaccca gacctcactt ttagttattt acatcaatga     240
gttctttcag ggaaccaaac ccagaattcg gtgcaaaagc caaacatctt ggtgggattt     300
gataaatgcc ttgggacctg gagtgctggg cttgtgcaca ggaagagcac cagccgctga     360

<210> SEQ ID NO 31
<211> LENGTH: 380
<212> TYPE: DNA
<213> ORGANISM: Homo sapiens
<220> FEATURE:
<221> NAME/KEY: modified_base
<222> LOCATION: (100)
<223> OTHER INFORMATION: Wherein n is a, c, g or t
<220> FEATURE:
<221> NAME/KEY: modified_base
<222> LOCATION: (128)
<223> OTHER INFORMATION: Wherein n is a, c, g or t
<220> FEATURE:
<221> NAME/KEY: modified_base
<222> LOCATION: (199)
<223> OTHER INFORMATION: Wherein n is a, c, g or t
<220> FEATURE:
<221> NAME/KEY: modified_base
<222> LOCATION: (200)
<223> OTHER INFORMATION: Wherein n is a, c, g or t
<220> FEATURE:
```

<221> NAME/KEY: modified_base
<222> LOCATION: (208)
<223> OTHER INFORMATION: Wherein n is a, c, g or t
<220> FEATURE:
<221> NAME/KEY: modified_base
<222> LOCATION: (210)
<223> OTHER INFORMATION: Wherein n is a, c, g or t
<220> FEATURE:
<221> NAME/KEY: modified_base
<222> LOCATION: (275)
<223> OTHER INFORMATION: Wherein n is a, c, g or t
<220> FEATURE:
<221> NAME/KEY: modified_base
<222> LOCATION: (318)
<223> OTHER INFORMATION: Wherein n is a, c, g or t
<220> FEATURE:
<221> NAME/KEY: modified_base
<222> LOCATION: (327)
<223> OTHER INFORMATION: Wherein n is a, c, g or t
<220> FEATURE:
<221> NAME/KEY: modified_base
<222> LOCATION: (337)
<223> OTHER INFORMATION: Wherein n is a, c, g or t
<220> FEATURE:
<221> NAME/KEY: modified_base
<222> LOCATION: (354)
<223> OTHER INFORMATION: Wherein n is a, c, g or t
<220> FEATURE:
<221> NAME/KEY: modified_base
<222> LOCATION: (356)
<223> OTHER INFORMATION: Wherein n is a, c, g or t

<400> SEQUENCE: 31

```
acgctctaag cctgtccacg agctcaatag ggaagcctgt gatgactaca gactttgcga      60
acgctacgcc atggtttatg gatacaatgc tgcctataan cgctacttca ggaagcgccg     120
agggaccnaa tgagactgag ggaagaaaaa aaatctcttt ttttctggag gctggcacct     180
gattttgtat ccccctgtnn cagcattncn gaaatacata ggcttatata caatgcttct     240
ttcctgtata ttctcttgtc tggctgcacc ccttnttccc gccccagat tgataagtaa      300
tgaaagtgca ctgcagtnag ggtcaangga gactcancat atgtgattgt tccntnataa     360
acttctggtg tgatactttc                                                 380
```

<210> SEQ ID NO 32
<211> LENGTH: 440
<212> TYPE: DNA
<213> ORGANISM: Homo sapiens
<220> FEATURE:
<221> NAME/KEY: modified_base
<222> LOCATION: (154)
<223> OTHER INFORMATION: Wherein n is a, c, g or t
<220> FEATURE:
<221> NAME/KEY: modified_base
<222> LOCATION: (254)
<223> OTHER INFORMATION: Wherein n is a, c, g or t
<220> FEATURE:
<221> NAME/KEY: modified_base
<222> LOCATION: (258)
<223> OTHER INFORMATION: Wherein n is a, c, g or t
<220> FEATURE:
<221> NAME/KEY: modified_base
<222> LOCATION: (305)
<223> OTHER INFORMATION: Wherein n is a, c, g or t
<220> FEATURE:
<221> NAME/KEY: modified_base
<222> LOCATION: (355)
<223> OTHER INFORMATION: Wherein n is a, c, g or t
<220> FEATURE:
<221> NAME/KEY: modified_base
<222> LOCATION: (380)
<223> OTHER INFORMATION: Wherein n is a, c, g or t
<220> FEATURE:
<221> NAME/KEY: modified_base
<222> LOCATION: (404)
<223> OTHER INFORMATION: Wherein n is a, c, g or t
<220> FEATURE:
<221> NAME/KEY: modified_base
<222> LOCATION: (409)
<223> OTHER INFORMATION: Wherein n is a, c, g or t

<400> SEQUENCE: 32

```
gtgtatggga gccctgact cctcacgtgc ctgatctgtg cccttggtcc caggtcaggc      60
ccaccccctg cacctccacc tgccccagcc cctgcctctg ccccaagtgg ggccagctgc    120
cctcacttct ggggtggatg atgtgacctt cctnggggga ctgcggaagg acaagggtt    180
ccctgaagtc ttacggtcca acatcaggac caagtcccat ggacatgctg acagggtccc   240
caggggagac cgtntcanta gggatgtgtg cctggctgtg tacgtgggtg tgcagtgcac   300
gtganaagca cgtggcggct tctgggggcc atgtttgggg aaggaagtgt gcccnccacc   360
cttggagaac ctcagtcccn gtagccccct gccctggcac agcngcatnc acttcaaggg   420
caccctttgg gggttggggt                                                440
```

<210> SEQ ID NO 33
<211> LENGTH: 345
<212> TYPE: DNA
<213> ORGANISM: Homo sapiens
<220> FEATURE:
<221> NAME/KEY: modified_base
<222> LOCATION: (289)
<223> OTHER INFORMATION: Wherein n is a, c, g or t
<220> FEATURE:
<221> NAME/KEY: modified_base
<222> LOCATION: (338)
<223> OTHER INFORMATION: Wherein n is a, c, g or t

<400> SEQUENCE: 33

```
tattttaaca atgtttatta ttcatttatc cctctataga accaccaccc acaccgagga     60
gattatttgg agtgggtccc aacctagggc ctggactctg aaatctaact ccccacttcc    120
ctcattttgt gacttaggtg ggggcatggt tcagtcagaa ctggtgtctc ctattggatc    180
gtgcagaagg aggacctagg cacacacata tggtggccac acccaggagg gttgattggc    240
aggctggaag acaaaagtct cccaataaag gcacttttac ctcaaagang gggtgggagt    300
tggtctgctg ggaatgttgt tgttggggtg gggaagantt atttc                    345
```

<210> SEQ ID NO 34
<211> LENGTH: 440
<212> TYPE: DNA
<213> ORGANISM: Homo sapiens
<220> FEATURE:
<221> NAME/KEY: modified_base
<222> LOCATION: (344)
<223> OTHER INFORMATION: Wherein n is a, c, g or t
<220> FEATURE:
<221> NAME/KEY: modified_base
<222> LOCATION: (369)
<223> OTHER INFORMATION: Wherein n is a, c, g or t
<220> FEATURE:
<221> NAME/KEY: modified_base
<222> LOCATION: (388)
<223> OTHER INFORMATION: Wherein n is a, c, g or t

<400> SEQUENCE: 34

```
tgtaattttt ttattggaaa acaaatatac aacttggaat ggattttgag gcaaattgtg     60
ccataagcag attttaagtg gctaaacaaa gtttaaaaag caagtaacaa taaagaaaa    120
tgtttctggt acaggaccag cagtacaaaa aaatagtgta cgagtacctg gataatacac   180
```

-continued

| | |
|---|---|
| ccgttttgca atagtgcaac ttttaagtac atattgttga ctgtccatag tccacgcaga | 240 |
| gttacaactc cacacttcaa caacaacatg ctgacagttc ctaaagaaaa ctactttaaa | 300 |
| aaaggcataa cccagatgtt ccctcatttg accaactcca tctnagttta gatgtgcaga | 360 |
| agggcttana ttttcccaga gtaagccnca tgcaacatgt tacttgatca attttctaaa | 420 |
| ataaggtttt aggacaatga | 440 |

<210> SEQ ID NO 35
<211> LENGTH: 540
<212> TYPE: DNA
<213> ORGANISM: Homo sapiens
<220> FEATURE:
<221> NAME/KEY: modified_base
<222> LOCATION: (328)
<223> OTHER INFORMATION: Wherein n is a, c, g or t
<220> FEATURE:
<221> NAME/KEY: modified_base
<222> LOCATION: (487)
<223> OTHER INFORMATION: Wherein n is a, c, g or t
<220> FEATURE:
<221> NAME/KEY: modified_base
<222> LOCATION: (520)
<223> OTHER INFORMATION: Wherein n is a, c, g or t

<400> SEQUENCE: 35

| | |
|---|---|
| atagatggaa tttattaagc ttttcacatg tgatagcaca tagttttaat tgcatccaaa | 60 |
| gtactaacaa aaactctagc aatcaagaat ggcagcatgt tattttataa caatcaacac | 120 |
| ctgtggcttt taaaatttgg ttttcataag ataatttata ctgaagtaaa tctagccatg | 180 |
| cttttaaaaa atgctttagg tcactccaag cttggcagtt aacatttggc ataaacaata | 240 |
| ataaacaat cacaatttaa taataacaa atacaacatt gtaggccata atcatataca | 300 |
| gtataaggga aaaggtggta gtgttganta agcagttatt agaatagaat accttggcct | 360 |
| ctatgcaaat atgtctagac actttgattc actcagccct gacattcagt tttcaaagtt | 420 |
| aggaaacagg ttctacagta tcattttaca gtttccaaca cattgaaaac aagtagaaaa | 480 |
| tgatganttg atttttatta atgcattaca tcctcaagan ttatcaccaa cccctcaggt | 540 |

<210> SEQ ID NO 36
<211> LENGTH: 555
<212> TYPE: DNA
<213> ORGANISM: Homo sapiens
<220> FEATURE:
<221> NAME/KEY: modified_base
<222> LOCATION: (81)
<223> OTHER INFORMATION: Wherein n is a, c, g or t
<220> FEATURE:
<221> NAME/KEY: modified_base
<222> LOCATION: (115)
<223> OTHER INFORMATION: Wherein n is a, c, g or t
<220> FEATURE:
<221> NAME/KEY: modified_base
<222> LOCATION: (282)
<223> OTHER INFORMATION: Wherein n is a, c, g or t
<220> FEATURE:
<221> NAME/KEY: modified_base
<222> LOCATION: (292)
<223> OTHER INFORMATION: Wherein n is a, c, g or t
<220> FEATURE:
<221> NAME/KEY: modified_base
<222> LOCATION: (306)
<223> OTHER INFORMATION: Wherein n is a, c, g or t
<220> FEATURE:
<221> NAME/KEY: modified_base
<222> LOCATION: (330)
<223> OTHER INFORMATION: Wherein n is a, c, g or t
<220> FEATURE:
<221> NAME/KEY: modified_base

```
<222> LOCATION: (344)
<223> OTHER INFORMATION: Wherein n is a, c, g or t
<220> FEATURE:
<221> NAME/KEY: modified_base
<222> LOCATION: (346)
<223> OTHER INFORMATION: Wherein n is a, c, g or t
<220> FEATURE:
<221> NAME/KEY: modified_base
<222> LOCATION: (406)
<223> OTHER INFORMATION: Wherein n is a, c, g or t
<220> FEATURE:
<221> NAME/KEY: modified_base
<222> LOCATION: (423)
<223> OTHER INFORMATION: Wherein n is a, c, g or t
<220> FEATURE:
<221> NAME/KEY: modified_base
<222> LOCATION: (439)
<223> OTHER INFORMATION: Wherein n is a, c, g or t
<220> FEATURE:
<221> NAME/KEY: modified_base
<222> LOCATION: (478)
<223> OTHER INFORMATION: Wherein n is a, c, g or t
<220> FEATURE:
<221> NAME/KEY: modified_base
<222> LOCATION: (482)
<223> OTHER INFORMATION: Wherein n is a, c, g or t
<220> FEATURE:
<221> NAME/KEY: modified_base
<222> LOCATION: (522)
<223> OTHER INFORMATION: Wherein n is a, c, g or t
<220> FEATURE:
<221> NAME/KEY: modified_base
<222> LOCATION: (532)
<223> OTHER INFORMATION: Wherein n is a, c, g or t
<220> FEATURE:
<221> NAME/KEY: modified_base
<222> LOCATION: (539)
<223> OTHER INFORMATION: Wherein n is a, c, g or t
<220> FEATURE:
<221> NAME/KEY: modified_base
<222> LOCATION: (542)
<223> OTHER INFORMATION: Wherein n is a, c, g or t
<220> FEATURE:
<221> NAME/KEY: modified_base
<222> LOCATION: (553)
<223> OTHER INFORMATION: Wherein n is a, c, g or t

<400> SEQUENCE: 36
cttcgtgtgc ttgaaaattg gagcctgccc ctcggcccat aagcccttgt tgggaactga      60
gaagtgtata tggggcccaa nctactggtg ccagaacaca gagacagcag cccantgcaa     120
tgctgtcgag cattgcaaac gccatgtgtg gaactaggag gaggaatatt ccatcttggc     180
agaaaccaca gcattggttt ttttctactt gtgtgtctgg gggaatgaac gcacagatct     240
gtttgacttt gttataaaaa tagggctccc ccacctcccc cntttctgtg tnctttattg     300
tagcantgct gtctgcaagg gagcccctan ccccctggcag acananctgc ttcagtgccc     360
ctttcctctc tgctaaatgg atgttgatgc actggaggtc ttttancctg cccttgcatg     420
gcncctgctg gaggaagana aaactctgct ggcatgaccc acagtttctt gactggangc     480
cntcaaccct cttggttgaa gccttgttct gaccctgaca tntgcttggg cnctgggtng     540
gnctgggctt ctnaa                                                      555

<210> SEQ ID NO 37
<211> LENGTH: 280
<212> TYPE: DNA
<213> ORGANISM: Homo sapiens
<220> FEATURE:
<221> NAME/KEY: modified_base
<222> LOCATION: (156)
<223> OTHER INFORMATION: Wherein n is a, c, g or t
<220> FEATURE:
```

<221> NAME/KEY: modified_base
<222> LOCATION: (195)
<223> OTHER INFORMATION: Wherein n is a, c, g or t
<220> FEATURE:
<221> NAME/KEY: modified_base
<222> LOCATION: (243)
<223> OTHER INFORMATION: Wherein n is a, c, g or t

<400> SEQUENCE: 37

| | | |
|---|---|---|
| ccaccgacta taagaactat gccctcgtgt attcctgtac ctgcatcatc caacttttc | 60 |
| acgtggattt tgcttggatc ttggcaagaa accctaatct ccctccagaa acagtggact | 120 |
| ctctaaaaaa tatcctgact tctaataaca ttgatntcaa gaaaatgacg gtcacagacc | 180 |
| aggtgaactg ccccnagctc tcgtaaccag gttctacagg gaggctgcac ccactccatg | 240 |
| ttncttctgc ttcgctttcc cctaccccac ccccgccat | 280 |

<210> SEQ ID NO 38
<211> LENGTH: 303
<212> TYPE: DNA
<213> ORGANISM: Homo sapiens
<220> FEATURE:
<221> NAME/KEY: modified_base
<222> LOCATION: (161)
<223> OTHER INFORMATION: Wherein n is a, c, g or t
<220> FEATURE:
<221> NAME/KEY: modified_base
<222> LOCATION: (170)
<223> OTHER INFORMATION: Wherein n is a, c, g or t
<220> FEATURE:
<221> NAME/KEY: modified_base
<222> LOCATION: (197)
<223> OTHER INFORMATION: Wherein n is a, c, g or t
<220> FEATURE:
<221> NAME/KEY: modified_base
<222> LOCATION: (206)
<223> OTHER INFORMATION: Wherein n is a, c, g or t
<220> FEATURE:
<221> NAME/KEY: modified_base
<222> LOCATION: (216)
<223> OTHER INFORMATION: Wherein n is a, c, g or t
<220> FEATURE:
<221> NAME/KEY: modified_base
<222> LOCATION: (266)
<223> OTHER INFORMATION: Wherein n is a, c, g or t
<220> FEATURE:
<221> NAME/KEY: modified_base
<222> LOCATION: (275)
<223> OTHER INFORMATION: Wherein n is a, c, g or t
<220> FEATURE:
<221> NAME/KEY: modified_base
<222> LOCATION: (280)
<223> OTHER INFORMATION: Wherein n is a, c, g or t
<220> FEATURE:
<221> NAME/KEY: modified_base
<222> LOCATION: (283)
<223> OTHER INFORMATION: Wherein n is a, c, g or t

<400> SEQUENCE: 38

| | |
|---|---|
| catcgagctg gttgtcttct tgcctgccct gtgtcgtaaa atgggggtcc cttactgcat | 60 |
| tatcaaggga aaggcaagac tgggacgtct agtccacagg aagacctgca ccactgtcgc | 120 |
| cttcacacag gtgaactcgg aagacaaagg cgctttggct nagctggtgn aagctatcag | 180 |
| gaccaattac aatgacngat acgatnagat ccgccntcac tggggtagca atgtcctggg | 240 |
| tcctaagtct gtggctcgta tcgccnagct cgaanaggcn aangctaaag aacttgccac | 300 |
| taa | 303 |

<210> SEQ ID NO 39
<211> LENGTH: 300

```
<212> TYPE: DNA
<213> ORGANISM: Homo sapiens
<220> FEATURE:
<221> NAME/KEY: modified_base
<222> LOCATION: (79)
<223> OTHER INFORMATION: Wherein n is a, c, g or t
<220> FEATURE:
<221> NAME/KEY: modified_base
<222> LOCATION: (116)
<223> OTHER INFORMATION: Wherein n is a, c, g or t
<220> FEATURE:
<221> NAME/KEY: modified_base
<222> LOCATION: (138)
<223> OTHER INFORMATION: Wherein n is a, c, g or t
<220> FEATURE:
<221> NAME/KEY: modified_base
<222> LOCATION: (142)
<223> OTHER INFORMATION: Wherein n is a, c, g or t
<220> FEATURE:
<221> NAME/KEY: modified_base
<222> LOCATION: (186)
<223> OTHER INFORMATION: Wherein n is a, c, g or t
<220> FEATURE:
<221> NAME/KEY: modified_base
<222> LOCATION: (224)
<223> OTHER INFORMATION: Wherein n is a, c, g or t
<220> FEATURE:
<221> NAME/KEY: modified_base
<222> LOCATION: (264)
<223> OTHER INFORMATION: Wherein n is a, c, g or t
<220> FEATURE:
<221> NAME/KEY: modified_base
<222> LOCATION: (283)
<223> OTHER INFORMATION: Wherein n is a, c, g or t

<400> SEQUENCE: 39
gactcagcgg ctggtgctct tcctgtgcac aagcccagca ctccaggtcc caaggcattt      60
atcaaatccc accaagatnt ttggcttttg caccgaattc tgggtttggt tccctnaaag     120
aactcattga tgtaaatnac tnaaagtgag gtctgggtac cctttacatg attccccaga     180
cctcanatgg gctaacacgc ttctcttctc cagcagtctt cctntccgtg aagttacctt     240
ccagattgtt acatggaact gaanacaaag ggagcctcag ctngatttaa atctggagca     300

<210> SEQ ID NO 40
<211> LENGTH: 318
<212> TYPE: DNA
<213> ORGANISM: Homo sapiens
<220> FEATURE:
<221> NAME/KEY: modified_base
<222> LOCATION: (268)
<223> OTHER INFORMATION: Wherein n is a, c, g or t
<220> FEATURE:
<221> NAME/KEY: modified_base
<222> LOCATION: (277)
<223> OTHER INFORMATION: Wherein n is a, c, g or t
<220> FEATURE:
<221> NAME/KEY: modified_base
<222> LOCATION: (295)
<223> OTHER INFORMATION: Wherein n is a, c, g or t

<400> SEQUENCE: 40
cccaacacaa tggctgagga caaatcagtt ctctgtgacc agacatgaga aggttgccaa      60
tgggctgttg ggcgaccaag gccttcccgg agtcttcgtc ctctatgagc tctcgcccat     120
gatggtgaag ctgacggaga agcacaggtc cttcacccac ttcctgacag gtgtgtgcgc     180
catcattggg ggcatgttca cagtggctgg actcatcgat tcgctcatct accactcagc     240
acgagccatc cagaaaaaaa ttgatctngg gaagacnacg tagtcaccct cggtncttcc     300
tctgtctcct ctttctcc                                                  318
```

<210> SEQ ID NO 41
<211> LENGTH: 302
<212> TYPE: DNA
<213> ORGANISM: Homo sapiens
<220> FEATURE:
<221> NAME/KEY: modified_base
<222> LOCATION: (107)
<223> OTHER INFORMATION: Wherein n is a, c, g or t
<220> FEATURE:
<221> NAME/KEY: modified_base
<222> LOCATION: (125)
<223> OTHER INFORMATION: Wherein n is a, c, g or t
<220> FEATURE:
<221> NAME/KEY: modified_base
<222> LOCATION: (164)
<223> OTHER INFORMATION: Wherein n is a, c, g or t
<220> FEATURE:
<221> NAME/KEY: modified_base
<222> LOCATION: (186)
<223> OTHER INFORMATION: Wherein n is a, c, g or t
<220> FEATURE:
<221> NAME/KEY: modified_base
<222> LOCATION: (217)
<223> OTHER INFORMATION: Wherein n is a, c, g or t
<220> FEATURE:
<221> NAME/KEY: modified_base
<222> LOCATION: (236)
<223> OTHER INFORMATION: Wherein n is a, c, g or t
<220> FEATURE:
<221> NAME/KEY: modified_base
<222> LOCATION: (247)
<223> OTHER INFORMATION: Wherein n is a, c, g or t
<220> FEATURE:
<221> NAME/KEY: modified_base
<222> LOCATION: (268)
<223> OTHER INFORMATION: Wherein n is a, c, g or t
<220> FEATURE:
<221> NAME/KEY: modified_base
<222> LOCATION: (282)
<223> OTHER INFORMATION: Wherein n is a, c, g or t

<400> SEQUENCE: 41
acttagatgg ggtccgttca ggggatacca gcgttcacat ttttccttt  aagaaagggt     60 cttggcctga atgttcccca tccggacaca ggctgcatgt ctctgtnagt gtcaaagctg    120
ccatnaccat ctcggtaacc tactcttact ccacaatgtc tatnttcact gcagggctct    180
ataatnagtc cataatgtaa atgcctggcc caagacntat ggcctgagtt tatccnaggc    240
ccaaacnatt accagacatt cctcttanat tgaaaacgga tntctttccc ttggcaaaga    300
tc                                                                   302

<210> SEQ ID NO 42
<211> LENGTH: 299
<212> TYPE: DNA
<213> ORGANISM: Homo sapiens
<220> FEATURE:
<221> NAME/KEY: modified_base
<222> LOCATION: (228)
<223> OTHER INFORMATION: Wherein n is a, c, g or t
<220> FEATURE:
<221> NAME/KEY: modified_base
<222> LOCATION: (282)
<223> OTHER INFORMATION: Wherein n is a, c, g or t
<220> FEATURE:
<221> NAME/KEY: modified_base
<222> LOCATION: (298)
<223> OTHER INFORMATION: Wherein n is a, c, g or t

<400> SEQUENCE: 42
cttaataagt ttaaggccaa ggcccgttcc attcttctag caactgacgt tgccagccga     60
ggtttggaca tacctcatgt aaatgtggtt gtcaactttg acattcctac ccattccaag    120

```
gattacatcc atcgagtagg tcgaacagct agagctgggc gctccggaaa ggctattact    180
tttgtcacac agtatgatgt ggaactcttc cagcgcatag aacacttnat tgggaagaaa    240
ctaccaggtt ttccaacaca ggatgatgag gttatgatgc tnacggaacg cgtcgctna    299
```

<210> SEQ ID NO 43
<211> LENGTH: 305
<212> TYPE: DNA
<213> ORGANISM: Homo sapiens
<220> FEATURE:
<221> NAME/KEY: modified_base
<222> LOCATION: (50)
<223> OTHER INFORMATION: Wherein n is a, c, g or t
<220> FEATURE:
<221> NAME/KEY: modified_base
<222> LOCATION: (84)
<223> OTHER INFORMATION: Wherein n is a, c, g or t
<220> FEATURE:
<221> NAME/KEY: modified_base
<222> LOCATION: (225)
<223> OTHER INFORMATION: Wherein n is a, c, g or t
<220> FEATURE:
<221> NAME/KEY: modified_base
<222> LOCATION: (259)
<223> OTHER INFORMATION: Wherein n is a, c, g or t
<220> FEATURE:
<221> NAME/KEY: modified_base
<222> LOCATION: (277)
<223> OTHER INFORMATION: Wherein n is a, c, g or t

<400> SEQUENCE: 43

```
ccaacaatgt caagacagcc gtctgtgaca tcccacctcg tggcctcaan atggcagtca    60
ccttcattgg caatagcaca gccntccggg agctcttcaa gcgcatctcg gagcagttca    120
ctgccatgtt ccgccggaag gccttcctcc actggtacac aggcgagggc atggacaaga    180
tggagttcac cgaggctgag agcaacatga acgacctcgt ctctnagtat cagcagtacc    240
gggatgccac cgcagaaana ggaggaggat ttcggtnagg aggccgaaga aggaggcctg    300
aggca                                                                305
```

<210> SEQ ID NO 44
<211> LENGTH: 399
<212> TYPE: DNA
<213> ORGANISM: Homo sapiens
<220> FEATURE:
<221> NAME/KEY: modified_base
<222> LOCATION: (28)
<223> OTHER INFORMATION: Wherein n is a, c, g or t
<220> FEATURE:
<221> NAME/KEY: modified_base
<222> LOCATION: (78)
<223> OTHER INFORMATION: Wherein n is a, c, g or t
<220> FEATURE:
<221> NAME/KEY: modified_base
<222> LOCATION: (82)
<223> OTHER INFORMATION: Wherein n is a, c, g or t
<220> FEATURE:
<221> NAME/KEY: modified_base
<222> LOCATION: (115)
<223> OTHER INFORMATION: Wherein n is a, c, g or t
<220> FEATURE:
<221> NAME/KEY: modified_base
<222> LOCATION: (134)
<223> OTHER INFORMATION: Wherein n is a, c, g or t
<220> FEATURE:
<221> NAME/KEY: modified_base
<222> LOCATION: (151)
<223> OTHER INFORMATION: Wherein n is a, c, g or t
<220> FEATURE:
<221> NAME/KEY: modified_base
<222> LOCATION: (176)

```
<223> OTHER INFORMATION: Wherein n is a, c, g or t
<220> FEATURE:
<221> NAME/KEY: modified_base
<222> LOCATION: (198)
<223> OTHER INFORMATION: Wherein n is a, c, g or t
<220> FEATURE:
<221> NAME/KEY: modified_base
<222> LOCATION: (250)
<223> OTHER INFORMATION: Wherein n is a, c, g or t
<220> FEATURE:
<221> NAME/KEY: modified_base
<222> LOCATION: (258)
<223> OTHER INFORMATION: Wherein n is a, c, g or t
<220> FEATURE:
<221> NAME/KEY: modified_base
<222> LOCATION: (263)
<223> OTHER INFORMATION: Wherein n is a, c, g or t
<220> FEATURE:
<221> NAME/KEY: modified_base
<222> LOCATION: (269)
<223> OTHER INFORMATION: Wherein n is a, c, g or t
<220> FEATURE:
<221> NAME/KEY: modified_base
<222> LOCATION: (282)
<223> OTHER INFORMATION: Wherein n is a, c, g or t
<220> FEATURE:
<221> NAME/KEY: modified_base
<222> LOCATION: (287)
<223> OTHER INFORMATION: Wherein n is a, c, g or t
<220> FEATURE:
<221> NAME/KEY: modified_base
<222> LOCATION: (332)
<223> OTHER INFORMATION: Wherein n is a, c, g or t
<220> FEATURE:
<221> NAME/KEY: modified_base
<222> LOCATION: (334)
<223> OTHER INFORMATION: Wherein n is a, c, g or t
<220> FEATURE:
<221> NAME/KEY: modified_base
<222> LOCATION: (339)
<223> OTHER INFORMATION: Wherein n is a, c, g or t
<220> FEATURE:
<221> NAME/KEY: modified_base
<222> LOCATION: (344)
<223> OTHER INFORMATION: Wherein n is a, c, g or t
<220> FEATURE:
<221> NAME/KEY: modified_base
<222> LOCATION: (352)
<223> OTHER INFORMATION: Wherein n is a, c, g or t
<220> FEATURE:
<221> NAME/KEY: modified_base
<222> LOCATION: (358)
<223> OTHER INFORMATION: Wherein n is a, c, g or t
<220> FEATURE:
<221> NAME/KEY: modified_base
<222> LOCATION: (364)
<223> OTHER INFORMATION: Wherein n is a, c, g or t
<220> FEATURE:
<221> NAME/KEY: modified_base
<222> LOCATION: (368)
<223> OTHER INFORMATION: Wherein n is a, c, g or t
<220> FEATURE:
<221> NAME/KEY: modified_base
<222> LOCATION: (369)
<223> OTHER INFORMATION: Wherein n is a, c, g or t
<220> FEATURE:
<221> NAME/KEY: modified_base
<222> LOCATION: (388)
<223> OTHER INFORMATION: Wherein n is a, c, g or t

<400> SEQUENCE: 44
tttctgtggg ggaaacctga tctcgacnaa attagagaat tttgtcagcg gtatttcggc      60
tggaacagaa cgaaaacnga tnaatctctg tttcctgtat taaagcaact cgatncccag    120
cagacacagc tccnaattga ttccttcttt ngattagcac aacagggaga agaanatgc     180 ttaacgtatt aagagccnga gactaaacag agctttgaca tgtatgctta ggaaagagaa   240
```

| | | | | | |
|---|---|---|---|---|---|
| agaagcagcn | gcccgcgnaa | ttngaagcng | tttctgttgc | cntgganaaa | gaatttgagc | 300
| ttctttatta | ggccaacgaa | aaaccccgaa | ananaggcnt | tacnatacct | tngaaaantc | 360
| tccngccnna | aaaagaaaga | agctttcnga | ttcttaacc | | | 399

<210> SEQ ID NO 45
<211> LENGTH: 440
<212> TYPE: DNA
<213> ORGANISM: Homo sapiens
<220> FEATURE:
<221> NAME/KEY: modified_base
<222> LOCATION: (272)
<223> OTHER INFORMATION: Wherein n is a, c, g or t
<220> FEATURE:
<221> NAME/KEY: modified_base
<222> LOCATION: (278)
<223> OTHER INFORMATION: Wherein n is a, c, g or t
<220> FEATURE:
<221> NAME/KEY: modified_base
<222> LOCATION: (313)
<223> OTHER INFORMATION: Wherein n is a, c, g or t
<220> FEATURE:
<221> NAME/KEY: modified_base
<222> LOCATION: (323)
<223> OTHER INFORMATION: Wherein n is a, c, g or t
<220> FEATURE:
<221> NAME/KEY: modified_base
<222> LOCATION: (330)
<223> OTHER INFORMATION: Wherein n is a, c, g or t
<220> FEATURE:
<221> NAME/KEY: modified_base
<222> LOCATION: (332)
<223> OTHER INFORMATION: Wherein n is a, c, g or t
<220> FEATURE:
<221> NAME/KEY: modified_base
<222> LOCATION: (383)
<223> OTHER INFORMATION: Wherein n is a, c, g or t
<220> FEATURE:
<221> NAME/KEY: modified_base
<222> LOCATION: (398)
<223> OTHER INFORMATION: Wherein n is a, c, g or t
<220> FEATURE:
<221> NAME/KEY: modified_base
<222> LOCATION: (399)
<223> OTHER INFORMATION: Wherein n is a, c, g or t
<220> FEATURE:
<221> NAME/KEY: modified_base
<222> LOCATION: (401)
<223> OTHER INFORMATION: Wherein n is a, c, g or t
<220> FEATURE:
<221> NAME/KEY: modified_base
<222> LOCATION: (423)
<223> OTHER INFORMATION: Wherein n is a, c, g or t
<220> FEATURE:
<221> NAME/KEY: modified_base
<222> LOCATION: (428)
<223> OTHER INFORMATION: Wherein n is a, c, g or t

<400> SEQUENCE: 45

| | | | | | |
|---|---|---|---|---|---|
| gcgggagcag | aagctaaagc | caaagcccaa | gagagtggca | gtgccagcac | tggtgccagt | 60
| accagtacca | ataacagtgc | cagtgccagt | gccagcacca | gtggtggctt | cagtgctggt | 120
| gccagcctga | ccgccactct | cacatttggg | ctcttcgctg | gccttggtgg | agctggtgcc | 180
| agcaccagtg | gcagctctgg | tgcctgtggt | ttctcctaca | agtgagattt | taggtatctg | 240
| ccttggtttc | agtggggaca | tctgggggctt | anggggcngg | gataaggagc | tggatgattc | 300
| taggaaggcc | cangttggag | aangatgtgn | anagtgtgcc | aagacactgc | ttttggcatt | 360
| ttattccttt | ctgtttgctg | gangtcaatt | gacccttnna | ntttctctta | cttgtgtttt | 420
| canatatngt | taatcctgcc | | | | | 440

<210> SEQ ID NO 46
<211> LENGTH: 472
<212> TYPE: DNA
<213> ORGANISM: Homo sapiens
<220> FEATURE:
<221> NAME/KEY: modified_base
<222> LOCATION: (188)
<223> OTHER INFORMATION: Wherein n is a, c, g or t
<220> FEATURE:
<221> NAME/KEY: modified_base
<222> LOCATION: (195)
<223> OTHER INFORMATION: Wherein n is a, c, g or t
<220> FEATURE:
<221> NAME/KEY: modified_base
<222> LOCATION: (222)
<223> OTHER INFORMATION: Wherein n is a, c, g or t
<220> FEATURE:
<221> NAME/KEY: modified_base
<222> LOCATION: (266)
<223> OTHER INFORMATION: Wherein n is a, c, g or t
<220> FEATURE:
<221> NAME/KEY: modified_base
<222> LOCATION: (402)
<223> OTHER INFORMATION: Wherein n is a, c, g or t
<220> FEATURE:
<221> NAME/KEY: modified_base
<222> LOCATION: (433)
<223> OTHER INFORMATION: Wherein n is a, c, g or t
<220> FEATURE:
<221> NAME/KEY: modified_base
<222> LOCATION: (435)
<223> OTHER INFORMATION: Wherein n is a, c, g or t
<220> FEATURE:
<221> NAME/KEY: modified_base
<222> LOCATION: (453)
<223> OTHER INFORMATION: Wherein n is a, c, g or t
<220> FEATURE:
<221> NAME/KEY: modified_base
<222> LOCATION: (457)
<223> OTHER INFORMATION: Wherein n is a, c, g or t
<220> FEATURE:
<221> NAME/KEY: modified_base
<222> LOCATION: (459)
<223> OTHER INFORMATION: Wherein n is a, c, g or t
<220> FEATURE:
<221> NAME/KEY: modified_base
<222> LOCATION: (461)
<223> OTHER INFORMATION: Wherein n is a, c, g or t

<400> SEQUENCE: 46

```
gctctgtaat ttcacatttt aaaccttccc ttgacctcac attcctcttc ggccacctct      60
gtttctctgt tcctcttcac agcaaaaact gttcaaaaga gttgttgatt actttcattt     120
ccactttctc accccattc tcccctcaat taactctcct tcatcccat gatgccatta      180
tgtggctntt attanagtca ccaaccttat tctccaaaac anaagcaaca aggactttga     240
cttctcagca gcactcagct ctggtncttg aaacacccc gttacttgct attcctccta     300
cctcataaca atctccttcc cagcctctac tgctgccttc tctgagttct tcccagggtc     360
ctaggctcag atgtagtgta gctcaaccct gctacacaaa gnaatctcct gaaagcctgt     420
aaaaatgtcc atncntgtcc tgtgagtgat ctnccangna naataacaaa tt             472
```

<210> SEQ ID NO 47
<211> LENGTH: 550
<212> TYPE: DNA
<213> ORGANISM: Homo sapiens
<220> FEATURE:
<221> NAME/KEY: modified_base
<222> LOCATION: (274)
<223> OTHER INFORMATION: Wherein n is a, c, g or t
<220> FEATURE:
<221> NAME/KEY: modified_base
<222> LOCATION: (359)
<223> OTHER INFORMATION: Wherein n is a, c, g or t
<220> FEATURE:
<221> NAME/KEY: modified_base
<222> LOCATION: (395)
<223> OTHER INFORMATION: Wherein n is a, c, g or t

<400> SEQUENCE: 47

```
ccttcctccg cctggccatc cccagcatgc tcatgctgtg catggagtgg tgggcctatg    60
aggtcgggag cttcctcagt ggtctgtatg aggatggatg acgggactg gtgggaacct    120
gggggccctg tctgggtgca aggcgacagc tgtctttctt caccaggcat cctcggcatg    180
gtggagctgg gcgctcagtc catcgtgtat gaactggcca tcattgtgta catggtccct    240
gcaggcttca gtgtggctgc cagtgtccgg gtangaaacg ctctgggtgc tggagacatg    300
gaagcaggca cggaagtcct ctaccgtttc cctgctgatt acagtgctct ttgctgtanc    360
cttcagtgtc ctgctgttaa gctgtaagga tcacntgggg tacattttta ctaccgaccg    420
agaacatcat taatctggtg gctcaggtgg ttccaattta tgctgtttcc cacctctttg    480
aagctcttgc tgctcaggta cacgccaatt ttgaaaagta acaacgtgc ctcggagtgg    540
gaattctgct                                                          550
```

<210> SEQ ID NO 48
<211> LENGTH: 214
<212> TYPE: DNA
<213> ORGANISM: Homo sapiens
<220> FEATURE:
<221> NAME/KEY: modified_base
<222> LOCATION: (99)
<223> OTHER INFORMATION: Wherein n is a, c, g or t
<220> FEATURE:
<221> NAME/KEY: modified_base
<222> LOCATION: (111)
<223> OTHER INFORMATION: Wherein n is a, c, g or t
<220> FEATURE:
<221> NAME/KEY: modified_base
<222> LOCATION: (188)
<223> OTHER INFORMATION: Wherein n is a, c, g or t
<220> FEATURE:
<221> NAME/KEY: modified_base
<222> LOCATION: (204)
<223> OTHER INFORMATION: Wherein n is a, c, g or t

<400> SEQUENCE: 48

```
agaaggacat aaacaagctg aacctgccca agacgtgtga tatcagcttc tcagatccag    60
acaacctcct caacttcaag ctggtcatct gtcctgatna gggcttctac nagagtggga   120
agtttgtgtt cagttttaag gtgggccagg gttacccgca tgatccccc aaggtgaagt    180
gtgagacnat ggtctatcac cccnacattg acct                                214
```

<210> SEQ ID NO 49
<211> LENGTH: 267
<212> TYPE: DNA
<213> ORGANISM: Homo sapiens
<220> FEATURE:
<221> NAME/KEY: modified_base
<222> LOCATION: (33)
<223> OTHER INFORMATION: Wherein n is a, c, g or t
<220> FEATURE:
<221> NAME/KEY: modified_base
<222> LOCATION: (112)
<223> OTHER INFORMATION: Wherein n is a, c, g or t
<220> FEATURE:
<221> NAME/KEY: modified_base
<222> LOCATION: (123)
<223> OTHER INFORMATION: Wherein n is a, c, g or t
<220> FEATURE:

<221> NAME/KEY: modified_base
<222> LOCATION: (148)
<223> OTHER INFORMATION: Wherein n is a, c, g or t
<220> FEATURE:
<221> NAME/KEY: modified_base
<222> LOCATION: (164)
<223> OTHER INFORMATION: Wherein n is a, c, g or t
<220> FEATURE:
<221> NAME/KEY: modified_base
<222> LOCATION: (198)
<223> OTHER INFORMATION: Wherein n is a, c, g or t
<220> FEATURE:
<221> NAME/KEY: modified_base
<222> LOCATION: (223)
<223> OTHER INFORMATION: Wherein n is a, c, g or t
<220> FEATURE:
<221> NAME/KEY: modified_base
<222> LOCATION: (227)
<223> OTHER INFORMATION: Wherein n is a, c, g or t
<220> FEATURE:
<221> NAME/KEY: modified_base
<222> LOCATION: (231)
<223> OTHER INFORMATION: Wherein n is a, c, g or t
<220> FEATURE:
<221> NAME/KEY: modified_base
<222> LOCATION: (246)
<223> OTHER INFORMATION: Wherein n is a, c, g or t
<220> FEATURE:
<221> NAME/KEY: modified_base
<222> LOCATION: (259)
<223> OTHER INFORMATION: Wherein n is a, c, g or t

<400> SEQUENCE: 49

```
atctgcctaa aatttattca aataatgaaa atnaatctgt tttaagaaat tcagtctttt      60 agttttagg acaactatgc acaaatgtac gatggagaat tcttttgga tnaactctag       120 gtngaggaac ttaatccaac cggagctntt gtgaaggtca gaaacagga gagggaatct     180 tggcaaggaa tggagacnga gtttgcaaat tgcagctaga gtnaatngtt ntaaatggga    240
ctgctnttgt gtctcccang gaaagtt                                         267
```

<210> SEQ ID NO 50
<211> LENGTH: 300
<212> TYPE: DNA
<213> ORGANISM: Homo sapiens
<220> FEATURE:
<221> NAME/KEY: modified_base
<222> LOCATION: (217)
<223> OTHER INFORMATION: Wherein n is a, c, g or t
<220> FEATURE:
<221> NAME/KEY: modified_base
<222> LOCATION: (233)
<223> OTHER INFORMATION: Wherein n is a, c, g or t
<220> FEATURE:
<221> NAME/KEY: modified_base
<222> LOCATION: (252)
<223> OTHER INFORMATION: Wherein n is a, c, g or t
<220> FEATURE:
<221> NAME/KEY: modified_base
<222> LOCATION: (278)
<223> OTHER INFORMATION: Wherein n is a, c, g or t
<220> FEATURE:
<221> NAME/KEY: modified_base
<222> LOCATION: (285)
<223> OTHER INFORMATION: Wherein n is a, c, g or t
<220> FEATURE:
<221> NAME/KEY: modified_base
<222> LOCATION: (294)
<223> OTHER INFORMATION: Wherein n is a, c, g or t
<220> FEATURE:
<221> NAME/KEY: modified_base
<222> LOCATION: (296)
<223> OTHER INFORMATION: Wherein n is a, c, g or t

<400> SEQUENCE: 50

```
gactgggtca aagctgcatg aaaccaggcc ctggcagcaa cctgggaatg gctggaggtg      60
ggagagaacc tgacttctct ttccctctcc ctcctccaac attactggaa ctctgtcctg     120
ttgggatctt ctgagcttgt ttccctgctg ggtgggacag aggacaaagg agaagggagg     180
gtctagaaga ggcagccctt ctttgtcctc tggggtnaat gagcttgacc tanagtagat     240
ggagagacca anagcctctg attttaatt tccataanat gttcnaagta tatntntacc     300
```

<210> SEQ ID NO 51
<211> LENGTH: 300
<212> TYPE: DNA
<213> ORGANISM: Homo sapiens
<220> FEATURE:
<221> NAME/KEY: modified_base
<222> LOCATION: (153)
<223> OTHER INFORMATION: Wherein n is a, c, g or t
<220> FEATURE:
<221> NAME/KEY: modified_base
<222> LOCATION: (190)
<223> OTHER INFORMATION: Wherein n is a, c, g or t
<220> FEATURE:
<221> NAME/KEY: modified_base
<222> LOCATION: (269)
<223> OTHER INFORMATION: Wherein n is a, c, g or t
<220> FEATURE:
<221> NAME/KEY: modified_base
<222> LOCATION: (270)
<223> OTHER INFORMATION: Wherein n is a, c, g or t
<220> FEATURE:
<221> NAME/KEY: modified_base
<222> LOCATION: (287)
<223> OTHER INFORMATION: Wherein n is a, c, g or t

<400> SEQUENCE: 51

```
gggtaaaatc ctgcagcacc cactctggaa aatactgctc ttaattttcc tgaaggtggc      60
cccctatttc tagttggtcc aggattaggg atgtggggta tagggcattt aaatcctctc     120
aagcgctctc caagcacccc cggcctgggg gtnagtttct catcccgcta ctgctgctgg     180
gatcaggttn aataaatgga actcttcctg tctggcctcc aaagcagcct aaaaactgag     240
gggctctgtt agaggggacc tccaccctnn ggaagtccga ggggctnggg aagggtttct     300
```

<210> SEQ ID NO 52
<211> LENGTH: 267
<212> TYPE: DNA
<213> ORGANISM: Homo sapiens
<220> FEATURE:
<221> NAME/KEY: modified_base
<222> LOCATION: (13)
<223> OTHER INFORMATION: Wherein n is a, c, g or t
<220> FEATURE:
<221> NAME/KEY: modified_base
<222> LOCATION: (24)
<223> OTHER INFORMATION: Wherein n is a, c, g or t
<220> FEATURE:
<221> NAME/KEY: modified_base
<222> LOCATION: (28)
<223> OTHER INFORMATION: Wherein n is a, c, g or t
<220> FEATURE:
<221> NAME/KEY: modified_base
<222> LOCATION: (35)
<223> OTHER INFORMATION: Wherein n is a, c, g or t
<220> FEATURE:
<221> NAME/KEY: modified_base
<222> LOCATION: (37)
<223> OTHER INFORMATION: Wherein n is a, c, g or t
<220> FEATURE:
<221> NAME/KEY: modified_base
<222> LOCATION: (49)
<223> OTHER INFORMATION: Wherein n is a, c, g or t
<220> FEATURE:

-continued

```
<221> NAME/KEY: modified_base
<222> LOCATION: (76)
<223> OTHER INFORMATION: Wherein n is a, c, g or t
<220> FEATURE:
<221> NAME/KEY: modified_base
<222> LOCATION: (77)
<223> OTHER INFORMATION: Wherein n is a, c, g or t
<220> FEATURE:
<221> NAME/KEY: modified_base
<222> LOCATION: (95)
<223> OTHER INFORMATION: Wherein n is a, c, g or t
<220> FEATURE:
<221> NAME/KEY: modified_base
<222> LOCATION: (100)
<223> OTHER INFORMATION: Wherein n is a, c, g or t
<220> FEATURE:
<221> NAME/KEY: modified_base
<222> LOCATION: (113)
<223> OTHER INFORMATION: Wherein n is a, c, g or t
<220> FEATURE:
<221> NAME/KEY: modified_base
<222> LOCATION: (133)
<223> OTHER INFORMATION: Wherein n is a, c, g or t
<220> FEATURE:
<221> NAME/KEY: modified_base
<222> LOCATION: (151)
<223> OTHER INFORMATION: Wherein n is a, c, g or t
<220> FEATURE:
<221> NAME/KEY: modified_base
<222> LOCATION: (153)
<223> OTHER INFORMATION: Wherein n is a, c, g or t
<220> FEATURE:
<221> NAME/KEY: modified_base
<222> LOCATION: (156)
<223> OTHER INFORMATION: Wherein n is a, c, g or t
<220> FEATURE:
<221> NAME/KEY: modified_base
<222> LOCATION: (158)
<223> OTHER INFORMATION: Wherein n is a, c, g or t
<220> FEATURE:
<221> NAME/KEY: modified_base
<222> LOCATION: (161)
<223> OTHER INFORMATION: Wherein n is a, c, g or t
<220> FEATURE:
<221> NAME/KEY: modified_base
<222> LOCATION: (173)
<223> OTHER INFORMATION: Wherein n is a, c, g or t
<220> FEATURE:
<221> NAME/KEY: modified_base
<222> LOCATION: (179)
<223> OTHER INFORMATION: Wherein n is a, c, g or t
<220> FEATURE:
<221> NAME/KEY: modified_base
<222> LOCATION: (187)
<223> OTHER INFORMATION: Wherein n is a, c, g or t
<220> FEATURE:
<221> NAME/KEY: modified_base
<222> LOCATION: (209)
<223> OTHER INFORMATION: Wherein n is a, c, g or t
<220> FEATURE:
<221> NAME/KEY: modified_base
<222> LOCATION: (220)
<223> OTHER INFORMATION: Wherein n is a, c, g or t
<220> FEATURE:
<221> NAME/KEY: modified_base
<222> LOCATION: (225)
<223> OTHER INFORMATION: Wherein n is a, c, g or t
<220> FEATURE:
<221> NAME/KEY: modified_base
<222> LOCATION: (227)
<223> OTHER INFORMATION: Wherein n is a, c, g or t
<220> FEATURE:
<221> NAME/KEY: modified_base
<222> LOCATION: (247)
<223> OTHER INFORMATION: Wherein n is a, c, g or t
<220> FEATURE:
<221> NAME/KEY: modified_base
<222> LOCATION: (250)
<223> OTHER INFORMATION: Wherein n is a, c, g or t
```

```
<220> FEATURE:
<221> NAME/KEY: modified_base
<222> LOCATION: (261)
<223> OTHER INFORMATION: Wherein n is a, c, g or t
<220> FEATURE:
<221> NAME/KEY: modified_base
<222> LOCATION: (262)
<223> OTHER INFORMATION: Wherein n is a, c, g or t
<220> FEATURE:
<221> NAME/KEY: modified_base
<222> LOCATION: (266)
<223> OTHER INFORMATION: Wherein n is a, c, g or t

<400> SEQUENCE: 52
aaaatcaact tcntgcatta atanacanat tctanancag gaagtgaana taattttctg    60
cacctatcaa ggaacnnact tgattgcctc tattnaacan atatatcgag ttnctatact   120
tacctgaata ccnccgcata actctcaacc nanatncntc nccatgacac tcnttcttna   180
atgctantcc cgaattcttc attatatcng tgatgttcgn cctgntnata tatcagcaag   240
gtatgtnccn taactgccga nncaang                                      267

<210> SEQ ID NO 53
<211> LENGTH: 401
<212> TYPE: DNA
<213> ORGANISM: Homo sapiens

<400> SEQUENCE: 53
agsctttagc atcatgtaga agcaaactgc acctatggct gagataggtg caatgaccta    60
caagattttg tgttttctag ctgtccagga aaagccatct tcagtcttgc tgacagtcaa   120
agagcaagtg aaaccatttc cagcctaaac tacataaaag cagccgaacc aatgattaaa   180
gacctctaag gctccataat catcattaaa tatgcccaaa ctcattgtga cttttttattt   240 tatatacagg attaaaatca acattaaatc atcttattta catggccatc ggtgctgaaa   300
ttgagcattt taaatagtac agtaggctgg tatacattag gaaatggact gcactggagg   360
caaatagaaa actaaagaaa ttagataggc tggaaatgct t                      401

<210> SEQ ID NO 54
<211> LENGTH: 401
<212> TYPE: DNA
<213> ORGANISM: Homo sapiens

<400> SEQUENCE: 54
cccaacacaa tggataaaaa cacttatagt aaatggggac attcactata atgatctaag    60
aagctacaga ttgtcatagt tgttttcctg ctttacaaaa ttgctccaga tctggaatgc   120
cagtttgacc tttgtcttct ataatatttc cttttttttcc cctctttgaa tctctgtata   180
tttgattctt aactaaaatt gttctcttaa atattctgaa tcctggtaat taaaagtttg   240
ggtgtatttt ctttacctcc aaggaaagaa ctactagcta caaaaaatat tttggaataa   300
gcattgtttt ggtataaggt acatattttg gttgaagaca ccagactgaa gtaaacagct   360
gtgcatccaa tttattatag ttttgtaagt aacaatatgt a                      401

<210> SEQ ID NO 55
<211> LENGTH: 933
<212> TYPE: DNA
<213> ORGANISM: Homo sapiens

<400> SEQUENCE: 55
tttactgctt ggcaaagtac cctgagcatc agcagagatg ccgagatgaa atcagggaac    60
```

-continued

```
tcctagggga tgggtcttct attacctggg aacacctgag ccagatgcct tacaccacga      120
tgtgcatcaa ggaatgcctc cgcctctacg caccggtagt aaactatccc ggttactcga      180
caaacccatc acctttccag atggacgctc cttacctgca ggataactg tgtttatcaa       240 tatttgggct cttcaccaca acccctattt ctgggaagac cctcaggtct ttaacccctt      300
gagattctcc agggaaaatt ctgaaaaaat acatccctat gccttcatac cattctcagc      360
tggattaagg aactgcattg ggcagcattt tgccataatt gagtgtaaag tggcagtggc      420
attaactctg ctccgcttca agctggctcc agaccactca aggccaccca gctgtcgtca      480
agttgcctca agtccaagaa tggaatccat gtgtttgcaa aaaagtttg ctaattttaa       540 gtccttttcg tataagaatt aakgagacaa ttttcctacc aaaggaagaa caaaaggata      600
aatataatac aaaatatatg tatatggttg tttgacaaat tatataactt aggatacttc      660
tgactggttt tgcatccat taacagtaat tttaatttct ttgctgtatc tggtgaaacc       720
cacaaaaaca cctgaaaaaa ctcaagctga gttccaatgc gaagggaaat gattggtttg      780
ggtaactagt ggtagagtgg ctttcaagca tagtttgatc aaaactccac tcagtatctg      840
cattactttt atctctgcaa atatctgcat gatagcttta ttctcagtta tctttcccca      900
taataaaaaa tatctgccaa aaaaaaaaaa aaa                                   933
```

<210> SEQ ID NO 56
<211> LENGTH: 480
<212> TYPE: DNA
<213> ORGANISM: Homo sapiens

<400> SEQUENCE: 56

```
ggctttgaag cattttgtc tgtgctccct gatcttcagg tcaccaccat gaagttctta       60
gcagtcctgg tactcttggg agtttccatc tttctggtct ctgcccagaa tccgacaaca      120
gctgctccag ctgacacgta tccagctact ggtcctgctg atgatgaagc ccctgatgct      180
gaaaccactg ctgctgcaac cactgcgacc actgctgctc ctaccactgc aaccaccgct      240
gcttctacca ctgctcgtaa agacattcca gttttaccca atgggttgg ggatctcccg       300 aatggtagag tgtgtccctg agatggaatc agcttgagtc ttctgcaatt ggtcacaact      360
attcatgctt cctgtgattt catccaacta cttaccttgc ctacgatatc cccttatct       420 ctaatcagtt tattttcttt caaataaaaa ataactatga gcaacaaaaa aaaaaaaaa      480
```

<210> SEQ ID NO 57
<211> LENGTH: 798
<212> TYPE: DNA
<213> ORGANISM: Homo sapiens

<400> SEQUENCE: 57

```
agcctacctg gaaagccaac cagtcctcat aatggacaag atccaccagc tcctcctgtg      60
gactaacttt gtgatatggg aagtgaaaat agttaacacc ttgcacgacc aaacgaacga      120
agatgaccag agtactctta accccttaga actgttttc cttttgtatc tgcaatatgg       180
gatggtattg ttttcatgag cttctagaaa tttcacttgc aagtttattt ttgcttcctg      240
tgttactgcc attcctatt acagtatatt tgagtgaatg attatatttt taaaagtta       300 catgggcctt ttttggttgt cctaaactta caaacattcc actcattctg tttgtaactg      360
tgattataat ttttgtgata atttctggcc tgattgaagg aaatttgaga ggtctgcatt      420
tatatatttt aaatagattt gataggtttt taaattgctt ttttttcataa ggtatttata     480 aagttatttg gggttgtctg ggattgtgtg aaagaaaatt agaacccgc tgtatttaca       540
```

```
tttaccttgg tagtttattt gtggatggca gttttctgta gttttgggga ctgtggtagc      600
tcttggattg ttttgcaaat tacagctgaa atctgtgtca tggattaaac tggcttatgt      660
ggctagaata ggaagagaga aaaaatgaaa tggttgttta ctaattttat actcccatta      720
aaaattttta atgttaagaa aaccttaaat aaacatgatt gatcaatatg gaaaaaaaaa      780
aaaaaaaaaa aaaaaaa                                                    798

<210> SEQ ID NO 58
<211> LENGTH: 280
<212> TYPE: DNA
<213> ORGANISM: Homo sapiens

<400> SEQUENCE: 58
ggggcagctc ctgaccctcc acagccacct ggtcagccac cagctggggc aacgagggtg       60
gaggtcccac tgagcctctc gcctgccccc gccactcgtc tggtgcttgt tgatccaagt      120
cccctgcctg gtcccccaca aggactccca tccaggcccc ctctgccctg cccttgtca      180 tggaccatgg tcgtgaggaa gggctcatgc cccttattta tgggaaccat ttcattctaa     240
cagaataaac cgagaaggaa accagaaaaa aaaaaaaaaa                            280

<210> SEQ ID NO 59
<211> LENGTH: 382
<212> TYPE: DNA
<213> ORGANISM: Homo sapiens

<400> SEQUENCE: 59
aggcgggagc agaagctaaa gccaaagccc aagagagtgg cagtgccagc actggtgcca       60
gtaccagtac caataacagt gccagtgcca gtgccagcac cagtggtggc ttcagtgctg      120
gtgccagcct gaccgccact ctcacatttg ggctcttcgc tggccttggt ggagctggtg      180
ccagcaccag tggcagctct ggtgcctgtg gtttctccta caagtgagat tttagatatt      240
gttaatcctg ccagtctttc tcttcaagcc agggtgcatc ctcagaaacc tactcaacac      300
agcactctag gcagccacta tcaatcaatt gaagttgaca ctctgcatta aatctatttg      360
ccattaaaaa aaaaaaaaa aa                                                382

<210> SEQ ID NO 60
<211> LENGTH: 602
<212> TYPE: DNA
<213> ORGANISM: Homo sapiens

<400> SEQUENCE: 60
tgaagagccg cgcggtggag ctgctgcccg atgggactgc caaccttgcc aagctgcagc       60
ttgtggtgga gaatagtgcc cagcgggtca tccacttggc gggtcagtgg gagaagcacc      120
gggtcccatc tcgtgagta ccgccactcc gaaagctgca ggattgcaga gagctggaat      180
cttctcgacg gctggcagag atccaagaac tgcaccagag tgtccgggcg gctgctgaag      240
aggcccgcag gaaggaggag gtctataagc agctgatgtc agagctggag actctgccca      300
gagatgtgtc ccggctggcc tacacccagc gcatcctgga gatcgtgggc aacatccgga      360
agcagaagga agagatcacc aagatcttgt ctgatacgaa ggagcttcag aaggaaatca      420
actccctatc tgggaagctg gaccggacgt ttgcggtgac tgatgagctt gtgttcaagg      480
atgccaagaa ggacgatgct gttcggaagg cctataagta tctagctgct ctgcacgaga      540
actgcagcca gctcatccag accatcgagg acacaggcac catcatgcgg gaggttcgag      600
``` ac                                                                                                             602

<210> SEQ ID NO 61
<211> LENGTH: 1368
<212> TYPE: DNA
<213> ORGANISM: Homo sapiens
<220> FEATURE:
<221> NAME/KEY: modified_base
<222> LOCATION: (1367)
<223> OTHER INFORMATION: Wherein n is a, c, g or t
<220> FEATURE:
<221> NAME/KEY: modified_base
<222> LOCATION: (1368)
<223> OTHER INFORMATION: Wherein n is a, c, g or t

<400> SEQUENCE: 61

| | | | | | |
|---|---|---|---|---|---|
| ccagtgagcg | cgcgtaatac | gactcactat | agggcgaatt | gggtaccggg | cccccctcg    60 |
| agcggccgcc | cttttttttt | tttttttatt | gatcagaatt | caggctttat | tattgagcaa  120 |
| tgaaaacagc | taaaacttaa | ttccaagcat | gtgtagttaa | agtttgcaaa | gtgggatatt  180 |
| gttcacaaaa | cacattcaat | gtttaaacac | tatttatttg | aagaacaaaa | tatatttaaa  240 |
| attgtttgct | tctaaaaagc | ccatttccct | ccaagtctaa | actttgtaat | ttgatattaa  300 |
| gcaatgaagt | tattttgtac | aatctagtta | aacaagcaga | atagcactag | gcagaataaa  360 |
| aaattgcaca | gacgtatgca | attttccaag | atagcattct | ttaaattcag | ttttcagctt  420 |
| ccaaagattg | gttgcccata | atagacttaa | acatataatg | atggctaaaa | aaaataagta  480 |
| tacgaaaatg | taaaaaagga | aatgtaagtc | cactctcaat | ctcataaaag | gtgagagtaa  540 |
| ggatgctaaa | gcaaataaa  | tgtaggttct | ttttttctgt | ttccgtttat | catgcaatct  600 |
| gcttctttga | tatgccttag | ggttacccat | ttaagttaga | ggttgtaatg | caatggtggg  660 |
| aatgaaaatt | gatcaaatat | acaccttgtc | atttcatttc | aaattgcggg | ctggaaactt  720 |
| ccaaaaaaag | ggtaggcatg | aagaaaaaaa | aaatcmaatc | agaacctctt | caggggtttg  780 |
| kgktctgata | tggcagacar | gatacaagtc | ccaccaggag | atggagcaat | tcaaaataag  840 |
| ggtaatgggc | tgacaaggta | ttattgccag | catgggacag | aatgagcaac | aggctgaaaa  900 |
| gttttttggat | tatatagcac | ctagagtctc | tgatgtaggg | aatttttgtt | agtcaaacat  960 |
| acgctaaact | tccaagggaa | aatctttcag | gtagcctaag | cttgcttttc | tagagtgatg 1020 |
| agttgcattg | ctactgtgat | tttttgaaaa | caaactgggt | ttgtacaagt | gagaaagact 1080 |
| agagagaaag | attttagtct | gtttagcaga | agccattta  | tctgcgtgca | catggatcaa 1140 |
| tatttctgat | cccctatacc | ccaggaaggg | caaaatccca | agaaatgtg  | ttagcaaaat 1200 |
| tggctgatgc | tatcatattg | ctatggacat | tgatcttgcc | caacacaatg | gaattccacc 1260 |
| acactggact | agtggatcca | ctagttctag | agcggccggc | caccgcggtg | gagctccagc 1320 |
| ttttgttccc | tttagtgagg | gttaattgcg | cgcttggcgt | aatcatnn              1368 |

<210> SEQ ID NO 62
<211> LENGTH: 924
<212> TYPE: DNA
<213> ORGANISM: Homo sapiens
<220> FEATURE:
<221> NAME/KEY: modified_base
<222> LOCATION: (7)
<223> OTHER INFORMATION: Wherein n is a, c, g or t
<220> FEATURE:
<221> NAME/KEY: modified_base
<222> LOCATION: (22)
<223> OTHER INFORMATION: Wherein n is a, c, g or t
<220> FEATURE:
<221> NAME/KEY: modified_base -continued

```
<222> LOCATION: (32)
<223> OTHER INFORMATION: Wherein n is a, c, g or t
<220> FEATURE:
<221> NAME/KEY: modified_base
<222> LOCATION: (36)
<223> OTHER INFORMATION: Wherein n is a, c, g or t
<220> FEATURE:
<221> NAME/KEY: modified_base
<222> LOCATION: (40)
<223> OTHER INFORMATION: Wherein n is a, c, g or t
<220> FEATURE:
<221> NAME/KEY: modified_base
<222> LOCATION: (94)
<223> OTHER INFORMATION: Wherein n is a, c, g or t
<220> FEATURE:
<221> NAME/KEY: modified_base
<222> LOCATION: (108)
<223> OTHER INFORMATION: Wherein n is a, c, g or t
<220> FEATURE:
<221> NAME/KEY: modified_base
<222> LOCATION: (117)
<223> OTHER INFORMATION: Wherein n is a, c, g or t
<220> FEATURE:
<221> NAME/KEY: modified_base
<222> LOCATION: (122)
<223> OTHER INFORMATION: Wherein n is a, c, g or t
<220> FEATURE:
<221> NAME/KEY: modified_base
<222> LOCATION: (124)
<223> OTHER INFORMATION: Wherein n is a, c, g or t
<220> FEATURE:
<221> NAME/KEY: modified_base
<222> LOCATION: (130)
<223> OTHER INFORMATION: Wherein n is a, c, g or t
<220> FEATURE:
<221> NAME/KEY: modified_base
<222> LOCATION: (136)
<223> OTHER INFORMATION: Wherein n is a, c, g or t
<220> FEATURE:
<221> NAME/KEY: modified_base
<222> LOCATION: (138)
<223> OTHER INFORMATION: Wherein n is a, c, g or t
<220> FEATURE:
<221> NAME/KEY: modified_base
<222> LOCATION: (142)
<223> OTHER INFORMATION: Wherein n is a, c, g or t
<220> FEATURE:
<221> NAME/KEY: modified_base
<222> LOCATION: (147)
<223> OTHER INFORMATION: Wherein n is a, c, g or t
<220> FEATURE:
<221> NAME/KEY: modified_base
<222> LOCATION: (154)
<223> OTHER INFORMATION: Wherein n is a, c, g or t
<220> FEATURE:
<221> NAME/KEY: modified_base
<222> LOCATION: (157)
<223> OTHER INFORMATION: Wherein n is a, c, g or t
<220> FEATURE:
<221> NAME/KEY: modified_base
<222> LOCATION: (160)
<223> OTHER INFORMATION: Wherein n is a, c, g or t
<220> FEATURE:
<221> NAME/KEY: modified_base
<222> LOCATION: (165)
<223> OTHER INFORMATION: Wherein n is a, c, g or t
<220> FEATURE:
<221> NAME/KEY: modified_base
<222> LOCATION: (169)
<223> OTHER INFORMATION: Wherein n is a, c, g or t
<220> FEATURE:
<221> NAME/KEY: modified_base
<222> LOCATION: (172)
<223> OTHER INFORMATION: Wherein n is a, c, g or t
<220> FEATURE:
<221> NAME/KEY: modified_base
<222> LOCATION: (182)
<223> OTHER INFORMATION: Wherein n is a, c, g or t
<220> FEATURE:
```

```
<221> NAME/KEY: modified_base
<222> LOCATION: (186)
<223> OTHER INFORMATION: Wherein n is a, c, g or t
<220> FEATURE:
<221> NAME/KEY: modified_base
<222> LOCATION: (189)
<223> OTHER INFORMATION: Wherein n is a, c, g or t
<220> FEATURE:
<221> NAME/KEY: modified_base
<222> LOCATION: (193)
<223> OTHER INFORMATION: Wherein n is a, c, g or t
<220> FEATURE:
<221> NAME/KEY: modified_base
<222> LOCATION: (199)
<223> OTHER INFORMATION: Wherein n is a, c, g or t

<400> SEQUENCE: 62
caaaggnaca ggaacagctt gnaaagtact gncatncctn cctgcaggga ccagcccttt      60
gcctccaaaa gcaataggaa atttaaaaga tttncactga gaagggncc acgtttnart      120
tntnaatgtn tcargnanar tnccttncaa atgncrnctn cactnactnr gnatttgggt     180
tnccgnrtnc mgnactatnt caggtttgaa aaactggatc tgccacttat cagttatgtg     240
accttaaaga actccgttaa tttctcagag cctcagtttc cttgtctata agttgggagt     300
aatattaata ctatcatttt tccaaggatt gatgtgaaca ttaatgaggt gaaatgacag     360
atgtgtatca tggttcctaa taaacatcca aaatatagta cttactattg tcattattat     420
tacttgtttg aagctaaaga cctcacaata gaatcccatc cagcccacca gacagagytc     480
tgagttttct agtttggaag agctattaaa taacaacktc tagtgtcaat tctatacttg     540
ttatggtcaa gtaactgggc tcagcatttt acattcattg tctctttaag ttctagcaat     600
gtgaagcagg aactatgatt atattgacta cataaatgaa gaaattgagg ctcagataca     660
ttaagtaatt ctcccagggt cacacagcta gaactggcaa agcctgggat tgatccatga     720
tcttccagca ttgaagaatc ataaatgtaa ataactgcaa ggccttttcc tcagaagagc     780
tcctggtgct tgcaccaacc cactagcact tgttctctac aggggaacat ctgtgggcct     840
gggaatcact gcacgtcgca agagatgttg cttctgatga attattgttc ctgtcagtgg     900
tgtgaaggca aaaaaaaaa aaaa                                             924

<210> SEQ ID NO 63
<211> LENGTH: 1079
<212> TYPE: DNA
<213> ORGANISM: Homo sapiens

<400> SEQUENCE: 63
agtcccaaga actcaataat ctcttatgtt ttcttttgaa gacttatttt aaatattaac      60
tatttcggtg cctgaatgga aaaatataaa cattagctca gagacaatgg ggtacctgtt     120
tggaatccag ctggcagcta taagcaccgt tgaaaactct gacaggcttt gtgcccttt      180
tattaaatgg cctcacatcc tgaatgcagg aatgtgttcg tttaaataaa cattaatctt     240
taatgttgaa ttctgaaaac acaaccataa atcatagttg gtttttctgt gacaatgatc     300
tagtacatta tttcctccac agcaaaccta cctttccaga aggtggaaat tgtatttgca     360
acaatcaggg caaacccac acttgaaaag cattttacaa tattatatct aagttgcaca     420
gaagacccca gtgatcacta ggaaatctac cacagtccag tttttctaat ccaagaaggt     480
caaacttcgg ggaataatgt gtccctcttc tgctgctgct ctgaaaaata ttcgatcaaa     540
acgaagttta caagcagcag ttattccaag attagagttc atttgtgtat cccatgtata     600
ctggcaatgt ttaggtttgc ccaaaaactc ccagacatcc acaatgttgt tgggtaaacc     660
```

```
accacatctg gtaacctctc gatcccttag atttgtatct cctgcaaata taactgtagc    720
tgactctgga gcctcttgca ttttctttaa aaccattttt aactgattca ttcgttccgc    780
agcatgccct ctggtgctct ccaaatggga tgtcataagg caaagctcat ttcctgacac    840
attcacatgc acacataaaa ggtttctcat cattttggta cttggaaaag gaataatctc    900 ttggctttt aatttcactc ttgatttctt caacattata gctgtgaaat atccttcttc    960
atgacctgta ataatctcat aattacttga tctcttcttt aggtagctat aatatggggg   1020
aataacttcc tgtagaaata tcacatctgg gctgtacaaa gctaagtagg aacacaccc    1079

<210> SEQ ID NO 64
<211> LENGTH: 1001
<212> TYPE: DNA
<213> ORGANISM: Homo sapiens

<400> SEQUENCE: 64
gaatgtgcaa cgatcaagtc agggtatctg tggtatccac cactttgagc atttatcgat     60
tctatatgtc aggaacattt caagttatct gttctagcaa ggaaatataa aatacttata    120
gttaactatg gcctatctac agtgcaacta aaaactagat tttattcctt ccacctgtg     180 ggtttgtatt catttaccac cctcttttca ttccctttct cacccacaca ctgtgccggg    240
cctcaggcat atactattct actgtctgtc tctgtaagga ttatcatttt agcttccaca    300
tatgagagaa tgcatgcaaa gttttctctt ccatgtctgg cttatttcac ttaacataat    360
gacctccgct tccatccatg ttatttatat tacccaatag tgttcataaa tatatataca    420
cacatatata ccacattgca tttgtccaat tattcattga cggaaactgg ttaatgttat    480
atcgttgcta ttgtggatag tgctgcaata aacacgcaag tggggatata atttgaagag    540
ttttttttgt tgatgttcctc caaatttaa gattgttttg tctatgtttg tgaaaatggc    600
gttagtattt tcatagagat tgcattgaat ctgtagattg ctttgggtaa gtatggttat    660
tttgatggta ttaattttt cattccatga agatgagatg tctttccatt gtttgtgtcc    720
tctacatttt ctttcatcaa agttttgttg tattttgaa gtagatgtat ttcaccttat    780
agatcaagtg tattccctaa atattttatt tttgtagcta ttgtagatga aattgccttc    840
ttgatttctt tttcacttaa ttcattatta gtgtatgaa atgttatgga tttttatttg    900 ttggtttta atcaaaaact gtattaaact tagagttttt tgtggagttt ttaagttttt    960
ctagatataa gatcatgaca tctaccaaaa aaaaaaaaa a                         1001

<210> SEQ ID NO 65
<211> LENGTH: 575
<212> TYPE: DNA
<213> ORGANISM: Homo sapiens

<400> SEQUENCE: 65
acttgatata aaaaggatat ccataatgaa tattttatac tgcatccttt acattagcca     60
ctaaatacgt tattgcttga tgaagacctt tcacagaatc ctatggattg cagcatttca    120
cttggctact tcatacccat gccttaaaga ggggcagttt ctcaaaagca gaaacatgcc    180
gccagttctc aagttttcct cctaactcca tttgaatgta agggcagctg gcccccaatg    240
tggggaggtc cgaacatttt ctgaattccc attttcttgt tcgcggctaa atgacagttt    300
ctgtcattac ttgattcccc gatctttccc aaaggtgttg atttacaaag aggccagcta    360
atagccagaa atcatgaccc tgaaagagag atgaaatttc aagctgtgag ccaggcagga    420
```

```
gctccagtat ggcaaaggtt cttgagaatc agccatttgg tacaaaaaag attttaaag        480 cttttatgtt ataccatgga gccatagaaa ggctatggat tgtttaagaa ctattttaaa       540
gtgttccaga cccaaaaagg aaaaaaaaaa aaaaa                                   575
```

<210> SEQ ID NO 66
<211> LENGTH: 831
<212> TYPE: DNA
<213> ORGANISM: Homo sapiens

<400> SEQUENCE: 66

```
attgggctcc ttctgctaaa cagccacatt gaaatggttt aaaagcaagt cagatcaggt        60
gatttgtaaa attgtattta tctgtacatg tatgggcttt taattcccac caagaaagag       120
agaaattatc tttttagtta aaaccaaatt tcacttttca aaatatcttc caacttattt       180
attggttgtc actcaattgc ctatatatat atatatatat gtgtgtgtgt gtgtgtgcgc       240
gtgagcgcac gtgtgtgtat gcgtgcgcat gtgtgtgtat gtgtattatc agacataggt       300
ttctaacttt tagatagaag aggagcaaca tctatgccaa atactgtgca ttctacaatg       360
gtgctaatct cagacctaaa tgatactcca tttaatttaa aaaagagttt taaataatta       420
tctatgtgcc tgtatttccc ttttgagtgc tgcacaacat gttaacatat tagtgtaaaa       480
gcagatgaaa caaccacgtg ttctaaagtc tagggattgt gctataatcc ctatttagtt       540
caaaattaac cagaattctt ccatgtgaaa tggaccaaac tcatattatt gttatgtaaa       600
tacagagttt taatgcagta tgacatccca caggggaaaa gaatgtctgt agtgggtgac       660
tgttatcaaa tattttatag aatacaatga acggtgaaca gactggtaac ttgtttgagt       720
tcccatgaca gatttgagac ttgtcaatag caaatcattt ttgtatttaa attttttgtac      780 tgatttgaaa aacatcatta aatatcttta aaagtaaaaa aaaaaaaaa a                 831
```

<210> SEQ ID NO 67
<211> LENGTH: 590
<212> TYPE: DNA
<213> ORGANISM: Homo sapiens

<400> SEQUENCE: 67

```
gtgctctgtg tattttttta ctgcattaga cattgaatag taatttgcgt taagatacgc        60
ttaaaggctc tttgtgacca tgtttcccctt tgtagcaata aatgttttt tacgaaaact       120 ttctccctgg attagcagtt taaatgaaac agagttcatc aatgaaatga gtatttaaaa       180
taaaaatttg ccttaatgta tcagttcagc tcacaagtat tttaagatga ttgagaagac       240
ttgaattaaa gaaaaaaaaa ttctcaatca tattttaaaa atataagact aaaattgttt       300
ttaaaacaca tttcaaatag aagtgagttt gaactgacct tatttatact cttttttaagt      360 ttgttccttt tccctgtgcc tgtgtcaaat cttcaagtct tgctgaaaat acatttgata       420
caaagttttc tgtagttgtg ttagttcttt tgtcatgtct gtttttggct gaagaaccaa       480
gaagcagact tttcttttaa aagaattatt tctctttcaa atatttctat ccttttaaaa       540
aaattccttt ttatggctta tataacctaca tatttaaaaa aaaaaaaaaa                 590
```

COMPOUNDS FOR DIAGNOSIS OF BREAST CANCER AND METHODS FOR THEIR USE

REFERENCE TO RELATED APPLICATIONS

This application is a continuation-in-part of U.S. patent application Ser. No. 08/998,255, filed Dec. 24, 1997, now abandoned.

TECHNICAL FIELD

The present invention relates generally to compositions and methods for the treatment of breast cancer. The invention is more particularly related to polypeptides comprising at least a portion of a protein that is preferentially expressed in breast tumor tissue and to DNA molecules encoding such polypeptides. Such polypeptides may be used in vaccines and pharmaceutical compositions for treatment of breast cancer.

BACKGROUND OF THE INVENTION

Breast cancer is a significant health problem for women in the United States and throughout the world. Although, advances have been made in detection and treatment of the disease, breast cancer remains the second leading cause of cancer- related deaths in women, affecting more than 180,000 women in the United States each year. For women in North America, the life-time odds of getting breast cancer are now one in eight.

No vaccine or other universally successful method for the prevention or treatment of breast cancer is currently available. Management of the disease currently relies on a combination of early diagnosis (through routine breast screening procedures) and aggressive treatment, which may include one or more of a variety of treatments such as surgery, radiotherapy, chemotherapy and hormone therapy. The course of treatment for a particular breast cancer is often selected based on a variety of prognostic parameters, including an analysis of specific tumor markers. See, e.g. Porter-Jordan and Lippman, *Breast Cancer* 8:73–100 (1994). However, the use of established markers often leads to a result that is difficult to interpret, and the high mortality observed in breast cancer patients indicates that improvements are needed in the treatment, diagnosis and prevention of the disease.

Accordingly, there is a need in the art for improved methods for therapy and diagnosis of breast cancer. The present invention fulfills these needs and further provides other related advantages.

SUMMARY OF THE INVENTION

The present invention provides methods for immunodiagnosis of breast cancer, together with kits for use in such methods. Polypeptides are disclosed which comprise at least an immunogenic portion of a breast tumor protein or a variant thereof, wherein the breast tumor protein comprises an amino acid sequence encoded by a DNA molecule comprising a sequence selected from the group consisting of: (a) nucleotide sequences recited in SEQ ID NOS: 1–67; (b) complements of said nucleotide sequences; and (c) sequences that hybridize to a sequence of (a) or (b) under moderately stringent conditions. Such polypeptides may be usefully employed in the diagnosis and monitoring of breast cancer. In one specific aspect of the present invention, methods are provided for detecting breast cancer in a patient, comprising: (a) contacting a biological sample obtained from a patient with a binding agent that is capable of binding to one of the above polypeptides; and (b) detecting in the sample a protein or polypeptide that binds to the binding agent. In preferred embodiments, the binding agent is an antibody, most preferably a monoclonal antibody.

In related aspects, methods are provided for monitoring the progression of breast cancer in a patient, comprising: (a) contacting a biological sample obtained from a patient with a binding agent that is capable of binding to one of the above polypeptides; (b) determining in the sample an amount of a protein or polypeptide that binds to the binding agent; (c) repeating steps (a) and (b); and comparing the amounts of polypeptide detected in steps (b) and (c).

Within related aspects, the present invention provides antibodies, preferably monoclonal antibodies, that bind to the inventive polypeptides, as well as diagnostic kits comprising such antibodies, and methods of using such antibodies to inhibit the development of breast cancer.

The present invention further provides methods for detecting breast cancer comprising: (a) obtaining a biological sample from a patient; (b) contacting the sample with a first and a second oligonucleotide primer in a polymerase chain reaction, at least one of the oligonucleotide primers being specific for a DNA molecule that encodes one of the above polypeptides; and (c) detecting in the sample a DNA sequence that amplifies in the presence of the first and second oligonucleotide primers. In a preferred embodiment, at least one of the oligonucleotide primers comprises at least about 10 contiguous nucleotides of a DNA molecule having a partial sequence selected from the group consisting of SEQ ID NOS: 1–67.

In a further aspect, the present invention provides a method for detecting breast cancer in a patient comprising: (a) obtaining a biological sample from the patient; (b) contacting the sample with an oligonucleotide probe specific for a DNA molecule that encodes one of the above polypeptides; and (c) detecting in the sample a DNA sequence that hybridizes to the oligonucleotide probe. Preferably, the oligonucleotide probe comprises at least about 15 contiguous nucleotides of a DNA molecule having a partial sequence selected from the group consisting of SEQ ID NOS: 1–67.

In related aspects, diagnostic kits comprising the above oligonucleotide probes or primers are provided.

These and other aspects of the present invention will become apparent upon reference to the following detailed description. All references disclosed herein are hereby incorporated by reference in their entirety as if each was incorporated individually.

DETAILED DESCRIPTION OF THE INVENTION

As noted above, the present invention is generally directed to compositions and methods for the diagnosis and monitoring of breast cancer. The inventive compositions are generally isolated polypeptides that comprise at least a portion of a breast tumor protein. Also included within the present invention are molecules (such as an antibody or fragment thereof) that bind to the inventive polypeptides. Such molecules are referred to herein as "binding agents."

In particular, the subject invention discloses polypeptides comprising at least a portion of a human breast tumor protein, or a variant thereof, wherein the breast tumor protein includes an amino acid sequence encoded by a DNA molecule comprising a sequence selected from the group consisting of: nucleotide sequences recited in SEQ ID NOS: 1–67, the complements of said nucleotide sequences, and variants thereof. As used herein, the term "polypeptide" encompasses amino acid chains of any length, including full length proteins, wherein the amino acid residues are linked by covalent peptide bonds. Thus, a polypeptide comprising a portion of one of the above breast proteins may consist entirely of the portion, or the portion may be present within a larger polypeptide that contains additional sequences. The additional sequences may be derived from the native protein or may be heterologous, and such sequences may be immunoreactive and/or antigenic.

As used herein, an "immunogenic portion" of a human breast tumor protein is a portion that is capable of eliciting an immune response in a patient inflicted with breast cancer and as such binds to antibodies present within sera from a breast cancer patient. Such immunogenic portions generally comprise at least about 5 amino acid residues, more preferably at least about 10, and most preferably at least about 20 amino acid residues. Immunogenic portions of the proteins described herein may thus be identified in antibody binding assays. Such assays may generally be performed using any of a variety of means known to those of ordinary skill in the art, as described, for example, in Harlow and Lane, *Antibodies: A Laboratory Manual*, Cold Spring Harbor Laboratory, Cold Spring Harbor, N.Y., 1988. For example, a polypeptide may be immobilized on a solid support (as described below) and contacted with patient sera to allow binding of antibodies within the sera to the immobilized polypeptide. Unbound sera may then be removed and bound antibodies detected using, for example, $^{125}$I-labeled Protein A. Alternatively, a polypeptide may be used to generate monoclonal and polyclonal antibodies for use in detection of the polypeptide in blood or other fluids of breast cancer patients. Methods for preparing and identifying immunogenic portions of antigens of known sequence are well known in the art and include those summarized in Paul, *Fundamental Immunology*, 3$^{rd}$., Raven Press, 1993, pp. 243–247.

The compositions and methods of the present invention also encompass variants of the above polypeptides and DNA molecules. A polypeptide "variant," as used herein, is a polypeptide that differs from the recited polypeptide only in conservative substitutions and/or modifications, such that the therapeutic, antigenic and/or immunogenic properties of the polypeptide are retained. Polypeptide variants preferably exhibit at least about 70%, more preferably at least about 90% and most preferably at least about 95% identity to the identified polypeptides. The identity of polypeptides may be determined using computer algorithms well known to those of skill in the art, such as Megalign, using default parameters. For breast tumor polypeptides with immunoreactive properties, variants may, alternatively, be identified by modifying the amino acid sequence of one of the above polypeptides, and evaluating the immunoreactivity of the modified polypeptide. For breast tumor polypeptides useful for the generation of diagnostic binding agents, a variant may be identified by evaluating a modified polypeptide for the ability to generate antibodies that detect the presence or absence of breast cancer. Such modified sequences may be prepared and tested using, for example, the representative procedures described herein.

As used herein, a "conservative substitution" is one in which an amino acid is substituted for another amino acid that has similar properties, such that one skilled in the art of peptide chemistry would expect the secondary structure and hydropathic nature of the polypeptide to be substantially unchanged. In general, the following groups of amino acids represent conservative changes: (1) ala, pro, gly, glu, asp, gin, asn, ser, thr; (2) cys, ser, tyr, thr; (3) val, ile, leu, met, ala, phe; (4) lys, arg, his; and (5) phe, tyr, tip, his.

Variants of the inventive polypeptides may also, or alternatively, contain other modifications, including the deletion or addition of amino acids that have minimal influence on the antigenic properties, secondary structure and hydropathic nature of the polypeptide. For example, a polypeptide may be conjugated to a signal (or leader) sequence at the N-terminal end of the protein which co-translationally or post-translationally directs transfer of the protein. The polypeptide may also be conjugated to a linker or other sequence for ease of synthesis, purification or identification of the polypeptide (e.g., poly-His), or to enhance binding of the polypeptide to a solid support. For example, a polypeptide may be conjugated to an immunoglobulin Fc region.

A nucleotide "variant" is a sequence that differs from the recited nucleotide sequence in having one or more nucleotide deletions, substitutions or additions. Such modifications may be readily introduced using standard mutagenesis techniques, such as oligonucleotide-directed site-specific mutagenesis as taught, for example, by Adelman et al. (*DNA*, 2:183, 1983). Nucleotide variants may be naturally occurring allelic variants, or non-naturally occurring variants. Variant nucleotide sequences preferably exhibit at least about 70%, more preferably at least about 80% and most preferably at least about 90% identity to the recited sequence. The identity of nucleotide sequences may be determined by comparing sequences using computer algorithms well known to those of skill in the art, such as Megalign, using default parameters. Such variant nucleotide sequences will generally hybridize to the recite nucleotide sequence under moderately stringent conditions. As used herein, "moderately stringent conditions" refers to prewashing in a solution of 6×SSC, 0.2% SDS; hybridizing at 65° C., 6×SSC, 0.2% SDS overnight; followed by two washes of 30 minutes each in 1×SSC, 0.1% SDS at 65° C. and two washes of 30 minutes each in 0.2×SSC, 0.1% SDS at 65° C.

The breast tumor proteins of the present invention, and DNA molecules encoding such proteins, may be isolated from breast tumor tissue using any of a variety of methods well known in the art. DNA sequences corresponding to a gene (or a portion thereof) encoding one of the inventive breast tumor proteins may be isolated from a breast tumor cDNA library using a subtraction technique as described in detail below. Examples of such DNA sequences are provided in SEQ ID NOS: 1–67. Partial DNA sequences thus obtained may be used to design oligonucleotide primers for the amplification of full-length DNA sequences in a polymerase chain reaction (PCR), using techniques well known in the art (see, for example, Mullis et al., *Cold Spring Harbor Symp. Quant. Biol.*, 51:263, 1987; Erlich ed., *PCR Technology*, Stockton Press, N.Y., 1989). Once a DNA sequence encoding a polypeptide is obtained, any of the above modifications may be readily introduced using standard mutagenesis techniques, such as oligonucleotide-directed site-specific mutagenesis as taught, for example, by Adelman et al. (*DNA*, 2:183, 1983).

The breast tumor polypeptides disclosed herein may also be generated by synthetic or recombinant means. Synthetic polypeptides having fewer than about 100 amino acids, and generally fewer than about 50 amino acids, may be generated using techniques well known to those of ordinary skill in the art. For example, such polypeptides may be synthesized using any of the commercially available solid-phase techniques, such as the Merrifield solid-phase synthesis method, where amino acids are sequentially added to a growing amino acid chain (see, for example, Merrifield, *J. Am. Chem. Soc.* 85:2149–2146, 1963). Equipment for automated synthesis of polypeptides is commercially available from suppliers such as Perkin Elmer/Applied BioSystems Division (Foster City, Calif.), and may be operated according to the manufacturer's instructions.

Alternatively, any of the above polypeptides may be produced recombinantly by inserting a DNA sequence that encodes the polypeptide into an expression vector and expressing the protein in an appropriate host. Any of a variety of expression vectors known to those of ordinary skill in the art may be employed to express recombinant polypeptides of this invention. Expression may be achieved in any appropriate host cell that has been transformed or transfected with an expression vector containing a DNA molecule that encodes a recombinant polypeptide. Suitable host cells include prokaryotes, yeast and higher eukaryotic cells. Preferably, the host cells employed are *E. coli*, yeast or a mammalian cell line, such as CHO cells. The DNA sequences expressed in this manner may encode naturally occurring polypeptides, portions of naturally occurring polypeptides, or other variants thereof.

In general, regardless of the method of preparation, the polypeptides disclosed herein are prepared in an isolated, substantially pure form (i.e., the polypeptides are homogenous as determined by amino acid composition and primary sequence analysis). Preferably, the polypeptides are at least about 90% pure, more preferably at least about 95% pure and most preferably at least about 99% pure. In certain preferred embodiments, described in more detail below, the substantially pure polypeptides are incorporated into pharmaceutical compositions or vaccines for use in one or more of the methods disclosed herein.

In a related aspect, the present invention provides fusion proteins comprising a first and a second inventive polypeptide or, alternatively, a polypeptide of the present invention and a known breast tumor antigen, together with variants of such fusion proteins.

A DNA sequence encoding a fusion protein of the present invention is constructed using known recombinant DNA techniques to assemble separate DNA sequences encoding the first and second polypeptides into an appropriate expression vector. The 3' end of a DNA sequence encoding the first polypeptide is ligated, with or without a peptide linker, to the 5' end of a DNA sequence encoding the second polypeptide so that the reading frames of the sequences are in phase to permit mRNA translation of the two DNA sequences into a single fusion protein that retains the biological activity of both the first and the second polypeptides.

A peptide linker sequence may be employed to separate the first and the second polypeptides by a distance sufficient to ensure that each polypeptide folds into its secondary and tertiary structures. Such a peptide linker sequence is incorporated into the fusion protein using standard techniques well known in the art. Suitable peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Preferred peptide linker sequences contain Gly, Asn and Ser residues. Other near neutral amino acids, such as Thr and Ala may also be used in the linker sequence. Amino acid sequences which may be usefully employed as linkers include those disclosed in Maratea et al., *Gene* 40:39–46, 1985; Murphy et al., *Proc.* *Natl. Acad. Sci. USA* 83:8258–8262, 1986; U.S. Pat. Nos. 4,935,233 and 4,751,180. The linker sequence may be from 1 to about 50 amino acids in length. Peptide sequences are not required when the first and second polypeptides have non-essential N-terminal amino acid regions that can be used to separate the functional domains and prevent steric interference.

The ligated DNA sequences are operably linked to suitable transcriptional or translational regulatory elements. The regulatory elements responsible for expression of DNA are located only 5' to the DNA sequence encoding the first polypeptides. Similarly, stop codons require to end translation and transcription termination signals are only present 3' to the DNA sequence encoding the second polypeptide.

Fusion proteins are also provided that comprise a polypeptide of the present invention together with an unrelated immunogenic protein. Preferably the immunogenic protein is capable of eliciting a recall response. Examples of such proteins include tetanus, tuberculosis and hepatitis proteins (see, for example, Stoute et al. *New Engl. J Med.,* 336:86–91(1997)).

Polypeptides of the present invention that comprise an immunogenic portion of a breast tumor protein may generally be used for immunotherapy of breast cancer, wherein the polypeptide stimulates the patient's own immune response to breast tumor cells. In further aspects, the present invention provides methods for using one or more of the immunoreactive polypeptides encoded by a DNA molecule having a partial sequence provided in SEQ ID NOS: 1–67 (or fusion proteins comprising one or more such polypeptides and/or DNA encoding such polypeptides) for immunotherapy of breast cancer in a patient. As used herein, a "patient" refers to any warm-blooded animal, preferably a human. A patient may be afflicted with a disease, or may be free of detectable disease. Accordingly, the above immunoreactive polypeptides (or fusion proteins or DNA molecules encoding such polypeptides) may be used to treat breast cancer or to inhibit the development of breast cancer. The polypeptides may be administered either prior to or following surgical removal of primary tumors and/or treatment by administration of radiotherapy and conventional chemotherapeutic drugs.

In these aspects, the polypeptide or fusion protein is generally present within a pharmaceutical composition and/or a vaccine. Pharmaceutical compositions may comprise one or more polypeptides, each of which may contain one or more of the above sequences (or variants thereof), and a physiologically acceptable carrier. The vaccines may comprise one or more of such polypeptides and a non-specific immune response enhancer, wherein the non-specific immune response enhancer is capable of eliciting or enhancing an immune response to an exogenous antigen. Examples of non-specific-immune response enhancers include adjuvants, biodegradable microspheres (e.g., polylactic galactide) and liposomes (into which the polypeptide is incorporated). Pharmaceutical compositions and vaccines may also contain other epitopes of breast tumor antigens, either incorporated into a combination polypeptide (i.e., a single polypeptide that contains multiple epitopes) or present within a separate polypeptide.

Alternatively, a pharmaceutical composition or vaccine may contain DNA encoding one or more of the above polypeptides, such that the polypeptide is generated in situ. In such pharmaceutical compositions and vaccines, the DNA may be present within any of a variety of delivery systems known to those of ordinary skill in the art, including nucleic acid expression systems, bacteria and viral expression systems. Appropriate nucleic acid expression systems contain the necessary DNA sequences for expression in the patient (such as a suitable promoter). Bacterial delivery systems involve the administration of a bacterium (such as *Bacillus-Calmette-Guerrin*) that expresses an epitope of a breast tumor cell antigen on its cell surface. In a preferred embodiment, the DNA may be introduced using a viral expression system (e.g., vaccinia or other pox virus, retrovirus, or adenovirus), which may involve the use of a non-pathogenic (defective), replication competent virus. Suitable systems are disclosed, for example, in Fisher-Hoch et al., *PNAS* 86:317–321, 1989; Flexner et al., *Ann. N.Y Acad. Sci.* 569:86–103, 1989; Flexner et al., *Vaccine* 8:17–21, 1990; U.S. Pat. Nos. 4,603,112, 4,769,330, and 5,017,487; WO 89/01973; U.S. Pat. No. 4,777,127; GB 2,200,651; EP 0,345,242; WO 91/02805; Berkner, *Biotechniques* 6:616–627, 1988; Rosenfeld et al., *Science* 252:431–434, 1991; Kolls et al., *PNAS* 91:215–219, 1994; Kass-Eisler et al., *PNAS* 90:11498–11502, 1993; Guzman et al., *Circulation* 88:2838–2848, 1993; and Guzman et al., *Cir. Res.* 73:1202–1207, 1993. Techniques for incorporating DNA into such expression systems are well known to those of ordinary skill in the art. The DNA may also be "naked," as described, for example, in published PCT application WO 90/11092, and Ulmer et al., *Science* 259:1745–1749, 1993, reviewed by Cohen, *Science* 259:1691–1692, 1993. The uptake of naked DNA may be increased by coating the DNA onto biodegradable beads, which are efficiently transported into the cells.

Routes and frequency of administration, as well as dosage, will vary from individual to individual and may parallel those currently being used in immunotherapy of other diseases. In general, the pharmaceutical compositions and vaccines may be administered by injection (e.g., intracutaneous, intramuscular, intravenous or subcutaneous), intranasally (e.g., by aspiration) or orally. Between 1 and 10 doses may be administered over a 3–24 week period. Preferably, 4 doses are administered, at an interval of 3 months, and booster administrations may be given periodically thereafter. Alternate protocols may be appropriate for individual patients. A suitable dose is an amount of polypeptide or DNA that is effective to raise an immune response (cellular and/or humoral) against breast tumor cells in a treated patient. A suitable immune response is at least 10–50% above the basal (i.e., untreated) level. In general, the amount of polypeptide present in a dose (or produced in situ by the DNA in a dose) ranges from about 1 pg to about 100 mg per kg of host, typically from about 10 pg to about 1 mg, and preferably from about 100 pg to about 1 $\mu$g. Suitable dose sizes will vary with the size of the patient, but will typically range from about 0.01 mL to about 5 mL.

While any suitable carrier known to those of ordinary skill in the art may be employed in the pharmaceutical compositions of this invention, the type of carrier will vary depending on the mode of administration. For parenteral administration, such as subcutaneous injection, the carrier preferably comprises water, saline, alcohol, a lipid, a wax and/or a buffer. For oral administration, any of the above carriers or a solid carrier, such as mannitol, lactose, starch, magnesium stearate, sodium saccharine, talcum, cellulose, glucose, sucrose, and/or magnesium carbonate, may be employed. Biodegradable microspheres (e.g., polylactic glycolide) may also be employed as carriers for the pharmaceutical compositions of this invention. Suitable biodegradable microspheres are disclosed, for example, in U.S. Pat. Nos. 4,897,268 and 5,075,109.

Any of a variety of non-specific immune response enhancers may be employed in the vaccines of this invention. For example, an adjuvant may be included. Most adjuvants contain a substance designed to protect the antigen from rapid catabolism, such as aluminum hydroxide or mineral oil, and a nonspecific stimulator of immune response, such as lipid A, *Bordella pertussis* or *Mycobacterium tuberculosis*. Such adjuvants are commercially available as, for example, Freund's Incomplete Adjuvant and Complete Adjuvant (Difco Laboratories, Detroit, Mich.) and Merck Adjuvant 65 (Merck and Company, Inc., Rahway, N.J.).

Polypeptides disclosed herein may also be employed in ex vivo treatment of breast cancer. For example, cells of the immune system, such as T cells, may be isolated from the peripheral blood of a patient, using a commercially available cell separation system, such as CellPro Incorporated's (Bothell, Wash.) CEPRATE™ system (see U.S. Pat. No. 5,240,856; U.S. Pat. No. 5,215,926; WO 89/06280; WO 91/16116 and WO 92/07243). The separated cells are stimulated with one or more of the immunoreactive polypeptides contained within a delivery vehicle, such as a microsphere, to provide antigen-specific T cells. The population of tumor antigen-specific T cells is then expanded using standard techniques and the cells are administered back to the patient.

Polypeptides of the present invention may also, or alternatively, be used to generate binding agents, such as antibodies or fragments thereof, that are capable of detecting metastatic human breast tumors. Binding agents of the present invention may generally be prepared using methods known to those of ordinary skill in the art, including the representative procedures described herein. Binding agents are capable of differentiating between patients with and without breast cancer, using the representative assays described herein. In other words, antibodies or other binding agents raised against a breast tumor protein, or a suitable portion thereof, will generate a signal indicating the presence of primary or metastatic breast cancer in at least about 20% of patients afflicted with the disease, and will generate a negative signal indicating the absence of the disease in at least about 90% of individuals without primary or metastatic breast cancer. Suitable portions of such breast tumor proteins are portions that are able to generate a binding agent that indicates the presence of primary or metastatic breast cancer in substantially all (i.e., at least about 80%, and preferably at least about 90%) of the patients for which breast cancer would be indicated using the full length protein, and that indicate the absence of breast cancer in substantially all of those samples that would be negative when tested with full length protein. The representative assays described below, such as the two-antibody sandwich assay, may generally be employed for evaluating the ability of a binding agent to detect metastatic human breast tumors.

The ability of a polypeptide prepared as described herein to generate antibodies capable of detecting primary or metastatic human breast tumors may generally be evaluated by raising one or more antibodies against the polypeptide (using, for example, a representative method described herein) and determining the ability of such antibodies to detect such tumors in patients. This determination may be made by assaying biological samples from patients with and without primary or metastatic breast cancer for the presence of a polypeptide that binds to the generated antibodies. Such test assays may be performed, for example, using a representative procedure described below. Polypeptides that generate antibodies capable of detecting at least 20% of primary or metastatic breast tumors by such procedures are considered to be useful in assays for detecting primary or metastatic human breast tumors. Polypeptide specific antibodies may be used alone or in combination to improve sensitivity.

Polypeptides capable of detecting primary or metastatic human breast tumors may be used as markers for diagnosing breast cancer or for monitoring disease progression in patients. In one embodiment, breast cancer in a patient may be diagnosed by evaluating a biological sample obtained from the patient for the level of one or more of the above polypeptides, relative to a predetermined cut-off value. As used herein, suitable "biological samples" include blood, sera and urine.

The level of one or more of the above polypeptides may be evaluated using any binding agent specific for the polypeptide(s). A "binding agent," in the context of this invention, is any agent (such as a compound or a cell) that binds to a polypeptide as described above. As used herein, "binding" refers to a noncovalent association between two separate molecules (each of which may be free (i.e., in solution) or present on the surface of a cell or a solid support), such that a "complex" is formed. Such a complex may be free or immobilized (either covalently or noncovalently) on a support material. The ability to bind may generally be evaluated by determining a binding constant for the formation of the complex. The binding constant is the value obtained when the concentration of the complex is divided by the product of the component concentrations. In general, two compounds are said to "bind" in the context of the present invention when the binding constant for complex formation exceeds about $10^3$ L/mol. The binding constant may be determined using methods well known to those of ordinary skill in the art.

Any agent that satisfies the above requirements may be a binding agent. For example, a binding agent may be a ribosome with or without a peptide component, an RNA molecule or a peptide. In a preferred embodiment, the binding partner is an antibody, or a fragment thereof. Such antibodies may be polyclonal, or monoclonal. In addition, the antibodies may be single chain, chimeric, CDR-grafted or humanized. Antibodies may be prepared by the methods described herein and by other methods well known to those of skill in the art.

There are a variety of assay formats known to those of ordinary skill in the art for using a binding partner to detect polypeptide markers in a sample. See, e.g., Harlow and Lane, *Antibodies: A Laboratory Manual*, Cold Spring Harbor Laboratory, 1988. In a preferred embodiment, the assay involves the use of binding partner immobilized on a solid support to bind to and remove the polypeptide from the remainder of the sample. The bound polypeptide may then be detected using a second binding partner that contains a reporter group. Suitable second binding partners include antibodies that bind to the binding partner/polypeptide complex. Alternatively, a competitive assay may be utilized, in which a polypeptide is labeled with a reporter group and allowed to bind to the immobilized binding partner after incubation of the binding partner with the sample. The extent to which components of the sample inhibit the binding of the labeled polypeptide to the binding partner is indicative of the reactivity of the sample with the immobilized binding partner.

The solid support may be any material known to those of ordinary skill in the art to which the antigen may be attached. For example, the solid support may be a test well in a microtiter plate or a nitrocellulose or other suitable membrane. Alternatively, the support may be a bead or disc, such as glass, fiberglass, latex or a plastic material such as polystyrene or polyvinylchloride. The support may also be a magnetic particle or a fiber optic sensor, such as those disclosed, for example, in U.S. Pat. No. 5,359,681. The binding agent may be immobilized on the solid support using a variety of techniques known to those of skill in the art, which are amply described in the patent and scientific literature. In the context of the present invention, the term "immobilization" refers to both noncovalent association, such as adsorption, and covalent attachment (which may be a direct linkage between the antigen and functional groups on the support or may be a linkage by way of a cross-linking agent). Immobilization by adsorption to a well in a microtiter plate or to a membrane is preferred. In such cases, adsorption may be achieved by contacting the binding agent, in a suitable buffer, with the solid support for a suitable amount of time. The contact time varies with temperature, but is typically between about 1 hour and about 1 day. In general, contacting a well of a plastic microtiter plate (such as polystyrene or polyvinylchloride) with an amount of binding agent ranging from about 10 ng to about 10 μg, and preferably about 100 ng to about 1 μg, is sufficient to immobilize an adequate amount of binding agent.

Covalent attachment of binding agent to a solid support may generally be achieved by first reacting the support with a bifunctional reagent that will react with both the support and a functional group, such as a hydroxyl or amino group, on the binding agent. For example, the binding agent may be covalently attached to supports having an appropriate polymer coating using benzoquinone or by condensation of an aldehyde group on the support with an amine and an active hydrogen on the binding partner (see, e.g., Pierce Immunotechnology Catalog and Handbook, 1991, at A12–A13).

In certain embodiments, the assay is a two-antibody sandwich assay. This assay may be performed by first contacting an antibody that has been immobilized on a solid support, commonly the well of a microtiter plate, with the sample, such that polypeptides within the sample are allowed to bind to the immobilized antibody. Unbound sample is then removed from the immobilized polypeptide-antibody complexes and a second antibody (containing a reporter group) capable of binding to a different site on the polypeptide is added. The amount of second antibody that remains bound to the solid support is then determined using a method appropriate for the specific reporter group.

More specifically, once the antibody is immobilized on the support as described above, the remaining protein binding sites on the support are typically blocked. Any suitable blocking agent known to those of ordinary skill in the art, such as bovine serum albumin or Tween 20™ (Sigma Chemical Co., St. Louis, Mo.). The immobilized antibody is then incubated with the sample, and polypeptide is allowed to bind to the antibody. The sample may be diluted with a suitable diluent, such as phosphate-buffered saline (PBS) prior to incubation. In general, an appropriate contact time (i.e., incubation time) is that period of time that is sufficient to detect the presence of polypeptide within a sample obtained from an individual with breast cancer. Preferably, the contact time is sufficient to achieve a level of binding that is at least about 95% of that achieved at equilibrium between bound and unbound polypeptide. Those of ordinary skill in the art will recognize that the time necessary to achieve equilibrium may be readily determined by assaying the level of binding that occurs over a period of time. At room temperature, an incubation time of about 30 minutes is generally sufficient.

Unbound sample may then be removed by washing the solid support with an appropriate buffer, such as PBS containing 0.1% Tween 20™. The second antibody, which contains a reporter group, may then be added to the solid support. Preferred reporter groups include enzymes (such as horseradish peroxidase), substrates, cofactors, inhibitors, dyes, radionuclides, luminescent groups, fluorescent groups and biotin. The conjugation of antibody to reporter group may be achieved using standard methods known to those of ordinary skill in the art.

The second antibody is then incubated with the immobilized antibody-polypeptide complex for an amount of time sufficient to detect the bound polypeptide. An appropriate amount of time may generally be determined by assaying the level of binding that occurs over a period of time. Unbound second antibody is then removed and bound second antibody is detected using the reporter group. The method employed for detecting the reporter group depends upon the nature of the reporter group. For radioactive groups, scintillation counting or autoradiographic methods are generally appropriate. Spectroscopic methods may be used to detect dyes, luminescent groups and fluorescent groups. Biotin may be detected using avidin, coupled to a different reporter group (commonly a radioactive or fluorescent group or an enzyme). Enzyme reporter groups may generally be detected by the addition of substrate (generally for a specific period of time), followed by spectroscopic or other analysis of the reaction products.

To determine the presence or absence of breast cancer, the signal detected from the reporter group that remains bound to the solid support is generally compared to a signal that corresponds to a predetermined cut-off value. In one preferred embodiment, the cut-off value is the average mean signal obtained when the immobilized antibody is incubated with samples from patients without breast cancer. In general, a sample generating a signal that is three standard deviations above the predetermined cut-off value is considered positive for breast cancer. In an alternate preferred embodiment, the cut-off value is determined using a Receiver Operator Curve, according to the method of Sackett et al., *Clinical Epidemiology: A Basic Science for Clinical Medicine*, Little Brown and Co., 1985, p. 106–7. Briefly, in this embodiment, the cut-off value may be determined from a plot of pairs of true positive rates (i.e., sensitivity) and false positive rates (100%-specificity) that correspond to each possible cut-off value for the diagnostic test result. The cut-off value on the plot that is the closest to the upper left-hand corner (i.e., the value that encloses the largest area) is the most accurate cut-off value, and a sample generating a signal that is higher than the cut- off value determined by this method may be considered positive. Alternatively, the cut-off value may be shifted to the left along the plot, to minimize the false positive rate, or to the right, to minimize the false negative rate. In general, a sample generating a signal that is higher than the cut-off value determined by this method is considered positive for breast cancer.

In a related embodiment, the assay is performed in a flow-through or strip test format, wherein the antibody is immobilized on a membrane, such as nitrocellulose. In the flow-through test, polypeptides within the sample bind to the immobilized antibody as the sample passes through the membrane. A second, labeled antibody then binds to the antibody-polypeptide complex as a solution containing the second antibody flows through the membrane. The detection of bound second antibody may then be performed as described above. In the strip test format, one end of the membrane to which antibody is bound is immersed in a solution containing the sample. The sample migrates along the membrane through a region containing second antibody and to the area of immobilized antibody. Concentration of second antibody at the area of immobilized antibody indicates the presence of breast cancer. Typically, the concentration of second antibody at that site generates a pattern, such as a line, that can be read visually. The absence of such a pattern indicates a negative result. In general, the amount of antibody immobilized on the membrane is selected to generate a visually discernible pattern when the biological sample contains a level of polypeptide that would be sufficient to generate a positive signal in the two-antibody sandwich assay, in the format discussed above. Preferably, the amount of antibody immobilized on the membrane ranges from about 25 ng to about 1 $\mu$g, and more preferably from about 50 ng to about 500 ng. Such tests can typically be performed with a very small amount of biological sample.

Of course, numerous other assay protocols exist that are suitable for use with the antigens or antibodies of the present invention. The above descriptions are intended to be exemplary only.

In another embodiment, the above polypeptides may be used as markers for the progression of breast cancer. In this embodiment, assays as described above for the diagnosis of breast cancer may be performed over time, and the change in the level of reactive polypeptide(s) evaluated. For example, the assays may be performed every 24–72 hours for a period of 6 months to 1 year, and thereafter performed as needed. In general, breast cancer is progressing in those patients in whom the level of polypeptide detected by the binding agent increases over time. In contrast, breast cancer is not progressing when the level of reactive polypeptide either remains constant or decreases with time.

Antibodies for use in the above methods may be prepared by any of a variety of techniques known to those of ordinary skill in the art. See, e.g., Harlow and Lane, *Antibodies: A Laboratory Manual*, Cold Spring Harbor Laboratory, 1988. In one such technique, an immunogen comprising the antigenic polypeptide is initially injected into any of a wide variety of mammals (e.g., mice, rats, rabbits, sheep and goats). In this step, the polypeptides of this invention may serve as the immunogen without modification. Alternatively, particularly for relatively short polypeptides, a superior immune response may be elicited if the polypeptide is joined to a carrier protein, such as bovine serum albumin or keyhole limpet hemocyanin. The immunogen is injected into the animal host, preferably according to a predetermined schedule incorporating one or more booster immunizations, and the animals are bled periodically. Polyclonal antibodies specific for the polypeptide may then be purified from such antisera by, for example, affinity chromatography using the polypeptide coupled to a suitable solid support.

Monoclonal antibodies specific for the antigenic polypeptide of interest may be prepared, for example, using the technique of Kohler and Milstein, *Eur. J. Immunol.* 6:511–519, 1976, and improvements thereto. Briefly, these methods involve the preparation of immortal cell lines capable of producing antibodies having the desired specificity (i.e., reactivity with the polypeptide of interest). Such cell lines may be produced, for example, from spleen cells obtained from an animal immunized as described above. The spleen cells are then immortalized by, for example, fusion with a myeloma cell fusion partner, preferably one that is syngeneic with the immunized animal. A variety of fusion techniques may be employed. For example, the spleen cells and myeloma cells may be combined with a nonionic detergent for a few minutes and then plated at low density on a selective medium that supports the growth of hybrid cells, but not myeloma cells. A preferred selection technique uses HAT (hypoxanthine, aminopterin, thymidine) selection. After a sufficient time, usually about 1 to 2 weeks, colonies of hybrids are observed. Single colonies are selected and tested for binding activity against the polypeptide. Hybridomas having high reactivity and specificity are preferred.

Monoclonal antibodies may be isolated from the supernatants of growing hybridoma colonies. In addition, various techniques may be employed to enhance the yield, such as injection of the hybridoma cell line into the peritoneal cavity of a suitable vertebrate host, such as a mouse. Monoclonal antibodies may then be harvested from the ascites fluid or the blood. Contaminants may be removed from the antibodies by conventional techniques, such as chromatography, gel filtration, precipitation, and extraction. The polypeptides of this invention may be used in the purification process in, for example, an affinity chromatography step.

Monoclonal antibodies of the present invention may also be used as therapeutic reagents, to diminish or eliminate breast tumors. The antibodies may be used on their own (for instance, to inhibit metastases) or coupled to one or more therapeutic agents. Suitable agents in this regard include radionuclides, differentiation inducers, drugs, toxins, and derivatives thereof. Preferred radionuclides include $^{90}$Y, $^{123}$I, $^{125}$I, $^{131}$I, $^{186}$Re, $^{188}$Re, $^{211}$At, and $^{212}$Bi. Preferred drugs include methotrexate, and pyrimidine and purine analogs. Preferred differentiation inducers include phorbol esters and butyric acid. Preferred toxins include ricin, abrin, diptheria toxin, cholera toxin, gelonin, Pseudomonas exotoxin, Shigella toxin, and pokeweed antiviral protein.

A therapeutic agent may be coupled (e.g., covalently bonded) to a suitable monoclonal antibody either directly or indirectly (e.g., via a linker group). A direct reaction between an agent and an antibody is possible when each possesses a substituent capable of reacting with the other. For example, a nucleophilic group, such as an amino or sulfhydryl group, on one may be capable of reacting with a carbonyl-containing group, such as an anhydride or an acid halide, or with an alkyl group containing a good leaving group (e.g., a halide) on the other.

Alternatively, it may be desirable to couple a therapeutic agent and an antibody via a linker group. A linker group can function as a spacer to distance an antibody from an agent in order to avoid interference with binding capabilities. A linker group can also serve to increase the chemical reactivity of a substituent on an agent or an antibody, and thus increase the coupling efficiency. An increase in chemical reactivity may also facilitate the use of agents, or functional groups on agents, which otherwise would not be possible.

It will be evident to those skilled in the art that a variety of bifunctional or polyfunctional reagents, both homo- and hetero-functional (such as those described in the catalog of the Pierce Chemical Co., Rockford, Ill.), may be employed as the linker group. Coupling may be effected, for example, through amino groups, carboxyl groups, sulfhydryl groups or oxidized carbohydrate residues. There are numerous references describing such methodology, e.g., U.S. Pat. No. 4,671,958, to Rodwell et al.

Where a therapeutic agent is more potent when free from the antibody portion of the immunoconjugates of the present invention, it may be desirable to use a linker group which is cleavable during or upon internalization into a cell. A number of different cleavable linker groups have been described. The mechanisms for the intracellular release of an agent from these linker groups include cleavage by reduction of a disulfide bond (e.g., U.S. Pat. No. 4,489,710, to Spitler), by irradiation of a photolabile bond (e.g., U.S. Pat. No. 4,625,014, to Senter et al.), by hydrolysis of derivatized amino acid side chains (e.g., U.S. Pat. No. 4,638,045, to Kohn et al.), by serum complement-mediated hydrolysis (e.g., U.S. Pat. No. 4,671,958, to Rodwell et al.), and acid-catalyzed hydrolysis (e.g., U.S. Pat. No. 4,569,789, to Blattler et al.).

It may be desirable to couple more than one agent to an antibody. In one embodiment, multiple molecules of an agent are coupled to one antibody molecule. In another embodiment, more than one type of agent may be coupled to one antibody. Regardless of the particular embodiment, immunoconjugates with more than one agent may be prepared in a variety of ways. For example, more than one agent may be coupled directly to an antibody molecule, or linkers which provide multiple sites for attachment can be used. Alternatively, a carrier can be used.

A carrier may bear the agents in a variety of ways, including covalent bonding either directly or via a linker group. Suitable carriers include proteins such as albumins (e.g., U.S. Pat. No. 4,507,234, to Kato et al.), peptides and polysaccharides such as aminodextran (e.g., U.S. Pat. No. 4,699,784, to Shih et al.). A carrier may also bear an agent by noncovalent bonding or by encapsulation, such as within a liposome vesicle (e.g., U.S. Pat. Nos. 4,429,008 and 4,873,088). Carriers specific for radionuclide agents include radiohalogenated small molecules and chelating compounds. For example, U.S. Pat. No. 4,735,792 discloses representative radiohalogenated small molecules and their synthesis. A radionuclide chelate may be formed from chelating compounds that include those containing nitrogen and sulfur atoms as the donor atoms for binding the metal, or metal oxide, radionuclide. For example, U.S. Pat. No. 4,673,562, to Davison et al. discloses representative chelating compounds and their synthesis.

A variety of routes of administration for the antibodies and immunoconjugates may be used. Typically, administration will be intravenous, intramuscular, subcutaneous or in the bed of a resected tumor. It will be evident that the precise dose of the antibody/immunoconjugate will vary depending upon the antibody used, the antigen density on the tumor, and the rate of clearance of the antibody.

Diagnostic reagents of the present invention may also comprise DNA sequences encoding one or more of the above polypeptides, or one or more portions thereof. For example, at least two oligonucleotide primers may be employed in a polymerase chain reaction (PCR) based assay to amplify breast tumor-specific cDNA derived from a biological sample, wherein at least one of the oligonucleotide primers is specific for a DNA molecule encoding a breast tumor protein of the present invention. The presence of the amplified cDNA is then detected using techniques well known in the art, such as gel electrophoresis. Similarly, oligonucleotide probes specific for a DNA molecule encoding a breast tumor protein of the present invention may be used in a hybridization assay to detect the presence of an inventive polypeptide in a biological sample.

As used herein, the term "oligonucleotide primer/probe specific for a DNA molecule" means an oligonucleotide sequence that has at least about 60%, preferably at least about 75% and more preferably at least about 90%, identity to the DNA molecule in question. Oligonucleotide primers and/or probes which may be usefully employed in the inventive diagnostic methods preferably have at least about 10–40 nucleotides. In a preferred embodiment, the oligonucleotide primers comprise at least about 10 contiguous nucleotides of a DNA molecule comprising a sequence selected from SEQ ID NOS: 1–67. Preferably, oligonucleotide probes for use in the inventive diagnostic methods comprise at least about 15 contiguous oligonucleotides of a DNA molecule comprising a sequence provided in SEQ ID NOS: 1–67. Techniques for both PCR based assays and hybridization assays are well known in the art (see, for example, Mullis et al. *Ibid; Ehrlich, Ibid*). Primers or probes may thus be used to detect breast tumor-specific sequences in biological samples, including blood, urine and/or breast tumor tissue.

The following Examples are offered by way of illustration and not by way of limitation.

EXAMPLE

Example 1

ISOLATION AND CHARACTERIZATION OF BREAST TUMOR POLYPEPTIDES

This Example describes the isolation of breast tumor polypeptides from a breast tumor cDNA library.

A human breast tumor cDNA expression library was constructed from a pool of breast tumor poly $A^+$ RNA from three patients using a Superscript Plasmid System for cDNA Synthesis and Plasmid Cloning kit (BRL Life Technologies, Gaithersburg, Md. 20897) following the manufacturer's protocol. Specifically, breast tumor tissues were homogenized with polytron (Kinematica, Switzerland) and total RNA was extracted using Trizol reagent (BRL Life Technologies) as directed by the manufacturer. The poly $A^+$ RNA was then purified using a Qiagen oligotex spin column mRNA purification kit (Qiagen, Santa Clarita, Calif. 91355) according to the manufacturer's protocol. First-strand cDNA was synthesized using the NotI/Oligo-dT18 primer. Double-stranded cDNA was synthesized, ligated with EcoRI/BstX I adaptors (Invitrogen, San Diego, Calif.) and digested with NotI. Following size fractionation with Chroma Spin-1000 columns (Clontech, Palo Alto, Calif. 94303), the cDNA was ligated into the EcoRI/NotI site of pCDNA3.1 (Invitrogen) and transformed into ElectroMax *E. coli* DH10B cells (BRL Life Technologies) by electroporation.

Using the same procedure, a normal human breast cDNA expression library was prepared from a pool of four normal breast tissue specimens. The cDNA libraries were characterized by determining the number of independent colonies, the percentage of clones that carried insert, the average insert size and by sequence analysis. The breast tumor library contained $1.14 \times 10^7$ independent colonies, with more than 90% of clones having a visible insert and the average insert size being 936 base pairs. The normal breast cDNA library contained $6 \times 10^6$ independent colonies, with 83% of clones having inserts and the average insert size being 1015 base pairs. Sequencing a analysis showed both libraries contain good complex cDNA clones that were synthesized from mRNA, with minimal rRNA and mitochondrial DNA contamination.

cDNA library subtraction was performed using the above breast tumor and normal breast cDNA libraries, as described by Hara et al. (*Blood*, 84:189–199, 1994) with some modifications. Specifically, a breast tumor-specific subtracted cDNA library was generated as follows. Normal breast cDNA library (70 μg) was digested, with EcoRI, NotI, and SfuI, followed by a filling-in reaction with DNA polymerase Klenow fragment. After phenol-chloroform extraction and ethanol precipitation, the DNA was dissolved in 100 μl of $H_2O$, heat-denatured and mixed with 100 μl (100 μg) of Photoprobe biotin (Vector Laboratories, Burlingame, Calif.), the resulting mixture was irradiated with a 270 W sunlamp on ice for 20 minutes. Additional Photoprobe biotin (50 μl) was added and the biotinylation reaction was repeated. After extraction with butanol five times, the DNA was ethanol-precipitated and dissolved in 23 μl $H_2O$ to form the driver DNA.

To form the tracer DNA, 10 μg breast tumor cDNA library was digested with BamHI and XhoI, phenol chloroform extracted and passed through Chroma spin-400 columns (Clontech). Following ethanol precipitation, the tracer DNA was dissolved in 5 μl $H_2O$. Tracer DNA was mixed with 15 μl driver DNA and 20 μl of 2×hybridization buffer (1.5 M NaCl/10 mM EDTA/50 mM HEPES pH 7.5/0.2% sodium dodecyl sulfate), overlaid with mineral oil, and heat-denatured completely. The sample was immediately transferred into a 68° C. water bath and incubated for 20 hours (long hybridization [LH]). The reaction mixture was then subjected to a streptavidin treatment followed by phenol/chloroform extraction. This process was repeated three more times. Subtracted DNA was precipitated, dissolved in 12 μl $H_2O$, mixed with 8 μl driver DNA and 20 μl of 2×hybridization buffer, and subjected to a hybridization at 68 ° C. for 2 hours (short hybridization [SH]). After removal of biotinylated double-stranded DNA, subtracted cDNA was ligated into BamHI/XhoI site of chloramphenicol resistant pBCSK$^+$ (Stratagene, La Jolla, Calif. 92037) and transformed into ElectroMax *E. coli* DH10B cells by electroporation to generate a breast tumor specific subtracted cDNA library.

To analyze the subtracted cDNA library, plasmid DNA was prepared from 100 independent clones, randomly picked from the subtracted breast tumor specific library and characterized by DNA sequencing with a Perkin Elmer/Applied Biosystems Division Automated Sequencer Model 373A (Foster City, Calif.). Thirty-eight distinct cDNA clones were found in the subtracted breast tumor-specific cDNA library. The determined 3' cDNA sequences for 14 of these clones are provided in SEQ ID NO: 1–14, with the corresponding 5' cDNA sequences being provided in SEQ ID NO: 15–28, respectively. The determined one strand (5' or 3' ) cDNA sequences for the remaining clones are provided in SEQ ID NO: 29–52. Comparison of these cDNA sequences with known sequences in the gene bank using the EMBL and GenBank databases (Release 97) revealed no significant homologies to the sequences provided in SEQ ID NO: 3, 10, 17, 24 and 45–52. The sequence provided in SEQ ID NO: 1, 2, 4–9, 11–16, 18–23, 25–41,43 and 44 were found to show at least some degree of homology to known human genes. The sequence of SEQ ID NO: 42 was found to show some homology to a known yeast gene.

To determine mRNA expression levels of cDNA clones from subtracted library, cDNA clones from the breast subtraction described above were colony PCR amplified and their mRNA expression levels in breast tumor, normal breast and various other normal tissues were determined using microarray technology (Synteni, Palo Alto, Calif.). Briefly, the PCR amplification products were arrayed onto slides in a high density, with each product occupying a unique location in the array. mRNA was extracted from the tissue sample to be tested, reverse transcribed, and fluorescent-labeled cDNA probes were generated. The microarrays were probed with the labeled cDNA probes, the slides scanned and fluorescence intensity was measured. Data was analyzed using Synteni provided GEMTOOLS Software. Fifteen distinct cDNA clones were found to be over-expressed in breast tumor and expressed at low levels in all normal tissues tested (breast, brain, liver, pancreas, lung, salivary gland, stomach, colon, kidney, bone marrow, skeletal muscle, PBMC, heart, small intestine, adrenal gland, spinal cord, large intestine and skin). The determined partial cDNA sequences for these clones are provided in SEQ ID NO: 53–67. Comparison of the sequences of SEQ ID NO: 53 and 54 with those in the gene bank as described above, revealed some homology to previously identified human genes. No significant homologies were found to the sequences of SEQ ID NO: 55–67.

Example 2

SYNTHESIS OF POLYPEPTIDES

Polypeptides may be synthesized on an Perkin Elmer/Applied Biosystems Division 430A peptide synthesizer using FMOC chemistry with HPTU (O-Benzotriazole-N,N,N',N'-tetramethyluronium hexafluorophosphate) activation. A Gly-Cys-Gly sequence may be attached to the amino terminus of the peptide to provide a method of conjugation, binding to an immobilized surface, or labeling of the peptide. Cleavage of the peptides from the solid support may be carried out using the following cleavage mixture: trifluoroacetic acid:ethanedithiol:thioanisole:water:phenol (40:1:2:2:3). After cleaving for 2 hours, the peptides may be precipitated in cold methyl-t-butyl-ether. The peptide pellets may then be dissolved in water containing 0.1% trifluoroacetic acid (TFA) and lyophilized prior to purification by C18 reverse phase HPLC. A gradient of 0%–60% acetonitrile (containing 0.1% TFA) in water (containing 0.1% TFA) may be used to elute the peptides. Following lyophilization of the pure fractions, the peptides may be characterized using electrospray or other types of mass spectrometry and by amino acid analysis.

From the foregoing, it will be appreciated that, although specific embodiments of the invention have been described herein for the purposes of illustration, various modifications may be made without deviating from the spirit and scope of the invention.

What is claimed is:

1. A method of detecting breast cancer in a patient, comprising:
   (a) obtaining a biological sample from the patient;
   (b) generating cDNA from the biological sample;
   (c) contacting the cDNA with at least two oligonucleotide primers in a polymerase chain reaction, wherein the oligonucleotide primers are specific for SEQ ID NO: 56; and
   (d) detecting an amount of the cDNA sequence comprising SEQ ID NO: 56 that amplifies in the presence of the oligonucleotide primers, the amount being greater than a predetermined cut-off value, and thereby detecting breast cancer, wherein the biological sample is a breast tissue sample.

2. A method of detecting breast cancer in a patient, comprising:
   (a) obtaining a biological sample from the patient;
   (b) generating cDNA from the biological sample;
   (c) contacting the cDNA with at least two oligonucleotide primers in a polymerase chain reaction, wherein the oligonucleotide primers are specific for SEQ ID NO: 61; and
   (d) detecting an amount of the cDNA sequence of SEQ ID NO: 61 that amplifies in the presence of the oligonucleotide primers, the amount being greater than a predetermined cut-off value, and thereby detecting breast cancer.

3. A method of detecting breast cancer in a patient, comprising:
   (a) obtaining a biological sample from the patient;
   (b) generating cDNA from the biological sample;
   (c) contacting the cDNA with at least two oligonucleotide primers in a polymerase chain reaction, wherein the oligonucleotide primers are specific for SEQ ID NO: 64; and
   (d) detecting an amount of the cDNA sequence of SEQ ID NO: 64 that amplifies in the presence of the oligonucleotide primers, the amount being greater than a predetermined cut-off value, and thereby detecting breast cancer.

4. The method of claim 1, wherein at least one of the oligonucleotide primers comprises at least about 10 contiguous nucleotides of SEQ ID NO:56.

5. The method of claim 2, wherein at least one of the oligonucleotide primers comprises at least about 10 contiguous nucleotides of SEQ ID NO:61.

6. The method of claim 3, wherein at least one of the oligonucleotide primers comprises at least about 10 contiguous nucleotides of SEQ ID NO:64.

7. The method of claim 2, wherein the biological sample is a breast tissue sample.

8. The method of claim 3, wherein the biological sample is a breast tissue sample.

* * * * *